US007282567B2

(12) United States Patent
Goldenberg et al.

(10) Patent No.: US 7,282,567 B2
(45) Date of Patent: *Oct. 16, 2007

(54) MONOCLONAL ANTIBODY HPAM4

(75) Inventors: David M. Goldenberg, Medham, NJ (US); Hans J. Hansen, Picayune, MS (US); Zhengxing Qu, Warren, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 437 days.

This patent is subject to a terminal disclaimer.

(21) Appl. No.: 10/461,885

(22) Filed: Jun. 16, 2003

(65) Prior Publication Data

US 2005/0014207 A1    Jan. 20, 2005

Related U.S. Application Data

(60) Provisional application No. 60/388,314, filed on Jun. 14, 2002.

(51) Int. Cl.
C07K 16/00 (2006.01)
(52) U.S. Cl. ............... 530/387.3; 530/350; 530/380; 530/385; 530/387.1; 530/388.1; 424/134.1; 424/135.1; 424/141.1; 424/155.1; 424/142.1; 424/178.1; 424/85.1; 435/7.9; 435/188; 435/320.1
(58) Field of Classification Search ............ 530/387.3, 530/350, 380, 385, 387.1, 387.7, 388.1; 424/134.1, 424/135.1, 141.1, 155.1, 142.1, 178.1, 85.1; 435/7.9, 188, 320.1, 54.1
See application file for complete search history.

(56) References Cited

U.S. PATENT DOCUMENTS

| | | | | |
|---|---|---|---|---|
| 5,693,762 A * | 12/1997 | Queen et al. | ............ | 530/387.3 |
| 5,776,427 A * | 7/1998 | Thorpe et al. | ............. | 424/1.49 |
| 5,859,205 A * | 1/1999 | Adair et al. | ............. | 530/387.3 |
| 6,017,514 A * | 1/2000 | Epstein et al. | ............... | 424/9.2 |
| 6,176,842 B1 * | 1/2001 | Tachibana et al. | ............ | 604/22 |
| 6,261,537 B1 * | 7/2001 | Klaveness et al. | ......... | 424/9.52 |
| 6,342,219 B1 * | 1/2002 | Thorpe et al. | ........... | 424/145.1 |
| 6,632,926 B1 * | 10/2003 | Chen et al. | .............. | 530/387.3 |
| 6,989,140 B2 * | 1/2006 | Tidmarsh et al. | ............ | 424/9.1 |
| 2002/0041847 A1 * | 4/2002 | Goldenberg | ............... | 424/1.49 |
| 2003/0096249 A1 * | 5/2003 | Westphal et al. | ............... | 435/6 |
| 2003/0198595 A1 * | 10/2003 | Goldenberg et al. | ....... | 424/1.49 |
| 2005/0002945 A1 * | 1/2005 | McBride et al. | ......... | 424/184.1 |

OTHER PUBLICATIONS

Price et al (Tumor Biology 1998, 19:1-20).*
Gold et al (Int J Cancer, 1994, 57:204-210).*
Ho et al (Semin. Oncol. 1997, 2:187-202).*
Walker et al (Pharmaceutical Research, 1995, 12:1548-1553).*
Gold, David V., et al., "Characterization of Monoclonal Antibody PAM4 Reactive with A pancreatic Cancer Mucin" Int. J. Cancer: 57, 204-210 (1994) XP-002963400.

Mariani, Giuliano, et al., "Inital Tumor Targeting, Biodistribution, and Pharmacokinetic Evaluation of the Monoclonal Antibody PAM4 in Patients with Pancreatic Cancer" Cancer Research Suppl. 55, 5911s-5915s Dec. 1, 1995.
Gold, David v., et al. "Radioimmunotherapy of Experimental Pancreatic Cancer with 131I-Labeled Monoclonal Antibody PAM4" Int. J. Cancer: 71, 660-667 (1997) XP-002258775.
Gold David V., et al., "Localization of pancreatic cancer with radiolabeled monoclonal antibody PAM4" Critical Reviews in Oncology/Hematology 39 (2001) 147-154 XP-002265616.
Cardillo, Thomas M. et al., "Therapeutic Advantage of 90Yttrium-versus 131Iodine-labeled PAM4 Antibody in Experimental Pancreatic Cancer" 3186 vol. 7, 3186-3192, Oct. 2001 Clinical Cancer Research XP-002258776.
Cardillo, Thomas M. "Combined Gemcitabine and Radioimmunotherapy for the Treatment of Pancreatic Cancer" Int. J. Cancer: 97, 386-392 (2002) XP-002265617.
Gold, D. V., et al., "Chimerization and CDR-grafted humanization of PAM4," Immunology—1993, p. 480 XP-001156924.
Dall'Acqua, William, et al., "Antibody Engineering" 8/198; Engineering and design, pp. 443-450 XP009003344, PD: Aug. 1998.
Kipriyanov, Wergey M., "Generation of Recombinant Antibodies" Molecular Biotechnology, vol. 12, Sep. 1999; pp. 173-201 XP009006067.
Clark, Mike, Antibody humanization: a case of the Emeror's new clothes? Immunology Today vol. 21, No. 8,Aug. 1, 2000, pp. 397-402.
Schuhmacher, Jochen, et al., "Pretargeting of human mammary carcinoma xenografts with bispecific anti-MUC1/anti-Ga chelate antibodies and immunoscintigraphy with PET" Nuclear Medicine and Biology 28 (2001) 821-828.
Klivenyi, Gabor, et al., "Gallium-68 Chelate Imaging of Human Colon Carcinoma Xenografts Pretargeted with Bispecific Anti-CD44 v6/Anti-Gallium Chelate Antibodies" The Journal of Nuclear Medicine vol. 39, No. 10, Oct. 1998, pp. 1769-1776 XP-002116382.
Karacay, H., et al., "A Pretargeting Bispecific Antibody Method for Improved Imaging and Therapy of Pacreatic Cancer" No. 1484, Poster Sessions Jun. 19, 2002 p. 1484; XP008023949.

* cited by examiner

*Primary Examiner*—Larry R. Helms
*Assistant Examiner*—Parithosh K. Tungaturthi
(74) *Attorney, Agent, or Firm*—Faegre & Benson, LLP

(57) ABSTRACT

This invention relates to monovalent and multivalent, monospecific antibodies and to multivalent, multispecific antibodies. One embodiment of these antibodies has one or more identical binding sites where each binding site binds with a target antigen or an epitope on a target antigen. Another embodiment of these antibodies has two or more binding sites where these binding sites have affinity towards different epitopes on a target antigen or different target antigens, or have affinity towards a target antigen and a hapten. The present invention further relates to recombinant vectors useful for the expression of these functional antibodies in a host. More specifically, the present invention relates to the tumor-associated antibody designated PAM4. The invention further relates to humanized and human PAM4 antibodies, and the use of such antibodies in diagnosis and therapy.

43 Claims, 8 Drawing Sheets

```
GATATTGTGATGACCCAGTCTCCAGCAATCATGTCTGCATCTCCTGGGGAGAAGGTCACCATGACCTGCAGTGCCAGCTCAAGTGTAAGT
 1                                      10                      20                    27  A
 D   I   V   M   T   Q   S   P   A   I   M   S   A   S   P   G   E   K   V   T   M   T   C   S   A   S   S   S   V   S
                                                                                                            ―――――――――――――
                                                                                                               CDR1

TCCAGCTACTTGTACTGGTACCAGCAGAAGCCAGGATCCTCCCCCAAACTCTGGATTTATAGCACATCCAACCTGGCTTCTGGAGTCCCT
30                              40                              50
 S   S   Y   L   Y   W   Y   Q   Q   K   P   G   S   S   P   K   L   W   I   Y   S   T   S   N   L   A   S   G   V   P
―――――――――――                                                             ―――――――――――――――――――――――
   CDR1                                                                           CDR2

GCTCGCTTCAGTGGCAGTGGGTCTGGGACCTCTTACTCTCTCACAATCAGCAGCATGGAGGCTGAAGATGCTGCCTCTTATTTCTGCCAT
60                              70                              80
 A   R   F   S   G   S   G   S   G   T   S   Y   S   L   T   I   S   S   M   E   A   E   D   A   A   S   Y   F   C   H

CAGTGGAATAGGTACCCGTACACGTTCGGAGGGGGGACCAAGCTGGAAATAAAA
90                             100                107
 Q   W   N   R   Y   P   Y   T   F   G   G   G   T   K   L   E   I   K
―――――――――――――――――――――――――
         CDR3
```

Figure 1A. Nucleotide and Amino Acid Sequences of Murine PAM4 V$_K$

```
GAGGTTCAGCTGCAGGAGTCTGGACCTGAGCTGGTGAAGCCTGGGGCTTCAGTGAAGATGTCCTGCAAGGCTTCTGGATACACATTCCCT
 1                      10                      20                      30
 E  V  Q  L  Q  E  S  G  P  E  L  V  K  P  G  A  S  V  K  M  S  C  K  A  S  G  Y  T  F  P

AGCTATGTTTTGCACTGGGTGAAGCAGAAGCCTGGGCAGGGCCTTGAGTGGATTGGATATATTAATCCTTACAATGATGGTACTCAGTAC
                        40                      50       52 A                           Y
 S  Y  V  L  H  W  V  K  Q  K  P  G  Q  G  L  E  W  I  G  Y  I  N  P  Y  N  D  G  T  Q  Y
     CDR1                                                                       CDR 2

AATGAGAAGTTCAAAGGCAAGGCCACACTGACTTCAGACAAATCGTCCAGCACAGCCTACATGGAGCTCAGCCGCCTGACCTCTGAGGAC
 60                     70                       80        82 A B C
 N  E  K  F  K  G  K  A  T  L  T  S  D  K  S  S  S  T  A  Y  M  E  L  S  R  L  T  S  E  D

TCTGCGGTCTATTACTGTGCAAGAGGCTTCGGTGGTAGCTACGGATTTGCTTACTGGGGCCAAGGGACTCTGATCACTGTCTCTGCA
                        90             100 A B                      110               113
 S  A  V  Y  Y  C  A  R  G  F  G  G  S  Y  G  F  A  Y  W  G  Q  G  T  L  I  T  V  S  A
                                      CDR3
```

Figure 1B. Nucleotide and Amino Acid Sequences of Murine PAM4 $V_H$

Figure 2A. cPAM4V$_K$

```
        1          10         20           27 A  30              40
        DIQLTQSPAIMSASPGEKVTMTCSASSSVSSSYLYWYQQKPGSSPKLWIY
                                   ‾‾‾‾‾‾‾‾‾‾‾‾‾‾
                                        CDR1
        50              60           70           80           90
        STSNLASGVPARFSGSGSGTSYSLTISSMEAEDAASYFCHQWNRYPYTFG
        ‾‾‾‾‾‾‾                                      ‾‾‾‾‾‾‾‾‾‾‾‾
         CDR2                                              CDR3
        100      108
        GGTKLEIKR
```

Figure 2B. cPAM4V$_H$

```
        1          10         20         30           40         50
        QVQLQESGPELVKPGASVKMSCKASGYTFPSYVLHWVKQKPGQGLEWIGY
                                        ‾‾‾‾‾‾‾‾
                                          CDR1
        52 A              60         70          80  82 A B C  90
        INPYNDGTQYNEKFKGKATLTSDKSSSTAYMELSRLTSEDSAVYYCARGF
        ‾‾‾‾‾‾‾‾‾‾‾‾‾‾‾                                     ‾‾‾‾
              CDR2                                          CDR3
               100 A B  110      113
        GGSYGFAYWGQGTLITVSS
        ‾‾‾‾‾‾‾‾‾
          CDR3
```

Figure 3A. Amino Acid Sequences of Walker $V_K$, PAM4 $V_K$, and Humanized PAM4 $V_K$

```
                                        10                  20                   30             40
Wil2  V_H    QVQLVQSGAEVKKPGSSVKVSCKASGGTFSSYAIS WVRQA
PAM4  V_H    E···QE··P·LV······A···M······Y··P··VLH··K·K
hPAM4 V_H    ····Q·······················Y··P··VLH··K·K 50 52 A                      60            70
Wil2  V_H    PGQGLEWMGGIIPIFGTANYAQKFQGRVTITADESTSTAY
PAM4  V_H    ··········I·Y·N·YNDGTQ·NE··K··KA·L·S·K·S·····
hPAM4 V_H    ··········I·Y·N·YNDGTQ·NE··K··KA·L···········

80 82 A B C              90           100 A B
Wil2  V_H    MELSSLRSEDTAVYYCARGPRLLADVLL
PAM4  V_H    ····R·T····S·············FGGSYGFAY
hPAM4 V_H    ·························FGGSYGFAY 103       110 113
NEWM  V_H    WGQGTLVTVSS
PAM4  V_H    ·····I···A·
hPAM4 V_H    ···········
```

Figure 3B. Amino Acid Sequences of Wil2 V_H, PAM4 V_H, Humanized PAM4 V_H and NEWM V_H

```
                PvuII
     GACATCCAGCTGACCCAGTCTCCATCCTCCCTGTCTGCATCTGTAGGAGACAGAGTCACCATGACCTGCAGTGCCAGCTCAAGTGTAAGT
       1                          10                        20                      27  A
     D  I  Q  L  T  Q  S  P  S  S  L  S  A  S  V  G  D  R  V  T  M  T  C  S  A  S  S  S  V  S
                                                                              CDR1

TCCAGCTACTTGTACTGGTACCAACAGAAACCAGGGAAAGCCCCCAAACTCTGGATTTATAGCACATCCAACCTGGCTTCTGGAGTCCCT
      30                                40                               50
     S  S  Y  L  Y  W  Y  Q  Q  K  P  G  K  A  P  K  L  W  I  Y  S  T  S  N  L  A  S  G  V  P
        CDR2

GCTCGCTTCAGTGGCAGTGGATCTGGGACAGACTTCACTCTCACCATCAGCAGTCTGCAACCTGAAGATTCTGCCTCTTATTTCTGCCAT
      60                                70                               80
     A  R  F  S  G  S  G  S  G  T  D  F  T  L  T  I  S  S  L  Q  P  E  D  S  A  S  Y  F  C  H

BglII/BclI
     CAGTGGAATAGGTACCCGTACACGTTCGGAGGGGGGACCAAGCTGGAGATCAAACGA
      90                                100               108
     Q  W  N  R  Y  P  Y  T  F  G  G  G  T  R  L  E  I  K  R
        CDR3
```

Figure 4A. Nucleotide Sequences of hPAM4 V$_K$

```
                  PstI
CAGGTGCAGCTGCAGCAGTCTGGGGCTGAGGTGAAGAAGCCTGGGGCCTCAGTGAAGGTGTCCTGCGAGGCTTCTGGATACACATTCCCT
 1              10               20                30
 Q  V  Q  L  Q  Q  S  G  A  E  V  K  K  P  G  A  S  V  K  V  S  C  E  A  S  G  Y  T  F  P

AGCTATGTTTTGCACTGGGTGAAGCAGGCCCCTGGACAAGGGCTTGAGTGGATTGGATATATTAATCCTTACAATGATGGTACTCAGTAC
       40                50        52 A           Y
 S  Y  V  L  H  W  V  K  Q  A  P  G  Q  G  L  E  W  I  G  Y  I  N  P  Y  N  D  G  T  Q  Y
       CDR1                                        CDR2

AATGAGAAGTTCAAAGGCAAGGCCACACTGACTAGGGACACGTCCATCAACACAGCCTACATGGAGCTGAGCAGGCTGAGATCTGACGAC
60              70                80    82 A B C
 N  E  K  F  K  G  K  A  T  L  T  R  D  T  S  I  N  T  A  Y  M  E  L  S  R  L  R  S  D  D

BstEII
ACGGCCCGTGTATTACTGTGCAAGAGGCTTCGGTGGTAGCTACGGATTTGCTTACTGGGGCCAGGGAACCCTGGTCACCGTCTCCTCA
       90                 100 A B                      110          103
 T  A  V  Y  Y  C  A  R  G  F  G  G  S  Y  G  F  A  Y  W  G  Q  G  T  L  V  T  V  S  S
                            CDR3
```

Figure 4B. Nucleotide Sequences of hPAM4 $V_H$

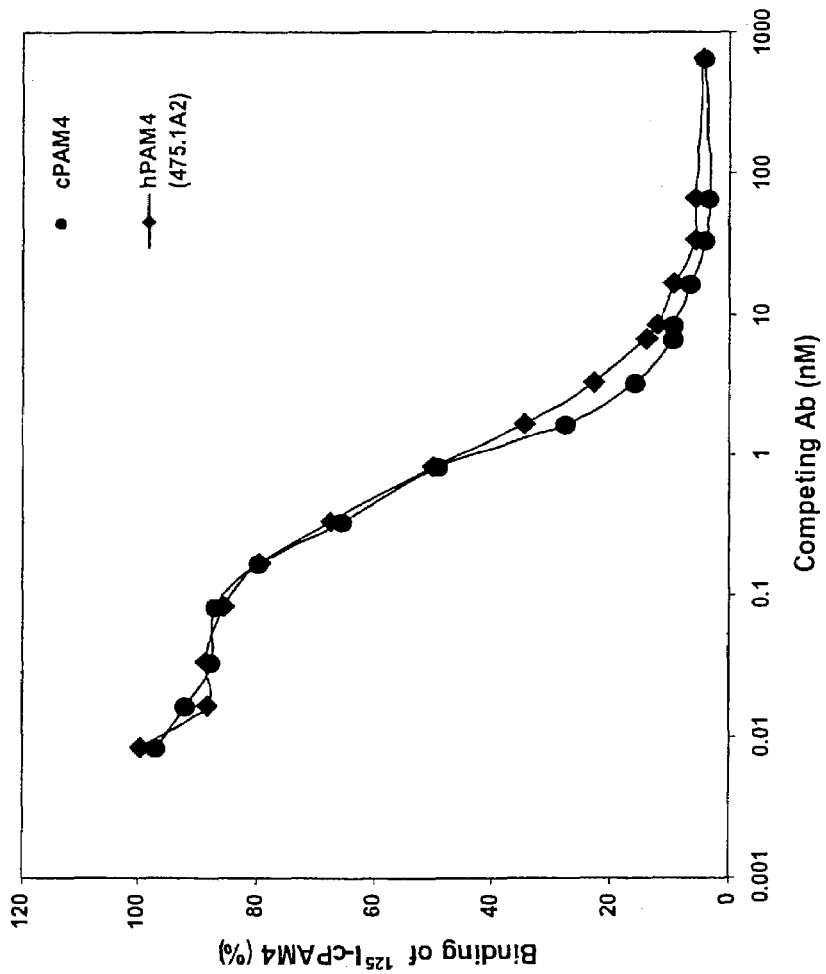
Figure 5. Binding Activity of Humanized PAM4 and Chimeric PAM4

SEQUENCE LISTING

```
<160> NUMBER OF SEQ ID NOS: 28

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: humanized
      PAM4 antibody fragment

<400> SEQUENCE: 1

Ser Ala Ser Ser Ser Val Ser Ser Ser Tyr Leu Tyr
 1               5                  10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: humanized
      PAM4 antibody fragment

<400> SEQUENCE: 2

Ser Thr Ser Asn Leu Ala Ser
 1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: humanized
      PAM4 antibody fragment
```

```
<400> SEQUENCE: 3

His Gln Trp Asn Arg Tyr Pro Tyr Thr
  1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: humanized
      PAM4 antibody fragment

<400> SEQUENCE: 4

Ser Tyr Val Leu His
  1               5

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: humanized
      PAM4 antibody fragment

<400> SEQUENCE: 5

Tyr Ile Asn Pro Tyr Asn Asp Gly Thr Gln Tyr Asn Glu Lys Phe Lys
  1               5                  10                  15

Gly

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: humanized
      PAM4 antibody fragment

<400> SEQUENCE: 6

Gly Phe Gly Gly Ser Tyr Gly Phe Ala Tyr
  1               5                  10

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Phe Lys Tyr Lys
  1

<210> SEQ ID NO 8
<211> LENGTH: 324
<212> TYPE: DNA
<213> ORGANISM: Mus musculus
<220> FEATURE:
<221> NAME/KEY: CDS
<222> LOCATION: (1)..(324)

<400> SEQUENCE: 8 gat att gtg atg acc cag tct cca gca atc atg tct gca tct cct ggg      48
Asp Ile Val Met Thr Gln Ser Pro Ala Ile Met Ser Ala Ser Pro Gly
  1               5                  10                  15 gag aag gtc acc atg acc tgc agt gcc agc tca agt gta agt tcc agc      96
```

```
                  Glu Lys Val Thr Met Thr Cys Ser Ala Ser Ser Val Ser Ser Ser
                                   20                  25                  30 tac ttg tac tgg tac cag cag aag cca gga tcc tcc ccc aaa ctc tgg          144
Tyr Leu Tyr Trp Tyr Gln Gln Lys Pro Gly Ser Ser Pro Lys Leu Trp
             35                  40                  45 att tat agc aca tcc aac ctg gct tct gga gtc cct gct cgc ttc agt          192
Ile Tyr Ser Thr Ser Asn Leu Ala Ser Gly Val Pro Ala Arg Phe Ser
     50                  55                  60 ggc agt ggg tct ggg acc tct tac tct ctc aca atc agc agc atg gag          240
Gly Ser Gly Ser Gly Thr Ser Tyr Ser Leu Thr Ile Ser Ser Met Glu
 65                  70                  75                  80 gct gaa gat gct gcc tct tat ttc tgc cat cag tgg aat agg tac ccg          288
Ala Glu Asp Ala Ala Ser Tyr Phe Cys His Gln Trp Asn Arg Tyr Pro
                 85                  90                  95 tac acg ttc gga ggg ggg acc aag ctg gaa ata aaa                          324
Tyr Thr Phe Gly Gly Gly Thr Lys Leu Glu Ile Lys
            100                 105
```

<210> SEQ ID NO 9
<211> LENGTH: 108
<212> TYPE: PRT
<213> ORGANISM: Mus musculus

<400> SEQUENCE: 9

```
Asp Ile Val Met Thr Gln Ser Pro Ala Ile Met Ser Ala Ser Pro Gly
 1               5                  10                  15

Glu Lys Val Thr Met Thr Cys Ser Ala Ser Ser Val Ser Ser Ser
                 20                  25                  30

Tyr Leu Tyr Trp Tyr Gln Gln Lys Pro Gly Ser Ser Pro Lys Leu Trp
             35                  40                  45

Ile Tyr Ser Thr Ser Asn Leu Ala Ser Gly Val Pro Ala Arg Phe Ser
     50                  55                  60

Gly Ser Gly Ser Gly Thr Ser Tyr Ser Leu Thr Ile Ser Ser Met Glu
 65                  70                  75                  80

Ala Glu Asp Ala Ala Ser Tyr Phe Cys His Gln Trp Asn Arg Tyr Pro
                 85                  90                  95

Tyr Thr Phe Gly Gly Gly Thr Lys Leu Glu Ile Lys
            100                 105
```

<210> SEQ ID NO 10
<211> LENGTH: 357
<212> TYPE: DNA
<213> ORGANISM: Mus musculus
<220> FEATURE:
<221> NAME/KEY: CDS
<222> LOCATION: (1)..(357)

<400> SEQUENCE: 10

```
gag gtt cag ctg cag gag tct gga cct gag ctg gta aag cct ggg gct          48
Glu Val Gln Leu Gln Glu Ser Gly Pro Glu Leu Val Lys Pro Gly Ala
 1               5                  10                  15 tca gtg aag atg tcc tgc aag gct tct gga tac aca ttc cct agc tat          96
Ser Val Lys Met Ser Cys Lys Ala Ser Gly Tyr Thr Phe Pro Ser Tyr
                 20                  25                  30 gtt ttg cac tgg gtg aag cag aag cct ggg cag ggc ctt gag tgg att          144
Val Leu His Trp Val Lys Gln Lys Pro Gly Gln Gly Leu Glu Trp Ile
             35                  40                  45 gga tat att aat cct tac aat gat ggt act cag tac aat gag aag ttc          192
Gly Tyr Ile Asn Pro Tyr Asn Asp Gly Thr Gln Tyr Asn Glu Lys Phe
     50                  55                  60
```

```
aaa ggc aag gcc aca ctg act tca gac aaa tcg tcc agc aca gcc tac      240
Lys Gly Lys Ala Thr Leu Thr Ser Asp Lys Ser Ser Ser Thr Ala Tyr
 65              70                  75                  80 atg gag ctc agc cgc ctg acc tct gag gac tct gcg gtc tat tac tgt      288
Met Glu Leu Ser Arg Leu Thr Ser Glu Asp Ser Ala Val Tyr Tyr Cys
             85                  90                  95 gca aga ggc ttc ggt ggt agc tac gga ttt gct tac tgg ggc caa ggg      336
Ala Arg Gly Phe Gly Gly Ser Tyr Gly Phe Ala Tyr Trp Gly Gln Gly
            100                 105                 110 act ctg atc act gtc tct gca                                          357
Thr Leu Ile Thr Val Ser Ala
        115

<210> SEQ ID NO 11
<211> LENGTH: 119
<212> TYPE: PRT
<213> ORGANISM: Mus musculus

<400> SEQUENCE: 11

Glu Val Gln Leu Gln Glu Ser Gly Pro Glu Leu Val Lys Pro Gly Ala
 1               5                  10                  15

Ser Val Lys Met Ser Cys Lys Ala Ser Gly Tyr Thr Phe Pro Ser Tyr
             20                  25                  30

Val Leu His Trp Val Lys Gln Lys Pro Gly Gln Gly Leu Glu Trp Ile
         35                  40                  45

Gly Tyr Ile Asn Pro Tyr Asn Asp Gly Thr Gln Tyr Asn Glu Lys Phe
     50                  55                  60

Lys Gly Lys Ala Thr Leu Thr Ser Asp Lys Ser Ser Ser Thr Ala Tyr
 65              70                  75                  80

Met Glu Leu Ser Arg Leu Thr Ser Glu Asp Ser Ala Val Tyr Tyr Cys
             85                  90                  95

Ala Arg Gly Phe Gly Gly Ser Tyr Gly Phe Ala Tyr Trp Gly Gln Gly
            100                 105                 110

Thr Leu Ile Thr Val Ser Ala
        115

<210> SEQ ID NO 12
<211> LENGTH: 109
<212> TYPE: PRT
<213> ORGANISM: Artificial Sequence
<220> FEATURE:
<223> OTHER INFORMATION: Description of Artificial Sequence: Chimeric
      PAM4Vk

<400> SEQUENCE: 12

Asp Ile Gln Leu Thr Gln Ser Pro Ala Ile Met Ser Ala Ser Pro Gly
 1               5                  10                  15

Glu Lys Val Thr Met Thr Cys Ser Ala Ser Ser Ser Val Ser Ser Ser
             20                  25                  30

Tyr Leu Tyr Trp Tyr Gln Gln Lys Pro Gly Ser Ser Pro Lys Leu Trp
         35                  40                  45

Ile Tyr Ser Thr Ser Asn Leu Ala Ser Gly Val Pro Ala Arg Phe Ser
     50                  55                  60

Gly Ser Gly Ser Gly Thr Ser Tyr Ser Leu Thr Ile Ser Ser Met Glu
 65              70                  75                  80

Ala Glu Asp Ala Ala Ser Tyr Phe Cys His Gln Trp Asn Arg Tyr Pro
             85                  90                  95

Tyr Thr Phe Gly Gly Gly Thr Lys Leu Glu Ile Lys Arg
            100                 105
```

<210> SEQ ID NO 13
<211> LENGTH: 119
<212> TYPE: PRT
<213> ORGANISM: Artificial Sequence
<220> FEATURE:
<223> OTHER INFORMATION: Description of Artificial Sequence: Chimeric
      PAM4Vh

<400> SEQUENCE: 13

Gln Val Gln Leu Gln Glu Ser Gly Pro Glu Leu Val Lys Pro Gly Ala
 1               5                  10                  15

Ser Val Lys Met Ser Cys Lys Ala Ser Gly Tyr Thr Phe Pro Ser Tyr
                20                  25                  30

Val Leu His Trp Val Lys Gln Lys Pro Gly Gln Gly Leu Glu Trp Ile
            35                  40                  45

Gly Tyr Ile Asn Pro Tyr Asn Asp Gly Thr Gln Tyr Asn Glu Lys Phe
        50                  55                  60

Lys Gly Lys Ala Thr Leu Thr Ser Asp Lys Ser Ser Ser Thr Ala Tyr
 65                  70                  75                  80

Met Glu Leu Ser Arg Leu Thr Ser Glu Asp Ser Ala Val Tyr Tyr Cys
                85                  90                  95

Ala Arg Gly Phe Gly Gly Ser Tyr Gly Phe Ala Tyr Trp Gly Gln Gly
            100                 105                 110

Thr Leu Ile Thr Val Ser Ser
        115

<210> SEQ ID NO 14
<211> LENGTH: 107
<212> TYPE: PRT
<213> ORGANISM: Homo sapiens

<400> SEQUENCE: 14

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Asn Tyr
                20                  25                  30

Leu Ser Trp Tyr Gln Gln Lys Pro Gly Lys Ala Pro Lys Leu Leu Ile
            35                  40                  45

Tyr Ala Ala Ser Ser Leu Gln Ser Gly Val Thr Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Ser Ala Thr Tyr Tyr Cys Gln Gln Ser Tyr Ser Thr Leu Ile
                85                  90                  95

Thr Phe Gly Gln Gly Thr Arg Leu Glu Ile Lys
            100                 105

<210> SEQ ID NO 15
<211> LENGTH: 327
<212> TYPE: DNA
<213> ORGANISM: Artificial Sequence
<220> FEATURE:
<223> OTHER INFORMATION: Description of Artificial Sequence: Humanized
      PAM4Vk

<400> SEQUENCE: 15
gacatccagc tgacccagtc tccatcctcc ctgtctgcat ctgtaggaga cagagtcacc      60
atgacctgca gtgccagctc aagtgtaagt tccagctact gtactggta ccaacagaaa     120

```
ccagggaaag ccccccaaact ctggatttat agcacatcca acctggcttc tggagtccct    180
gctcgcttca gtggcagtgg atctgggaca gacttcactc tcaccatcag cagtctgcaa    240
cctgaagatt ctgcctctta tttctgccat cagtggaata ggtacccgta cacgttcgga    300 gggggggacac gactggagat caaacga                                       327
```

<210> SEQ ID NO 16
<211> LENGTH: 109
<212> TYPE: PRT
<213> ORGANISM: Artificial Sequence
<220> FEATURE:
<223> OTHER INFORMATION: Description of Artificial Sequence: Humanized
      PAM4Vk

<400> SEQUENCE: 16

```
Asp Ile Gln Leu Thr Gln Ser Pro Ser Ser Leu Ser Ala Ser Val Gly
  1               5                  10                  15

Asp Arg Val Thr Met Thr Cys Ser Ala Ser Ser Val Ser Ser Ser
             20                  25                  30

Tyr Leu Tyr Trp Tyr Gln Gln Lys Pro Gly Lys Ala Pro Lys Leu Trp
         35                  40                  45

Ile Tyr Ser Thr Ser Asn Leu Ala Ser Gly Val Pro Ala Arg Phe Ser
     50                  55                  60

Gly Ser Gly Ser Gly Thr Asp Phe Thr Leu Thr Ile Ser Ser Leu Gln
 65                  70                  75                  80

Pro Glu Asp Ser Ala Ser Tyr Phe Cys His Gln Trp Asn Arg Tyr Pro
                 85                  90                  95

Tyr Thr Phe Gly Gly Gly Thr Arg Leu Glu Ile Lys Arg
                100                 105
```

<210> SEQ ID NO 17
<211> LENGTH: 123
<212> TYPE: PRT
<213> ORGANISM: Homo sapiens

<400> SEQUENCE: 17

```
Gln Val Gln Leu Val Gln Ser Gly Ala Glu Val Lys Lys Pro Gly Ala
  1               5                  10                  15

Ser Val Lys Val Ser Cys Glu Ala Ser Gly Tyr Thr Phe Thr Gly His
             20                  25                  30

Tyr Met His Trp Val Arg Gln Ala Pro Gly Gln Gly Leu Glu Trp Met
         35                  40                  45

Gly Trp Ile Asn Pro Asn Ser Gly Gly Thr Asn Tyr Ala Glu Lys Phe
     50                  55                  60

Gln Gly Arg Val Thr Ile Thr Arg Asp Thr Ser Ile Asn Thr Ala Tyr
 65                  70                  75                  80

Met Glu Leu Ser Arg Leu Arg Ser Asp Asp Thr Ala Val Tyr Tyr Cys
                 85                  90                  95

Ala Arg Ala Ser Tyr Cys Gly Tyr Asp Cys Tyr Tyr Phe Phe Asp Tyr
                100                 105                 110

Trp Gly Gln Gly Thr Leu Val Thr Val Ser Ser
        115                 120
```

<210> SEQ ID NO 18
<211> LENGTH: 357
<212> TYPE: DNA
<213> ORGANISM: Artificial Sequence
<220> FEATURE:

<223> OTHER INFORMATION: Description of Artificial Sequence: Humanized
     PAM4Vh
<220> FEATURE:
<221> NAME/KEY: CDS
<222> LOCATION: (1)..(357)

<400> SEQUENCE: 18

```
cag gtg cag ctg cag cag tct ggg gct gag gtg aag aag cct ggg gcc      48
Gln Val Gln Leu Gln Gln Ser Gly Ala Glu Val Lys Lys Pro Gly Ala
1               5                   10                  15 tca gtg aag gtc tcc tgc gag gct tct gga tac aca ttc cct agc tat      96
Ser Val Lys Val Ser Cys Glu Ala Ser Gly Tyr Thr Phe Pro Ser Tyr
            20                  25                  30 gtt ttg cac tgg gtg aag cag gcc cct gga caa ggg ctt gag tgg att     144
Val Leu His Trp Val Lys Gln Ala Pro Gly Gln Gly Leu Glu Trp Ile
        35                  40                  45 gga tat att aat cct tac aat gat ggt act cag tac aat gag aag ttc     192
Gly Tyr Ile Asn Pro Tyr Asn Asp Gly Thr Gln Tyr Asn Glu Lys Phe
    50                  55                  60 aaa ggc aag gcc aca ctg acc agg gac acg tcc atc aac aca gcc tac     240
Lys Gly Lys Ala Thr Leu Thr Arg Asp Thr Ser Ile Asn Thr Ala Tyr
65                  70                  75                  80 atg gag ctg agc agg ctg aga tct gac gac acg gcc gtg tat tac tgt     288
Met Glu Leu Ser Arg Leu Arg Ser Asp Asp Thr Ala Val Tyr Tyr Cys
                85                  90                  95 gca aga ggc ttc ggt ggt agc tac gga ttt gct tac tgg ggc cag gga     336
Ala Arg Gly Phe Gly Gly Ser Tyr Gly Phe Ala Tyr Trp Gly Gln Gly
            100                 105                 110 acc ctg gtc acc gtc tcc tca                                         357
Thr Leu Val Thr Val Ser Ser
        115
```

<210> SEQ ID NO 19
<211> LENGTH: 119
<212> TYPE: PRT
<213> ORGANISM: Artificial Sequence
<220> FEATURE:
<223> OTHER INFORMATION: Description of Artificial Sequence: Humanized
     PAM4Vh

<400> SEQUENCE: 19

```
Gln Val Gln Leu Gln Gln Ser Gly Ala Glu Val Lys Lys Pro Gly Ala
1               5                   10                  15

Ser Val Lys Val Ser Cys Glu Ala Ser Gly Tyr Thr Phe Pro Ser Tyr
            20                  25                  30

Val Leu His Trp Val Lys Gln Ala Pro Gly Gln Gly Leu Glu Trp Ile
        35                  40                  45

Gly Tyr Ile Asn Pro Tyr Asn Asp Gly Thr Gln Tyr Asn Glu Lys Phe
    50                  55                  60

Lys Gly Lys Ala Thr Leu Thr Arg Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Phe Gly Gly Ser Tyr Gly Phe Ala Tyr Trp Gly Gln Gly
            100                 105                 110

Thr Leu Val Thr Val Ser Ser
        115
```

<210> SEQ ID NO 20
<211> LENGTH: 173
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 20
agtctggggc tgaggtgaag aagcctgggg cctcagtgaa ggtctcctgc gaggcttctg      60
gatacacatt ccctagctat gttttgcact gggtgaagca ggcccctgga caagggcttg     120
agtggattgg atatattaat ccttacaatg atggtactca gtacaatgag aag            173

<210> SEQ ID NO 21
<211> LENGTH: 173
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
agggttccct ggccccagta agcaaatccg tagctaccac cgaagcctct tgcacagtaa      60
tacacggccg tgtcgtcaga tctcagcctg ctcagctcca gtaggctgt gttgatggac      120 gtgtccctgg tcagtgtggc cttgcctttg aacttctcat tgtactgagt acc            173

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
caggtgcagc tgcagcagtc tggggctgag gtga                                  34

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tgaggagacg gtgaccaggg ttccctggcc cca                                   33

<210> SEQ ID NO 24
<211> LENGTH: 157
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cagtctccat cctccctgtc tgcatctgta ggagacagag tcaccatgac ctgcagtgcc      60
agctcaagtg taagttccag ctacttgtac tggtaccaac agaaaccagg gaaagccccc     120
aaactctgga tttatagcac atccaacctg gcttctg                              157

<210> SEQ ID NO 25
<211> LENGTH: 156
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 25 gtccccccte cgaacgtgta cgggtaccta ttccactgat ggcagaaata agaggcagaa        60
tcttcaggtt gcagactgct gatggtgaga gtgaagtctg tcccagatcc actgccactg       120
aagcgagcag ggactccaga agccaggttg gatgtg                                 156

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gacatccagc tgacccagtc tccatcctcc ctg                                     33

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ttagatctcc agtcgtgtcc cccctccgaa cgt                                     33

<210> SEQ ID NO 28
<211> LENGTH: 11
<212> TYPE: PRT
<213> ORGANISM: Homo sapiens

<400> SEQUENCE: 28

Trp Gly Gln Gly Thr Leu Val Thr Val Ser Ser
 1               5                  10
```

MONOCLONAL ANTIBODY HPAM4

CROSS REFERENCE TO RELATED APPLICATIONS

This application claims priority to U.S. Provisional Application No. 60/388,314, filed Jun. 14, 2002, which is incorporated herein by reference in its entirety.

FIELD OF THE INVENTION

This invention relates to monovalent and multivalent, monospecific antibodies and to multivalent, multispecific antibodies. Specifically, the present invention relates to a MUC1 antigen specific antibody designated PAM4. The invention further relates to humanized and human PAM4 antibodies and fragments thereof, and the use of such antibodies and fragments thereof in diagnosis and therapy.

In one embodiment, the antibodies of the present invention have one or more identical binding sites, wherein each binding site has an affinity toward a target antigen or an epitope on a target antigen. In another embodiment, the antibodies of the present invention have two or more binding sites which have an affinity toward the same or different epitopes on a target antigen or the same or different target antigens, or at least one binding site has an affinity toward a target antigen and at least one binding site has an affinity toward a hapten. The present invention also describes recombinant vectors useful for expressing the antibodies described herein in a host.

BACKGROUND OF THE INVENTION

The pancreas produces insulin to assist the body in converting glucose to energy and enzymes to assist the body in digesting food. Pancreatic cancer is a malignant growth of the pancreas that mainly occurs in the cells of the pancreatic ducts. This disease is the ninth most common form of cancer, yet it is the fourth and fifth leading cause of cancer deaths in men and women, respectively. Cancer of the pancreas is almost always fatal, with a five-year survival rate that is less than 3%.

The most common symptoms of pancreatic cancer include jaundice, abdominal pain, and weight loss, which, together with other presenting factors, are nonspecific in nature. Thus, diagnosing pancreatic cancer at an early stage of tumor growth is often difficult and requires considerable suspicion and extensive diagnostic work-up, often times including exploratory surgery. Endoscopic ultrasonography and computed tomography are the best noninvasive means available today for diagnosis of pancreatic cancer. However, reliable detection of small tumors, as well as differentiation of pancreatic cancer from focal pancreatitis, is troublesome. Unfortunately, the vast majority of patients are presently diagnosed at a late stage when the tumor has already extended outside of the capsule to invade surrounding organs and/or has metastasized extensively. Gold et al., *Crit. Rev. Oncology/Hematology*, 39:147-54 (2001). Late detection of the disease is common, and "early" pancreatic cancer diagnosis is rare in the clinical setting.

Current treatment procedures available for pancreatic cancer have not led to a cure, nor to a substantially improved survival time. Surgical resection has been the only modality that offers a chance at survival. However, due to a large tumor burden, only 10% to 25% of patients are candidates for "curative resection." For those patients undergoing a surgical treatment, the five-year survival rate is still poor, averaging only about 10%.

Early detection and diagnosis of pancreatic cancer, as well as appropriate staging of the disease, would provide an increased survival advantage. A number of laboratories are proceeding on the development of a diagnostic procedure based upon the release of a tumor-associated marker into the bloodstream as well as detection of the marker substance within biopsy specimens. The best tumor associated marker for pancreatic cancer has been the immunoassay for CA19.9. Elevated levels of this sialylated $Le^a$ epitope structure were found in 70% of pancreatic cancer patients but were not found in any of the focal pancreatitis specimens examined. However, CA19.9 levels were found to be elevated in a number of other malignant and benign conditions, so that currently the assay cannot be used for diagnosis. However, the assay is useful for monitoring, the continued increase in CA19.9 serum levels after surgery being indicative of a poor prognosis. Many other monoclonal antibodies (MAbs) have been reported with immunoassays for diagnosis in varying stages of development. These include but are not limited to DUPAN2, SPAN1, B72.3, Ia3, and various anti-CEA antibodies.

Man-made antibodies, in particular MAbs and engineered antibodies or antibody fragments, have been tested widely and shown to be of value in detection and treatment of pancreatic cancer, as well as other various human disorders, including cancers, autoimmune diseases, infectious diseases, inflammatory diseases, and cardiovascular diseases [Filpula and McGuire, Exp. Opin. Ther. Patents (1999) 9: 231-245]. The clinical utility of an antibody or an antibody-derived agent is primarily dependent on its ability to bind to a specific targeted antigen associated with a specific disorder. Selectivity is valuable for delivering a diagnostic or therapeutic agent, such as isotopes, drugs, toxins, cytokines, hormones, hormone antagonists, enzymes, enzyme inhibitors, oligonucleotides, growth factors, oligonucleotides, radionuclides, an angiogenesis inhibitor, or metals, to a target location during the detection and treatment phases of a human disorder, particularly if the diagnostic or therapeutic agent is toxic to normal tissue in the body. Radiolabeled antibodies have been used with some success in numerous malignancies, including ovarian cancer, colon cancer and lymphoma. This technology may also prove useful for pancreatic cancer. However, other than the application of anti-CEA antibodies and B72.3, little clinical information exists.

The potential limitations of such antibody systems are discussed in Goldenberg, *The American Journal of Medicine*, 94: 298-299 (1993). The important parameters in the detection and treatment techniques are the amount of the injected dose specifically localized at the site(s) where target cells are present and the uptake ratio, i.e. the ratio of the concentration of specifically bound antibody to that of the radioactivity present in surrounding normal tissues. When an antibody is injected into the blood stream, it passes through a number of compartments as it is metabolized and excreted. The antibody must be able to locate and bind to the target cell antigen while passing through the rest of the body. Factors that control antigen targeting include location, size, antigen density, antigen accessibility, cellular composition of pathologic tissue, and the pharmacokinetics of the targeting antibodies. Other factors that specifically affect tumor targeting by antibodies include expression of the target antigens, both in tumor and other tissues, and bone marrow toxicity resulting from the slow blood-clearance of the radiolabeled antibodies. The amount of targeting antibodies accreted by the targeted tumor cells is influenced by the vascularization and barriers to antibody penetration of tumors, as well as intratumoral pressure. Non-specific uptake by non-target organs such as the liver, kidneys or bone-marrow is another potential limitation of the technique, especially for radioimmunotherapy, where irradiation of the bone marrow often causes the dose-limiting toxicity.

One suggested approach for delivering agents to a target site, referred to as direct targeting, is a technique designed to target specific antigens with antibodies carrying diagnostic or therapeutic radioisotopes. In the context of tumors, the direct targeting approach utilizes a radiolabeled anti-tumor monospecific antibody that recognizes the target tumor through its antigens. The technique involves injecting the labeled monospecific antibody into the patient and allowing the antibody to localize at the target tumor to obtain diagnostic or therapeutic benefits. The unbound antibody clears the body. This approach can be used to diagnose or treat additional mammalian disorders.

Another suggested solution, referred to as the "Affinity Enhancement System" (AES), is a technique especially designed to overcome deficiencies of tumor targeting by antibodies carrying diagnostic or therapeutic radioisotopes [U.S. Pat. No. 5,256,395 (1993), Barbet et al., *Cancer Biotherapy & Radiopharmaceuticals* 14: 153-166 (1999)]. The AES utilizes a radiolabeled divalent hapten and an anti-tumor/anti-hapten bispecific antibody that recognizes both the target tumor and the radioactive hapten. Haptens with higher valency and antibodies with higher specificity may also be utilized for this procedure. The technique involves injecting the antibody into the patient and allowing it to localize at the target tumor. After a sufficient amount of time for the unbound antibody to clear from the blood stream, the radiolabeled hapten is administered. The hapten binds to the antibody-antigen complex located at the site of the target cell to obtain diagnostic or therapeutic benefits, while the unbound hapten rapidly clears from the body. Barbet mentions the possibility that a bivalent hapten may crosslink with a bispecific antibody, when the latter is bound to the tumor surface. As a result, the radiolabeled complex is more stable and stays at the tumor for a longer period of time. This system can be used to diagnose or treat mammalian disorders.

There remains a need in the art for production of multivalent, monospecific antibodies that are useful in a direct targeting system and for production of multivalent, multispecific antibodies that are useful in an affinity enhancement system. Specifically, there remains a need for a antibody that performs as a useful diagnostic tool for pancreatic cancer and that exhibits enhanced uptake at targeted antigens, decreased concentration in the blood, and optimal protection of normal tissues and cells from toxic pharmaceuticals.

SUMMARY OF THE INVENTION

Contemplated in the present invention is an antibody, fusion protein, and fragments thereof that bind a domain located between the amino terminus and start of the repeat domain of MUC1. In a preferred embodiment the antibody, fusion protein, or fragment thereof is a PAM4 antibody. The PAM4 antibody, fusion protein, or fragment thereof of the present invention is derived by immunization and/or selection with mucin, and is preferably reactive against mucin of pancreatic cancer. Accordingly, the PAM4 antibody, fusion protein, and fragments thereof of the present invention preferably bind an antigen associated with pancreatic cancer cells.

In a preferred embodiment, the PAM4 antibody or fragment thereof is humanized or fully human, or the PAM4 fusion protein comprises a humanized or fully human PAM4 antibody or fragment thereof. Also preferred, the PAM4 antibody, fusion protein, and fragments thereof can be conjugated to at least one therapeutic and/or diagnostic agent.

Contemplated herein is a humanized PAM4 antibody or fragment thereof comprising the complementarity-determining regions (CDRs) of a murine PAM4 MAb and the framework (FR) regions of the light and heavy chain variable regions of a human antibody and the light and heavy chain constant regions of a human antibody, wherein the CDRs of the light chain variable region of the humanized PAM4 MAb comprise CDR1 comprising an amino acid sequence of SASSSVSSSYLY (SEQ ID NO: 1); CDR2 comprising an amino acid sequence of STSNLAS (SEQ ID NO: 2); and CDR3 comprising an amino acid sequence of HQWNRYPYT (SEQ ID NO: 3); and the CDRs of the heavy chain variable region of the humanized PAM4 MAb comprise CDR1 comprising an amino acid sequence of SYVLH (SEQ ID NO: 4); CDR2 comprising an amino acid sequence of YINPYNDGTQYNEKFKG (SEQ ID NO: 5) and CDR3 comprising an amino acid sequence of GFGGSYGFAY (SEQ ID NO: 6). In a preferred embodiment, the FRs of the light and heavy chain variable regions of the humanized PAM4 antibody or fragment thereof comprise at least one amino acid substituted from the corresponding FRs of a murine PAM4 MAb. Still preferred, the humanized PAM4 antibody or fragment thereof comprises at least one amino acid selected from the group consisting of amino acid residues 5, 27, 30, 38, 48, 66, 67, and 69 of the murine heavy chain variable region of FIG. 1B, PAM4 VH amino acid sequence. Also preferred, the humanized PAM4 antibody or fragment thereof wherein said amino acid from said murine MAb is at least one amino acid selected from the group consisting of amino acid residues 21, 47, 59, 60, 85, 87, and 100 of the murine light chain variable region FIG. 1A, PAM4Vκ sequence. Most preferably, the humanized PAM4 antibody or fragment thereof comprises the PAM4 Vκ nucleotide sequence of FIG. 1A and the PAM4 VH nucleotide sequence of FIG. 1B and/or comprises a hPAM4 $V_H$ amino acid sequence of FIG. 4A and a hPAM4 Vκ amino acid sequence of FIG. 4B.

Another embodiment of the present invention is a cancer cell targeting diagnostic immunoconjugate comprising an antibody component that comprises an antibody or fragment thereof of any one of the antibodies, fusion proteins, or fragments thereof of the present invention, wherein the antibody, fusion protein, or fragment thereof is bound to at least one diagnostic/detection agent.

Preferably, the diagnostic/detection agent is selected from the group comprising a radionuclide, a contrast agent, and a photoactive diagnostic/detection agent. Still preferred, the diagnostic/detection agent is a radionuclide with an energy between 20 and 4,000 keV or is a radionuclide selected from the group consisting of $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, or other gamma-, beta-, or positron-emitters. Also preferred, the diagnostic/detection agent is a paramagnetic ion, such as the a metal comprising chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), or a radioopaque material, such as barium, diatrizoate, ethiodized oil, gallium citrate, iocarmic acid, iocetamic acid, iodamide, iodipamide, iodoxamic acid, iogulamide, iohexol, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, and thallous chloride.

Also preferred, the diagnostic/detection agent is a fluorescent labeling compound selected from the group comprising fluorescein isothiocyanate, rhodamine, phycoerytherin, phycocyanin, allophycocyanin, o-phthaldehyde and fluorescamine, a chemiluminescent labeling compound selected from the group comprising luminol, isoluminol, an aromatic acridinium ester, an imidazole, an acridinium salt and an oxalate ester, or a bioluminescent compound selected from the group comprising luciferin, luciferase and acquorin. In another embodiment, the diagnostic immunoconjugates of the present invention are used in intraoperative, endoscopic, or intravascular tumor diagnosis.

Another embodiment of the present invention is a cancer cell targeting therapeutic immunoconjugate comprising an antibody component that comprises an antibody or fragment thereof of any one of the antibodies, fusion proteins, or fragments thereof of the present invention, wherein the antibody, fusion protein, or fragment thereof is bound to at least one therapeutic agent.

Preferably, the therapeutic agent is selected from the group consisting of a radionuclide, an immunomodulator, a hormone, a hormone antagonist, an enzyme, oligonucleotide, an enzyme inhibitor, a photoactive therapeutic agent, a cytotoxic agent, an angiogenesis inhibitor, and a combination thereof.

In one embodiment, an oligonucleotide, such as an antisense molecule inhibiting bcl-2 expression is described in U.S. Pat. No. 5,734,033 (Reed), which is incorporated by reference in its entirety, may be conjugated to, or form the therapeutic agent portion of an immunoconjugate or antibody fusion protein of the present invention. Alternatively, the oligonucleotide may be administered concurrently or sequentially with a naked or conjugated PAM4 antibody or antibody fragment of the present invention. In a preferred embodiment, the oligonucleotides is an antisense oligonucleotide that preferably is directed against an oncogene or oncogene product of a B-cell malignancy, such as bcl-2.

In a preferred embodiment, the therapeutic agent is a cytotoxic agent, such as a drug or a toxin. Also preferred, the drug is selected from the group consisting of nitrogen mustards, ethylenimine derivatives, alkyl sulfonates, nitrosoureas, gemcitabine, triazenes, folic acid analogs, anthracyclines, taxanes, COX-2 inhibitors, pyrimidine analogs, purine analogs, antibiotics, enzymes, enzyme inhibitors, epipodophyllotoxins, platinum coordination complexes, vinca alkaloids, substituted ureas, methyl hydrazine derivatives, adrenocortical suppressants, hormone antagonists, endostatin, taxols, camptothecins, SN-38, doxorubicins and their analogs, antimetabolites, alkylating agents, antimitotics, antiangiogenic, apoptotoic agents, methotrexate, CPT-11, and a combination thereof.

In another embodiment, the therapeutic agent is an oligonucleotide. For example, the oligonucleotide may be an antisense oligonucleotide such as an antisense oligonucleotide against an oncogene like bcl-2 and p53.

In another preferred embodiment, the therapeutic agent is a toxin selected from the group consisting of ricin, abrin, alpha toxin, saporin, ribonuclease (RNase), DNase I, *Staphylococcal* enterotoxin-A, pokeweed antiviral protein, gelonin, diphtherin toxin, *Pseudomonas* exotoxin, and *Pseudomonas* endotoxin and combinations thereof, an immunomodulator is selected from the group consisting of a cytokine, a stem cell growth factor, a lymphotoxin, a hematopoietic factor, a colony stimulating factor (CSF), an interferon (IFN), a stem cell growth factor, erythropoietin, thrombopoietin and a combinations thereof, a radionuclide selected from the group consisting of $^{32}$P, $^{33}$P, $^{47}$Sc, $^{64}$Cu, $^{67}$Cu, $^{67}$Ga, $^{86}$Y, $^{90}$Y, $^{111}$Ag, $^{111}$In, $^{125}$I, $^{131}$I, $^{142}$Pr, $^{153}$Sm, $^{161}$Tb, $^{166}$Dy, $^{166}$Ho, $^{177}$Lu, $^{186}$Re, $^{188}$Re, $^{189}$Re, $^{212}$Pb, $^{212}$Bi, $^{213}$Bi, $^{211}$At, $^{223}$Ra and $^{225}$Ac, and combinations thereof, or a photoactive therapeutic agent selected from the group comprising chromogens and dyes.

Still preferred, the therapeutic agent is an enzyme selected from the group comprising malate dehydrogenase, staphylococcal nuclease, delta-V-steroid isomerase, yeast alcohol dehydrogenase, α-glycerophosphate dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase and acetylcholinesterase.

Contemplated herein is a multivalent, multispecific antibody or fragment thereof comprising more than one antigen binding site having an affinity toward a PAM4 target antigen and one or more hapten binding sites having affinity towards hapten molecules. Preferably, the antibody or fragment thereof is a humanized or fully human antibody or fragment thereof. Also preferred, the multivalent, multispecific antibody or fragment thereof further comprises a diagnostic/detection and/or therapeutic agent.

Also described herein is a bispecific antibody or fragment thereof comprising at least one bnding site with an affinity toward a PAM4 target antigen and at least one binding site with an affinity toward a targetable construct/conjugates selected from the group consisting of:

DOTA-D-Asp-D-Lys(HSG)-D-Asp-D-Lys(HSG)-NH$_2$ (IMP 271);

DOTA-D-Glu-D-Lys(HSG)-D-Glu-D-Lys(HSG)-NH$_2$ (IMP 277);

DOTA-D-Tyr-D-Lys(HSG)-D-Glu-D-Lys(HSG)-NH$_2$ (IMP 288);

DOTA-D-Ala-D-Lys(HSG)-D-Glu-D-Lys(HSG)-NH$_2$ (IMP 0281); and

DOTA-D-Phe-D-Lys(HSG)-D-Tyr-D-Lys(HSG)-NH$_2$ (IMP 284), that is capable of carrying at least one diagnostic and/or therapeutic agent. Other targetable constructs suitable for use in the present invention are disclosed in U.S. Provisional application No. 60/479,403 entitled "D-Amino Acid Peptides" (McBride), filed Jun. 13, 2003.

Another embodiment of the present invention is an antibody fusion protein or fragment thereof comprising at least two PAM4 MAbs or fragments thereof, wherein the MAbs or fragments comprise any of the antibodies and fragments thereof of the present invention. Also preferred, the antibody fusion protein or fragment thereof comprises at least one first PAM4 MAb or fragment thereof of any one of the antibodies and fragments thereof of the present invention and at least one second MAb or fragment thereof, other than the MAb or fragment thereof of the antibodies and fragments thereof of the present invention. Preferably, the second MAb is a carcinoma-associated antibody, preferably selected from the group consisting of CA19.9, DUPAN2, SPAN1, Nd2, B72.3, CC49, CEA, aLe$^a$, antibodies defined by the Lewis antigen Le(y), and antibodies against CSAp, insulin-like growth factor (IGF), CD-80, placental growth factor (PlGF), carbonic anhydrase IX, tenascin, IL-6, MUC2, MUC3, MUC4, TAG-72, EGFR, CD40, platelet derived growth factor, IL-6, angiogenesis factors (e.g., VEGF), products of oncogenes, HER2/neu and antigens associated with renal cancer, gastric cancer and melanoma. The antibody fusion protein or fragments thereof of the present invention may further comprises at least one diagnostic and/or therapeutic agent.

Also described herein is a DNA sequence comprising a nucleic acid encoding a MAb or fragment thereof selected from the group consisting of:

(a) a PAM4 antibody or fragment thereof of any one of the antibodies described in the present invention;

(b) an antibody fusion protein or fragment thereof comprising at least two of the MAbs or fragments thereof described in (a);

(c) an antibody fusion protein or fragment thereof comprising at least one first PAM4 MAb or fragment thereof comprising said MAb or fragment thereof of the PAM4 antibodies or fragments thereof of the present invention and at least one second MAb or fragment thereof, other than the MAb or fragment thereof of any one of the antibodies or fragments thereof of the present invention; and (d) an antibody fusion protein or fragment thereof comprising at least one first MAb or fragment thereof comprising said MAb or fragment thereof of any one of the antibodies or fragments thereof of the present invention and at least one second MAb or fragment thereof, other than the MAb or fragment thereof of any one of antibodies or fragments thereof of the present invention, wherein the second MAb is a carcinoma associated antibody. Preferably, the carcinoma associated antibody is selected from the group consisting of CA19.9, DUPAN2, SPAN1, Nd2, B72.3, CC49, CEA, aLe$^a$, antibodies defined by the Lewis antigen Le(y), and antibodies against CD40, CD80, angiogenesis factors (e.g., VEGF and PlGF), carbonic anhydrase IX, products of oncogenes, MUC1, MUC-2, MUC-3, MUC-4, TAG-72, EGFR, insulin-like growth factor (IGF), platelet derived growth factor, tenascin, CD30, CD33, HLA-DR, IL-6, HER2/neu and antigens associated with renal cancer, gastric cancer and melanoma.

Also described in the present invention is an expression vector and host cell comprising the DNA sequence of any one of the antibodies, fusion proteins or fragments thereof of the present invention.

Another embodiment of the present invention is a method of delivering a diagnostic or therapeutic agent, or a combination thereof, to a target comprising (i) providing a composition that comprises a PAM4 antibody or fragment thereof conjugated to at least one diagnostic/detection and/or therapeutic agent and (ii) administering to a subject in need thereof the diagnostic or therapeutic conjugate of any one of antibodies, fusion proteins, or fragments thereof of the present invention. Preferably, the diagnostic/detection agent is selected from the group consisting of a radionuclide, a contrast agent, and a photoactive diagnostic/detection agent, and the therapeutic agent is preferably selected from the group consisting of a drug, toxin, cytotoxic agent, cytokine, immunomodulator, hormone, hormone antagonist, growth factor, radionuclide, metal.

Also contemplated in the present invention is a method of delivering a diagnostic/detection agent, a therapeutic agent, or a combination thereof to a target, comprising: (a) administering to a subject the antibody or fragment thereof of any one of the multivalent, multispecific antibodies or fragments thereof of the present invention that have an affinity toward a PAM4 antigen and comprise one or more hapten binding site; (b) waiting a sufficient amount of time for an amount of the non-antibody to clear the subject's blood stream; and (c) administering to said subject a carrier molecule comprising a diagnostic/detection agent, a therapeutic agent, or a combination thereof, that binds to a binding site of the antibody. Preferably, the carrier molecule binds to more than one binding site of the antibody. Still preferred, the diagnostic/detection agent or the therapeutic agent is selected from the group comprising isotopes, drugs, toxins, cytokines, oligonucleotides, hormones, hormone antagonists, enzymes, enzyme inhibitors, growth factors, radionuclides, and metals.

In one embodiment, an oligonucleotide, such as an antisense molecule inhibiting bcl-2 expression is described in U.S. Pat. No. 5,734,033 (Reed), which is incorporated by reference in its entirety, may be conjugated to, or form the therapeutic agent portion of an immunoconjugate or antibody fusion protein of the present invention. Alternatively, the oligonucleotide may be administered concurrently or sequentially with a naked or conjugated PAM4 antibody or antibody fragment of the present invention. In a preferred embodiment, the oligonucleotides is an antisense oligonucleotide that preferably is directed against an oncogene or oncogene product of a B-cell malignancy, such as bcl-2.

Described in the present invention is a method for diagnosing or treating cancer, comprising: (a) administering to a subject in need thereof the antibody or fragment thereof of any one of the multivalent, multispecific antibodies or fragments thereof of the present invention that have an affinity toward a PAM4 antigen and comprise one or more hapten binding sites; (b) waiting a sufficient amount of time for an amount of the non-bound antibody to clear the subject's blood stream; and (c) administering to said subject a carrier molecule comprising a diagnostic/detection agent, a therapeutic agent, or a combination thereof, that binds to a binding site of the antibody. In a preferred embodiment cancer is pancreatic cancer. Also preferred, the method can be used for intraoperative identification of diseased tissues, endoscopic identification of diseased tissues, or intravascular identification of diseased tissues.

Another embodiment of the present invention is a method of treating a malignancy in a subject comprising: (a) administering to said subject a therapeutically effective amount of an antibody or fragment thereof comprising a PAM4 MAb or fragment thereof or an antibody fusion protein or fragment thereof of any one of the antibodies, fusion proteins or fragments thereof of the present invention, wherein said PAM4 MAb or fragment thereof or antibody fusion protein or fragment thereof is conjugated to at least one therapeutic agent, and (b) formulating said PAM4 MAb or fragment thereof or antibody fusion protein or fragment thereof in a pharmaceutically suitable excipient. Preferably, the method further comprises a second MAb or fragment thereof not in any one of the antibodies, fusion proteins or fragments thereof of the present invention. Still preferred, the second MAb or fragment thereof is a naked MAb or fragment thereof. Also preferred, the second MAb or fragment thereof is selected from the group consisting of CA19.9, DUPAN2, SPAN1, Nd2, B72.3, CC49, CEA, aLe$^a$, antibodies defined by the Lewis antigen Le(y), and antibodies against CSAp, MUC1, MUC-2, MUC-3, MUC-4, TAG-72, EGFR, CD40, angiogenesis factors (e.g., VEGF), insulin-like growth factor (IGF), tenascin, platelet derived growth factor, IL-6, products of oncogenes and HER2/neu.

Contemplated herein is a method of diagnosing a malignancy in a subject comprising (a) administering to said subject a diagnostically effective amount of a diagnostic conjugate comprising a PAM4 MAb or fragment thereof or PAM4 antibody fusion protein or fragment thereof of any one of the antibodies, fusion proteins or fragments thereof of the present invention, wherein said PAM4 MAb or fragment thereof or PAM4 antibody fusion protein or fragment thereof is conjugated to at least one diagnostic/detection agent, and (b) optionally formulating said PAM4 MAb or fragment thereof or antibody fusion protein or fragment thereof in a pharmaceutically suitable excipient.

Another embodiment of the present invention is a method of treating a cancer cell in a subject comprising (i) administering to said subject a therapeutically effective amount of a composition comprising a naked PAM4 MAb or fragment thereof or a naked antibody fusion protein or fragment thereof of any one of the naked antibodies, fusion proteins, or fragments thereof of the present invention (ii) formulating said naked PAM4 MAb or fragment thereof or antibody fusion protein or fragment thereof in a pharmaceutically suitable excipient. Preferably, the method further comprises a second naked antibody or fragment thereof not any one of the naked antibodies, fusion proteins or fragments thereof of the present invention. For example, the second antibody or fragment thereof may be selected from the group consisting of CA19.9, DUPAN2, SPAN1, Nd2, B72.3, CC49, CEA, aLe$^a$, antibodies defined by the Lewis antigen Le(y), and antibodies against CSAp, MUC1, MUC-2, MUC-3, MUC-4, TAG-72, EGFR, CD40, CD52, HLA-DR, angiogenesis factors (e.g., VEGF), insulin-like growth factor (IGF), tenascin, platelet derived growth factor, IL-6, products of oncogenes and HER2/neu.

The present invention also describes a method of diagnosing a malignancy in a subject comprising (i) performing an in vitro diagnosis assay on a specimen from said subject with a composition comprising a naked PAM4 MAb or fragment thereof or a naked antibody fusion protein or fragment thereof of any one of the naked antibodies, fusion proteins, or fragments thereof of the present invention. Preferably, the malignancy is a cancer. Still preferred, the cancer is pancreatic cancer.

Another embodiment of the present invention is a method of intraoperatively identifying diseased tissues expressing PAM4 antigen, in a subject, comprising: (A) administering an effective amount of a bispecific antibody or antibody fragment comprising at least one arm that specifically binds a targeted tissue expressing PAM4-antigen and at least one other arm that specifically binds a targetable conjugate, wherein said one arm that specifically binds a targeted tissue is a hPAM4 antibody or fragment thereof and (B) administering a targetable conjugate selected from the group consisting of:

(i) DOTA-Phe-Lys(HSG)-D-Tyr-Lys(HSG)-NH$_2$;
(ii) DOTA-Phe-Lys(HSG)-Tyr-Lys(HSG)-NH$_2$; (SEQ ID NO: 7)
(iii) Ac-Lys(HSG)D-Tyr-Lys(HSG)-Lys(Tscg-Cys)-NH$_2$;

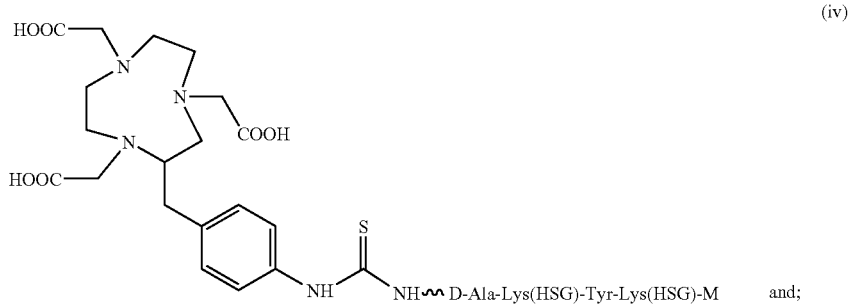

(iv)

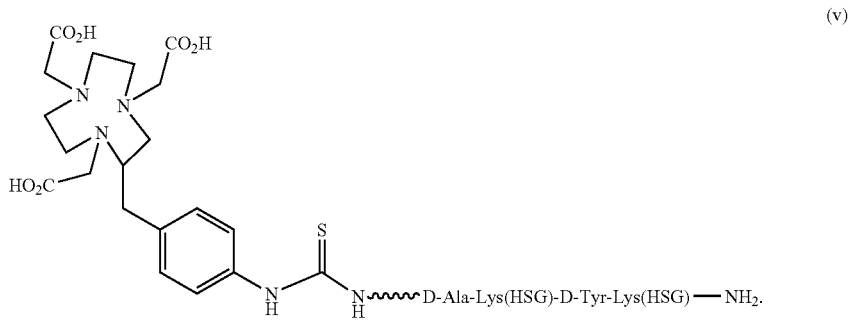

(v)

Also described herein is a method for the endoscopic identification of diseased tissues expressing PAM4 antigen, in a subject, comprising: (A) administering an effective amount of a bispecific antibody or antibody fragment comprising at least one arm that specifically binds a targeted tissue expressing PAM4-antigen and at least one other arm that specifically binds a targetable conjugate wherein said one arm that specifically binds a targeted tissue is a hPAM4 antibody or fragment thereof; and (B) administering a targetable conjugate selected from the group consisting of:

(i) DOTA-Phe-Lys(HSG)-D-Tyr-Lys(HSG)-NH$_2$;
(ii) DOTA-Phe-Lys(HSG)-Tyr-Lys(HSG)-NH$_2$; (SEQ ID NO: 7)
(iii) Ac-Lys(HSG)D-Tyr-Lys(HSG)-Lys(Tscg-Cys)-NH$_2$;

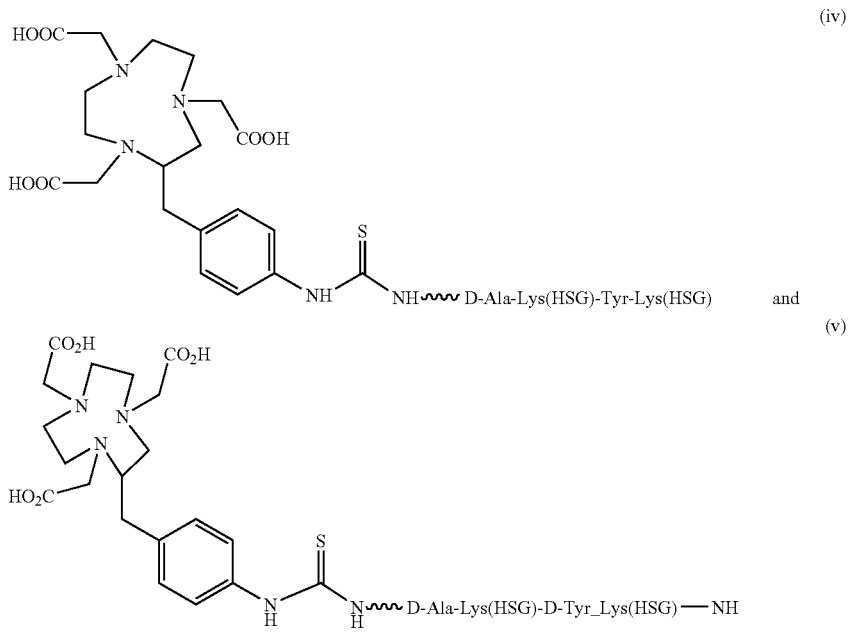

(iv)

(v)

Contemplated herein is a method for the intravascular identification of diseased tissues expressing PAM4 antigen, in a subject, comprising: (A) administering an effective amount of a bispecific antibody or antibody fragment comprising at least one arm that specifically binds a targeted tissue expressing PAM4-antigen and at least one other arm that specifically binds a targetable conjugate wherein said one arm that specifically binds a targeted tissue is a hPAM4 antibody or fragment thereof; and (B) administering a targetable conjugate selected from the group consisting of:
(i) DOTA-Phe-Lys(HSG)-D-Tyr-Lys(HSG)-NH$_2$;
(ii) DOTA-Phe-Lys(HSG)-Tyr-Lys(HSG)-N$_2$; (SEQ ID NO: 7)
(iii) Ac-Lys(HSG)D-Tyr-Lys(HSG)-Lys(Tscg-Cys)-NH$_2$;

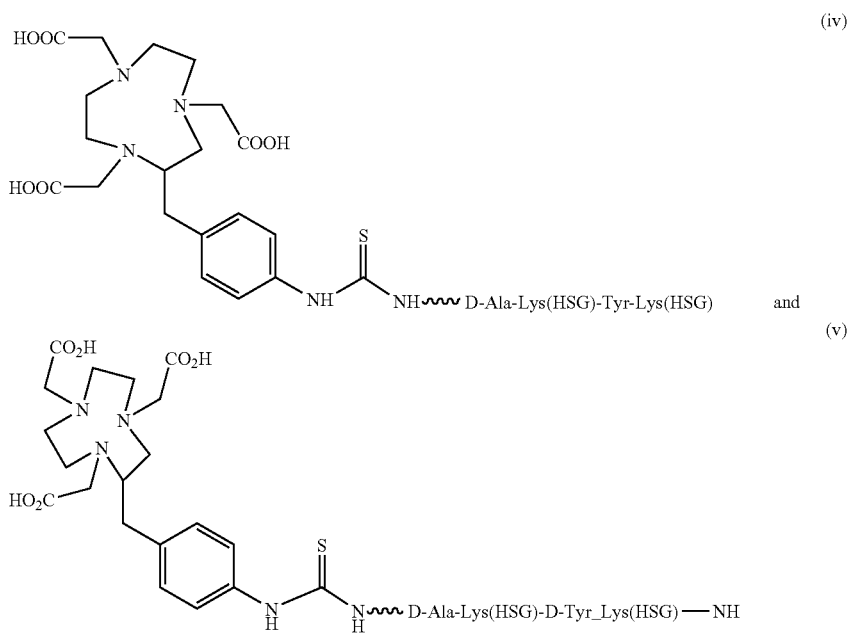

(iv)

(v)

Another embodiment is a method of detection of lesions during an endoscopic, intravascular catheter, or surgical procedure, wherein the method comprises: (a) injecting a subject who is to undergo such a procedure with a bispecific antibody F(ab)$_2$ or F(ab')$_2$ fragment thereof, diabody, triabody, or tetrabody., wherein said bispecific antibody or fragment thereof, diabody, triabody or tetrabody has a first antibody binding site which specifically binds to a PAM4 antigen, and has a second antibody binding site which specifically binds to a hapten, and permitting the antibody fragment to accrete at target sites; (b) optionally clearing non-targeted antibody fragments using a galactosylated anti-idiotype clearing agent if the bispecific fragment is not largely cleared from circulation within about 24 hours of injection, and injecting a bivalent labeled hapten, which quickly localizes at the target site and clears through the kidneys; (c) detecting the presence of the hapten by close-range detection of elevated levels of accreted label at the target sites with detection means, within 48 hours of the first injection, and conducting said procedure, wherein said detection is performed without the use of a contrast agent or subtraction agent.

A method for close-range lesion detection, during an operative, intravascular, or endoscopic procedure, wherein the method comprises: (a) injecting a subject to such a procedure parenterally with an effective amount of a hPAM4 immunoconjugate or fragment thereof, (b) conducting the procedure within 48 hours of the injection; (c) scanning the accessed interior of the subject at close range with a detection means for detecting the presence of said labeled antibody or fragment thereof; and (d) locating the sites of accretion of said labeled antibody or fragment thereof by detecting elevated levels of said labeled antibody or fragment thereof at such sites with the detection means, is also considered in the present invention.

BRIEF DESCRIPTION OF THE FIGURES

FIG. 1 shows the cloned V genes and the deduced amino acid sequences of the murine PAM4. FIG. 1A shows the DNA (SEQ ID NO: 8) and amino acid (SEQ ID NO: 9) sequences of the PAM4 Vk. FIG. 1B shows the DNA (SEQ ID NO: 10) and amino acid (SEQ ID NO: 11) sequences of the PAM4VH. Amino acid sequences encoded by the corresponding DNA sequences are given as one-letter codes below the nucleotide sequence. Numbering of the nucleotide sequence is on the right side. The amino acid residues in the CDR regions are shown in bold and underlined. Kabat's Ig molecule numbering is used for amino acid residues as shown by the numbering above the amino acid residues. The amino acid residues numbered by a letter are the insertion residues defined by Kabat numbering scheme. The insertion residues have the same preceding digits as that of the previous residue. For example, residues 82, 82A, 82B, and 82C in FIG. 1B are indicated as 82, A, B, and C, respectively.

FIG. 2 shows the amino acid sequences of the chimeric PAM4 (cPAM4) heavy and light chain variable regions expressed in Sp2/0 cells. FIG. 2A shows the amino acid sequence (SEQ ID NO: 12) of the cPAM4Vk. FIG. 2B shows the amino acid sequence (SEQ ID NO: 13) of the cPAM4VH. The sequences are given as one letter codes. The amino acid residues in the CDR regions are shown in bold and underlined. The numbering of amno acids is same as that in FIG. 1.

FIG. 3 shows the alignment of the amino acid sequences of heavy and light chain variable regions of a human antibody, PAM4 and hPAM4. FIG. 3A shows the Vκ amino acid sequence alignment of the human antibody Walker (SEQ ID NO: 14) with PAM4 (SEQ ID NO: 9) and hPAM4 (SEQ ID NO: 16), and FIG. 3B shows the VH amino acid sequence alignment of the human antibody Wil2 (FR1-3) (SEQ ID NO: 17) and NEWM (FR4) (SEQ ID NO: 28) with PAM4 (SEQ ID NO: 11) and hPAM4 (SEQ ID NO: 19). Dots indicate the residues of PAM4 are identical to the corresponding residues of the human antibodies. Boxed regions represent the CDR regions. Both N- and C-terminal residues (underlined) of hPAM4 are fixed by the staging vectors used. Kabat's Ig molecule number scheme is used to number the residues as in FIG. 1.

FIG. 4 shows the DNA and amino acid sequences of the humanized PAM4 (hPAM4) heavy and light chain variable regions expressed in Sp2/0 cells. FIG. 4A shows the DNA (SEQ ID NO: 15) and amino acid (SEQ ID NO: 16) sequences of the hPAM4Vκ. and FIG. 4B shows the DNA (SEQ ID NO: 18) and amino acid (SEQ ID NO: 19) sequences of the hPAM4VH. Numbering of the nucleotide sequence is on the right side. Amino acid sequences encoded by the corresponding DNA sequences are given as one-letter codes. The amino acid residues in the CDR regions are shown in bold and underlined. Kabat's Ig molecule numbering scheme is used for amino acid residues as in FIG. 1A and FIG. 1B.

FIG. 5 shows the binding activity of humanized PAM4 antibody, hPAM4, as compared to the chimeric PAM4, cPAM4. hPAM4 is shown by diamonds and cPAM4 is shown by closed circles. Results indicate comparable binding activity of the hPAM4 antibody and cPAM4 when competing with $^{125}$I-cPAM4 binding to CaPan1 Ag. A chimeric antibody is a recombinant protein that contains the variable domains including the complementarity determining regions (CDRs) of an antibody derived from one species while the constant domains of the antibody molecule is derived from those of a human antibody.

DETAILED DESCRIPTION OF THE PREFERRED EMBODIMENTS

Overview

Unless otherwise specified, "a" or "an" means "one or more." As described herein, the term "PAM4 antibody" includes murine, human, and humanized PAM4 antibodies.

The present invention relates to a monoclonal antibody, PAM4, that is useful for the diagnosis, detection, staging, and therapy of pancreatic cancer. Preferably, the PAM4 antibodies and fragments thereof of the present invention are humanized or fully human. The murine PAM4 (mPAM4) antibody is a MUC1 antibody developed by employing a pancreatic cancer mucin derived from the xenografted RIP-1 human pancreatic carcinoma as immunogen. Gold et al., *Int. J. Cancer,* 57:204-210 (1994). The mPAM4 antibody recognizes a unique and novel epitope on the target pancreatic cancer antigen. Immunohistochemical staining studies, such as those described in Example 1, have shown that the PAM4 MAb binds the domain located between the amino terminus and start of the repeat domain of a MUC1 antigen expressed by breast, pancreas and other cancer cells, with limited binding to normal human tissue. The PAM4 antibodies of the present invention are relatively specific to pancreatic cancer and therefore preferentially bind pancreatic cancer cells. In a preferred embodiment, the PAM4 antibodies and fragments thereof are humanized. The PAM4 antibody is reactive with a target epitope, which can be rapidly internalized. This epitope is expressed primarily by antigens associated with pancreatic cancer and not with focal pancreatitis. Localization and therapy studies using a radiolabeled PAM4 MAb in animal models have demonstrated tumor targeting and therapeutic efficacy.

The PAM4 antibodies of the present invention bind the PAM4 antigen, which is the domain located between the amino terminus and start of the repeat domain of MUC1, an antigen produced by many organs and tumor types. A preferred PAM4 antibody of the present invention preferentially binds pancreatic cancer cells. Studies with a PAM4 MAb, such as the PAM4 monoclonal antibody in Example 2, indicate that the antibody exhibits several important properties, which make it a candidate for clinical diagnostic and therapeutic applications. Since the PAM4 antigen provides a useful target for diagnosis and therapy, it is desirable to obtain a MAb that recognizes an epitope of a pancreatic cancer antigen that is distinct from the epitopes recognized by the non-PAM4 antibodies (CA19.9, DUPAN2, SPAN1, Nd2, B72.3, aLe$^a$, and the Lewis antigens) described in earlier studies.

Antibodies suitable for use in combination or conjunction with the PAM4 antibodies of the present invention include, for example, the antibodies CA19.9, DUPAN2, SPAN1, Nd2, B72.3, CC49, CEA, aLe$^a$, and antibodies defined by the Lewis antigen Le(y), or antibodies against carcinoembryonic antigen (CEA), colon-specific antigen-p (CSAp), MUC1, MUC2, MUC3, MUC4, HER2/neu, EGFR, angiogenesis factors (e.g., VEGF), insulin-like growth factor (IGF), tenascin, platelet derived growth factor, and IL-6, as well as products of oncogenes, and antibodies against tumor necrosis substances, such as described in patents by Epstein et al. (U.S. Pat. Nos. 6,071,491, 6,017,514, 5,019,368 and 5,882,626). Such antibodies would be useful for complementing current PAM4 antibody immunodetection and immunotherapy methods. In therapy applications, antibodies that are agonistic or antagonistic to immunomodulators involved in effector cell function against tumor cells could also be useful in combination with PAM4 antibodies alone or in combination with other tumor-associated antibodies, one example being antibodies against CD40. Todryk et al., *J. Immunol Methods*, 248:139-147 (2001); Turner et al., *J. Immunol*, 166:89-94 (2001). Also of use are antibodies against markers or products of oncogenes, or antibodies against angiogenesis factors, such as VEGF. VEGF antibodies are described in Thorpe et al., U.S. Pat. Nos. 6,342,221, 5,965,132 and 6,004,554, and are incorporated by reference in their entirety.

Moreover, the availability of another PAM4-like antibody is essential for the development of a double-determinant enzyme-linked immunosorbent assay (ELISA), which is useful for detecting a PAM4 antigen in clinical samples. ELISA experiments are described in Example 4 and 7.

The present invention describes humanized and fully human antibodies and fragments thereof that bind the domain located between the amino terminus and start of the repeat domain of MUC1 and can be used for diagnostic and therapeutic methods. In a preferred embodiment, the PAM4 antibody is humanized. Also preferred, the PAM4 antibodies of the present invention preferentially bind pancreatic cancer cells. Because non-human monoclonal antibodies can be recognized by the human host as a foreign protein, and repeated injections can lead to harmful hypersensitivity reactions, humanization of a murine PAM4 sequences can reduce the adverse immune response that patients may experience. For murine-based monoclonal antibodies, this is often referred to as a Human Anti-Mouse Antibody (HAMA) response. Preferably some human residues in the framework regions of the humanized PAM4 antibody or fragments thereof are replaced by their murine counterparts. It is also preferred that a combination of framework sequences from two different human antibodies are used for $V_H$. The constant domains of the antibody molecule are derived from those of a human antibody.

Another preferred embodiment of the present invention is a human PAM4 antibody. A human antibody is an antibody obtained, for example, from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994). A fully human antibody also can be constructed by genetic or chromosomal transfection methods, as well as phage display technology, all of which are known in the art. See for example, McCafferty et al., *Nature* 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g. Johnson and Chiswell, *Current Opinion in Structural Biology* 3:5564-571 (1993).

The antibodies and fragments thereof of the present invention are preferably raised against a crude mucin preparation from a tumor of the human pancreas. In a related vein, the PAM4 antibody can be obtained using a substantially pure preparation of the PAM4 antigen. A substantially pure protein is a protein that is essentially free from contaminating cellular components, which are associated with the protein in nature.

Definitions

In the description that follows, a number of terms are used and the following definitions are provided to facilitate understanding of the present invention.

An antibody, as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

An antibody fragment is a portion of an antibody such as F(ab')$_2$, F(ab)$_2$, Fab', Fab, Fv, sFv and the like. Regardless of structure, an antibody fragment binds with the same antigen that is recognized by the full-length antibody. For example, an anti-CD20 monoclonal antibody fragment binds with an epitope of CD20. The term "antibody fragment" also includes any synthetic or genetically engineered protein that acts like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A naked antibody is generally an antibody that is not conjugated to a therapeutic or diagnostic/detection agent. However, it may also be an antibody fragment that is not conjugated to a diagnostic/detection or therapeutic agent. This is so because the Fc portion of the antibody molecule provides effector functions, such as complement fixation and ADCC, (antibody dependent cell cytotoxicity), which set mechanisms into action that may result in cell lysis. However, it is possible that the Fc portion is not required for therapeutic function, with other mechanisms, such as apoptosis, coming into play. Naked antibodies include both polyclonal and monoclonal antibodies, as well as fusion proteins and certain recombinant antibodies, such as chimeric, humanized or human antibodies.

A chimeric antibody is a recombinant protein that contains the variable domains including the complementarity determining regions (CDRs) of an antibody derived from one species, preferably a rodent antibody, while the constant domains of the antibody molecule are derived from those of a human antibody. For veterinary applications, the constant domains of the chimeric antibody may be derived from that of other species, such as a cat or dog.

A humanized antibody is a recombinant protein in which the CDRs from an antibody from one species; e.g., a rodent antibody, are transferred from the heavy and light variable chains of the rodent antibody into human heavy and light variable domains. The constant domains of the antibody molecule are derived from those of a human antibody.

A human antibody is an antibody obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994). A fully human antibody also can be constructed by genetic or chromosomal transfection methods, as well as phage display technology, all of which are known in the art. See for example, McCafferty et al., *Nature* 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g. Johnson and Chiswell, *Current Opiniion in Structural Biology* 3:5564-571 (1993).

Human antibodies may also be generated by in vitro activated B cells. See U.S. Pat. Nos. 5,567,610 and 5,229,275, which are incoporated in their entirety by reference.

A therapeutic agent is a molecule or atom which is administered separately, concurrently or sequentially with an antibody moiety or conjugated to an antibody moiety, i.e., antibody or antibody fragment, or a subfragment, and is useful in the treatment of a disease. Examples of therapeutic agents include antibodies, antibody fragments, drugs, toxins, nucleases, hormones, immunomodulators, chelators, boron compounds, photoactive agents or dyes and radioisotopes.

A diagnostic/detection agent is a molecule or atom which is administered conjugated to an antibody moiety, i.e., antibody or antibody fragment, or subfragment, and is useful in diagnosing a disease by locating the cells containing the antigen. Useful diagnostic/detection agents include, but are not limited to, radioisotopes, dyes (such as with the biotin-streptavidin complex), contrast agents, fluorescent compounds or molecules and enhancing agents (e.g. paramagnetic ions) for magnetic resonance imaging (MRI). U.S. Pat. No. 6,331,175 describes MRI technique and the preparation of antibodies conjugated to a MRI enhancing agent and is incoporated in its entirety by reference. Preferably, the diagnostic/detection agents are selected from the group consisting of radioisotopes, enhancing agents for use in magnetic resonance imaging, and fluorescent compounds. In order to load an antibody component with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose. Chelates are coupled to the antibodies using standard chemistries. The chelate is normally linked to the antibody by a group, which enables formation of a bond to the molecule with minimal loss of immunoreactivity and minimal aggregation and/or internal cross-linking. Other, more unusual, methods and reagents for conjugating chelates to antibodies are disclosed in U.S. Pat. No. 4,824,659 to Hawthorne, entitled "Antibody Conjugates", issued Apr. 25, 1989, the disclosure of which is incorporated herein in its entirety by reference. Particularly useful metal-chelate combinations include 2-benzyl-DTPA and its monomethyl and cyclohexyl analogs, used with diagnostic isotopes in the general energy range of 60 to 4,000 keV, such as $^{125}$I, $^{131}$I, $^{123}$I, $^{124}$I, $^{62}$Cu, $^{64}$Cu, $^{18}$F, $^{111}$In, $^{67}$Ga, $^{68}$Ga, $^{99m}$Tc, $^{94m}$Tc, $^{11}$C, $^{13}$N, $^{15}$O, $^{76}$Br, for radioimaging. The same chelates, when complexed with non-radioactive metals, such as manganese, iron and gadolinium are useful for MRI, when used along with the antibodies of the invention. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}$Ra for RAIT are encompassed by the invention.

An immunoconjugate is an antibody, fusion protein, or fragment thereof conjugated to at least one therapeutic and/or diagnostic/detection agent. The diagnostic/detection agent can comprise a radionuclide or non-radionuclide, a contrast agent (such as for magnetic resonance imaging, computed tomography or ultrasound), and the radionuclide can be a gamma-, beta-, alpha-, Auger electron-, or positron-emitting isotope.

An expression vector is a DNA molecule comprising a gene that is expressed in a host cell. Typically, gene expression is placed under the control of certain regulatory elements, including constitutive or inducible promoters, tissue-specific regulatory elements and enhancers. Such a gene is said to be "operably linked to" the regulatory elements.

A recombinant host may be any prokaryotic or eukaryotic cell that contains either a cloning vector or expression vector. This term also includes those prokaryotic or eukaryotic cells, as well as transgenic animals, that have been genetically engineered to contain the cloned gene(s) in the chromosome or genome of the host cell or cells of the host cells. Suitable mammalian host cells include myeloma cells, such as SP2/0 cells, and NS0 cells, as well as Chinese Hamster Ovary (CHO) cells, hybridoma cell lines and other mammalian host cell useful for expressing antibodies. Also particularly useful to express mAbs and other fusion proteins, is a human cell line, PER.C6 disclosed in WO 0063403 A2, which produces 2 to 200-fold more recombinant protein as compared to conventional mammalian cell lines, such as CHO, COS, Vero, Hela, BHK and SP2-cell lines. Special transgenic animals with a modified immune system are particularly useful for making fully human antibodies.

As used herein, the term antibody fusion protein is a recombinantly produced antigen-binding molecule in which two or more of the same or different natural antibody, single-chain antibody or antibody fragment segments with the same or different specificities are linked. Valency of the fusion protein indicates the total number of binding arms or sites the fusion protein has to an antigen or epitope; i.e., monovalent, bivalent, trivalent or mutlivalent. The multivalency of the antibody fusion protein means that it can take advantage of multiple interactions in binding to an antigen, thus increasing the avidity of binding to the antigen. Specificity indicates how many antigens or epitopes an antibody fusion protein is able to bind; i.e., monospecific, bispecific, trispecific, multispecific. Using these definitions, a natural antibody, e.g., an IgG, is bivalent because it has two binding arms but is monospecific because it binds to one antigen. Monospecific, multivalent fusion proteins have more than one binding site for an epitope but only bind with the same or different epitopes on the same antigen, for example a diabody with two binding sites reactive with the same antigen. The fusion protein may comprise a multivalent or multispecific combination of different antibody components or multiple copies of the same antibody component. The fusion protein may additionally comprise a therapeutic agent. Examples of therapeutic agents suitable for such fusion proteins include immunomodulators ("antibody-immunomodulator fusion protein") and toxins ("antibody-toxin fusion protein"). One preferred toxin comprises a ribonuclease (RNase), preferably a recombinant RNase.

A multispecific antibody is an antibody that can bind simultaneously to at least two targets that are of different structure, e.g., two different antigens, two different epitopes on the same antigen, or a hapten and/or an antigen or epitope. One specificity would be for a B-cell, T-cell, myeloid-, plasma-, and mast-cell antigen or epitope. Another specificity could be to a different antigen on the same cell type, such as CD20, CD19, CD21, CD23, CD46, CD80, HLA-DR, CD74, and CD22 on B-cells. Multispecific, multivalent antibodies are constructs that have more than one binding site, and the binding sites are of different specificity. For example, a diabody, where one binding site reacts with one antigen and the other with the another antigen.

A bispecific antibody is an antibody that can bind simultaneously to two targets which are of different structure. Bispecific antibodies (bsAb) and bispecific antibody fragments (bsFab) have at least one arm that specifically binds to, for example, a B-cell, T-cell, myeloid-, plasma-, and mast-cell antigen or epitope and at least one other arm that specifically binds to a targetable conjugate that bears a therapeutic or diagnostic/detection agent. A variety of bispecific fusion proteins can be produced using molecular engineering. In one form, the bispecific fusion protein is monovalent, consisting of, for example, a scFv with a single binding site for one antigen and a Fab fragment with a single binding site for a second antigen. In another form, the bispecific fusion protein is divalent, consisting of, for example, an IgG with a binding site for one antigen and two scFv with two binding sites for a second antigen.

Preparation of Humanized and Human PAM4 Antibodies

Monoclonal antibodies for specific antigens may be obtained by methods known to those skilled in the art. See, for example, Kohler and Milstein, *Nature* 256: 495 (1975), and Coligan et al. (eds.), CURRENT PROTOCOLS IN IMMUNOLOGY, VOL. 1, pages 2.5.1-2.6.7 (John Wiley & Sons 1991) (hereinafter "Coligan"). Briefly, PAM4 MAbs can be obtained by injecting mice with a composition comprising the PAM4 antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to PAM4 antigen, culturing the clones that produce antibodies to PAM4 antigen, and isolating PAM4 antibodies from the hybridoma cultures. The PAM4 antibodies of the present invention bind the PAM4 antigen, a domain located between the amino terminus and the start of the repeat domain of MUC 1. The PAM4 antibodies of the present invention preferentially bind pancreatic cancer cells.

After the initial raising of antibodies to the immunogen, the antibodies can be sequenced and subsequently prepared by recombinant techniques. Humanization of murine antibodies and antibody fragments is well known to those skilled in the art. For example, humanized monoclonal antibodies are produced by transferring murine complementary determining regions from heavy and light variable chains of the mouse immunoglobulin into a human variable domain, and then, substituting human residues in the framework regions of the murine counterparts. The use of antibody components derived from humanized monoclonal antibodies obviates potential problems associated with the immunogenicity of murine constant regions.

A fully human antibody of the present invention, i.e., human PAM4 can be obtained from a transgenic non-human animal. See, e.g., Mendez et al., *Nature Genetics*, 15: 146-156 (1997); U.S. Pat. No. 5,633,425, which are incorporated in their entirety by reference. For example, a human antibody can be recovered from a transgenic mouse possessing human immunoglobulin loci. The mouse humoral immune system is humanized by inactivating the endogenous immunoglobulin genes and introducing human immunoglobulin loci. The human immunoglobulin loci are exceedingly complex and comprise a large number of discrete segments which together occupy almost 0.2% of the human genome. To ensure that transgenic mice are capable of producing adequate repertoires of antibodies, large portions of human heavy- and light-chain loci must be introduced into the mouse genome. This is accomplished in a stepwise process beginning with the formation of yeast artificial chromosomes (YACs) containing either human heavy- or light-chain immunoglobulin loci in germline configuration. Since each insert is approximately 1 Mb in size, YAC construction requires homologous recombination of overlapping fragments of the immunoglobulin loci. The two YACs, one containing the heavy-chain loci and one containing the light-chain loci, are introduced separately into mice via fusion of YAC-containing yeast spheroblasts with mouse embryonic stem cells. Embryonic stem cell clones are then microinjected into mouse blastocysts. Resulting chimeric males are screened for their ability to transmit the YAC through their germline and are bred with mice deficient in murine antibody production. Breeding the two transgenic strains, one containing the human heavy-chain loci and the other containing the human light-chain loci, creates progeny which produce human antibodies in response to immunization.

General techniques for cloning murine immunoglobulin variable domains are described, for example, by the publication of Orlandi et al., *Proc. Nat'l Acad. Sci. USA* 86: 3833 (1989), which is incorporated by reference in its entirety. Techniques for producing humanized MAbs are described, for example, by Carter et al., *Proc. Nat'l Acad. Sci. USA* 89: 4285 (1992), Singer et al., *J. Immun.* 150: 2844 (1992), Mountain et al. *Biotechnol. Genet. Eng. Rev.* 10: 1 (1992), and Coligan at pages 10.19.1-10.19.11, each of which is hereby incorporated by reference.

In general, the $V_\kappa$ (variable light chain) and $V_H$ (variable heavy chain) sequences for PAM4 antibodies can be obtained by a variety of molecular cloning procedures, such as RT-PCR, 5'-RACE, and cDNA library screening. Specifically, the $V_H$ and $V_\kappa$ genes of the MAb PAM4 were cloned by PCR amplification from the hybridoma cells by RT-PCR and 5' RACE, respectively, and their sequences determined by DNA sequencing. To confirm their authenticity, the cloned $V_L$ and $V_H$ genes can be expressed in cell culture as an Ab as described by Orlandi et al., (*Proc. Natl. Acad. Sci., USA,* 86: 3833 (1989)) which is incorporated by reference. Based on the V gene sequences, a humanized PAM4 antibody can then be designed and constructed as described by Leung et al. (*Mol. Immunol.,* 32: 1413 (1995)), which is incorporated by reference. cDNA can be prepared from any known hybridoma line or transfected cell line producing a murine or humanized PAM4 antibody by general molecular cloning techniques (Sambrook et al., Molecular Cloning, A laboratory manual, $2^{nd}$ Ed (1989)). Example 7 describes the humanization process utilized for hPAM4 MAb.

Antibodies can generally be isolated from cell culture media as follows. Transfectoma cultures are adapted to serum-free medium. For production of humanized antibody, cells are grown as a 500 ml culture in roller bottles using HSFM. Cultures are centrifuged and the supernatant filtered through a 0.2µ membrane. The filtered medium is passed through a protein A column (1×3 cm) at a flow rate of 1 ml/min. The resin is then washed with about 10 column volumes of PBS and protein A-bound antibody is eluted from the column with 0.1 M glycine buffer (pH 3.5) containing 10 mM EDTA. Fractions of 1.0 ml are collected in tubes containing 10 µl of 3 M Tris (pH 8.6), and protein concentrations determined from the absorbance at 280/260 nm. Peak fractions are pooled, dialyzed against PBS, and the antibody concentrated, for example, with the Centricon 30 (Amicon, Beverly, Mass.). The antibody concentration is determined by ELISA, as before, and its concentration adjusted to about 1 mg/ml using PBS. Sodium azide, 0.01% (w/v), is conveniently added to the sample as preservative.

The nucleotide sequences of the primers used to prepare the PAM4 antibodies are discussed in Example 7, below. In a preferred embodiment, a humanized PAM4 antibody or antibody fragment comprises the complementarity-determining regions (CDRs) of a murine PAM4 MAb and the framework (FR) regions of the light and heavy chain variable regions of a human antibody and the light and heavy chain constant regions of a human antibody, wherein the CDRs of the light chain variable region of the humanized PAM4 comprises CDR1 comprising an amino acid sequence of SASSSVSSSYLY (SEQ ID NO: 1); CDR2 comprising an amino acid sequence of STSNLAS (SEQ ID NO: 2); and CDR3 comprising an amino acid sequence of HQWNRYPYT (SEQ ID NO: 3); and the CDRs of the heavy chain variable region of the humanized PAM4 MAb comprises CDR1 comprising an amino acid sequence of SYVLH (SEQ ID NO: 4); CDR2 comprising an amino acid sequence of YINPYNDGTQYNEKFKG (SEQ ID NO: 5) and CDR3 comprising an amino acid sequence of GFGGSYGFAY (SEQ ID NO: 6). Also preferred, the FRs of the light and heavy chain variable regions of the humanized antibody comprise at least one amino acid substituted from said corresponding FRs of the murine PAM4 MAb.

PAM4 MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

PAM4 MAbs can be characterized by a variety of techniques that are well-known to those of skill in the art. For example, the ability of a PAM4 MAb to bind to the PAM4 antigen can be verified using an indirect enzyme immunoassay, flow cytometry analysis, or Western analysis.

Production of PAM4 Antibody Fragments

The present invention contemplates the use PAM4 antibody fragments. Antibody fragments which recognize specific epitopes can be generated by known techniques. The antibody fragments are antigen binding portions of an antibody, such as F(ab')$_2$, Fab', Fab, Fv, sFv and the like. F(ab')$_2$ fragments, for example, can be produced by pepsin digestion of the antibody molecule and Fab' fragments can be generated by reducing disulfide bridges of the F(ab')$_2$ fragments. These methods are described, for example, by Goldenberg, U.S. Pat. Nos. 4,036,945 and 4,331,647 and references contained therein, which patents are incorporated herein in their entireties by reference. Also, see Nisonoff et al., *Arch Biochem. Biophys.* 89: 230 (1960); Porter, *Biochem. J.* 73: 119 (1959), Edelman et al., in METHODS IN ENZYMOLOGY VOL. 1, page 422 (Academic Press 1967), and Coligan at pages 2.8.1-2.8.10 and 2.10.-2.10.4. Alternatively, Fab' expression libraries can be constructed (Huse et al., 1989, *Science,* 246:1274-1281) to allow rapid and easy identification of monoclonal Fab' fragments with the desired specificity. The present invention encompasses antibodies and antibody fragments.

A single chain Fv molecule (scFv) comprises a $V_L$ domain and a $V_H$ domain. The $V_L$ and $V_H$ domains associate to form a target binding site. These two domains are further covalently linked by a peptide linker (L). A scFv molecule is denoted as either $V_L$-L-$V_H$ if the $V_L$ domain is the N-terminal part of the scFv molecule, or as $V_H$-L-$V_L$ if the $V_H$ domain is the N-terminal part of the scFv molecule. Methods for making scFv molecules and designing suitable peptide linkers are described in U.S. Pat. No. 4,704,692, U.S. Pat. No. 4,946,778, R. Raag and M. Whitlow, "*Single Chain Fvs.*" FASEB Vol 9:73-80 (1995) and R. E. Bird and B. W. Walker, "Single Chain Antibody Variable Regions," TIBTECH, Vol 9: 132-137 (1991). These references are incorporated herein by reference.

An antibody fragment can be prepared by proteolytic hydrolysis of the full-length antibody or by expression in *E. coli* or another host of the DNA coding for the fragment. An antibody fragment can be obtained by pepsin or papain digestion of full-length antibodies by conventional methods. For example, an antibody fragment can be produced by enzymatic cleavage of antibodies with pepsin to provide an approximate 100 Kd fragment denoted $F(ab')_2$. This fragment can be further cleaved using a thiol reducing agent, and optionally a blocking group for the sulfhydryl groups resulting from cleavage of disulfide linkages, to produce an approximate 50 Kd Fab' monovalent fragment. Alternatively, an enzymatic cleavage using papain produces two monovalent Fab fragments and an Fc fragment directly. These methods are described, for example, by Goldenberg, U.S. Pat. Nos. 4,036,945 and 4,331,647 and references contained therein, which patents are incorporated herein in their entireties by reference. Also, see Nisonoff et al., *Arch Biochem. Biophys.* 89: 230 (1960); Porter, *Biochem. J.* 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

Another form of an antibody fragment is a peptide coding for a single complementarity-determining region (CDR). A CDR is a segment of the variable region of an antibody that is complementary in structure to the epitope to which the antibody binds and is more variable than the rest of the variable region. Accordingly, a CDR is sometimes referred to as hypervariable region. A variable region comprises three CDRs. CDR peptides can be obtained by constructing genes encoding the CDR of an antibody of interest. Such genes are prepared, for example, by using the polymerase chain reaction (PCR) to synthesize the variable region from RNA of antibody-producing cells. See, for example, Larrick et al., *Methods: A Companion to Methods in Enzymology* 2: 106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995).

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

Production of Humanized and Human PAM4 Antibody Fusion Proteins

The antibody fusion proteins of the present invention can be prepared by a variety of conventional procedures, ranging from glutaraldehyde linkage to more specific linkages between functional groups. The antibodies and/or antibody fragments that comprise the fusion proteins described herein are preferably covalently bound to one another, directly or through a linker moiety, through one or more functional groups on the antibody or fragment, e.g., amine, carboxyl, phenyl, thiol, or hydroxyl groups. Various conventional linkers in addition to glutaraldehyde can be used, e.g., diisocyanates, diiosothiocyanates, bis(hydroxysuccinimide) esters, carbodiimides, maleimidehydroxysuccinimide esters, and the like.

A simple method for producing humanized and human PAM4 fusion proteins is to mix the antibodies or fragments in the presence of glutaraldehyde. The initial Schiff base linkages can be stabilized, e.g., by borohydride reduction to secondary amines. A diiosothiocyanate or carbodiimide can be used in place of glutaraldehyde as a non-site-specific linker. In one embodiment of the present invention, an antibody fusion protein comprises one humanized or human PAM4 MAb, or fragment thereof, wherein the MAb binds to the domain located between the amino terminus and the start of the repeat domain of the MUC1 antigen. This fusion protein and fragments thereof preferentially bind pancreatic cancer cells. This monovalent, monospecific MAb is useful for direct targeting of an antigen, where the MAb is attached to a therapeutic agent, a diagnostic/detection agent, or a combination thereof, and the protein is administered directly to a patient in need thereof.

The PAM4 antibody fusion proteins and fragments thereof of the present invention may instead comprise at least two humanized or human PAM4 MAbs, or fragments thereof, wherein at least two of the MAbs or fragments thereof bind to distinct epitopes of the PAM4 antigen. For example, the MAbs can produce antigen specific diabodies, triabodies and tetrabodies, which are multivalent but monospecific to the PAM4 antigen. The non-covalent association of two or more scFv molecules can form functional diabodies, triabodies and tetrabodies. Monospecific diabodies are homodimers of the same scFv, where each scFv comprises the $V_H$ domain from the selected antibody connected by a short linker to the $V_L$ domain of the same antibody. A diabody is a bivalent dimer formed by the non-covalent association of two scFvs, yielding two Fv binding sites. A triabody results from the formation of a trivalent trimer of three scFvs, yielding three binding sites, and a tetrabody is a tetravalent tetramer of four scFvs, resulting in four binding sites. Several monospecific diabodies have been made using an expression vector that contains a recombinant gene construct comprising $V_{H1}$-linker-$V_{L1}$. See Holliger et al., *Proc. Natl. Acad. Sci. USA* 90: 6444-6448 (1993); Atwell et al., *Molecular Immunology* 33: 1301-1302 (1996); Holliger et al., *Nature Biotechnology* 15: 632-631(1997); Helfrich et al., *Int. J. Cancer* 76: 232-239 (1998); Kipriyanov et al., *Int. J. Cancer* 77: 763-772 (1998); Holiger et al., *Cancer Research* 59: 2909-2916(1999)). Methods of constructing scFvs are disclosed in U.S. Pat. No. 4,946,778 (1990) and U.S. Pat. No. 5,132,405 (1992). Methods of producing multivalent, monospecific antibodies based on scFv are disclosed in U.S. Pat. No. 5,837,242 (1998), U.S. Pat. No. 5,844,094 (1998) and WO-98/44001 (1998). The multivalent, monospecific antibody fusion protein binds to two or more of the same type of epitopes that can be situated on the same antigen or on separate antigens. The increased valency allows for additional interaction, increased affinity, and longer residence times. These antibody fusion proteins can be utilized in direct targeting systems, where the antibody fusion protein is conjugated to a therapeutic agent, a diagnostic/detection agent, or a combination thereof, and administered directly to a patient in need thereof.

A preferred embodiment of the instant invention is a multivalent, multispecific antibody or fragment thereof comprising more than one antigen binding site having an affinity toward a PAM4 target epitope and one or more additional epitopes associated with pancreatic cancer antigens. This fusion protein is multispecific because it binds at least two different epitopes, which can reside on the same or different antigens. For example, the fusion protein may comprise more than one antigen binding site, the first with an affinity toward one PAM4 antigen epitope and the second with an affinity toward another target antigen such as TAG-72 or CEA. Another example is a bispecific PAM4 antibody fusion protein which may comprise a CA19.9 MAb (or fragment thereof) and a PAM4 MAb (or fragment thereof). Such a fusion protein will have an affinity toward CA19.9 as well as the domain located between the amino terminus and start of the repeat domain of MUC1. Also contemplated in the present invention is a fusion protein comprising more than one antigen binding site having an affinity for at least two different PAM4 antigen epitopes.

The antibody fusion proteins and fragments thereof of the present invention can be utilized in direct targeting systems, where the antibody fusion protein is conjugated to a therapeutic agent, a diagnostic/detection agent, or a combination thereof, and administered directly to a patient in need thereof.

Another preferred embodiment of the instant invention is a multivalent, multispecific antibodies and fragments thereof comprising more than one antigen binding site having affinity toward a PAM4 target epitope and at least one hapten binding site having affinity towards hapten molecules. For example, a bispecific PAM4 antibody fusion protein may comprise the 679 MAb (or fragment thereof) and the PAM4 MAb (or fragment thereof). The monoclonal antibody, 679, binds with high affinity to molecules containing the tripeptide moiety histamine succinyl glycyl (HSG). Such a bispecific PAM4 antibody fusion protein can be prepared, for example, by obtaining an F(ab')$_2$ fragment from 679, as described above. The interchain disulfide bridges of the 679 F(ab')$_2$ fragment are gently reduced with cystine, taking care to avoid light-heavy chain linkage, to form Fab'-SH fragments. The SH group(s) is (are) activated with an excess of bis-maleimide linker (1,1'-(methylenedi-4,1-phenylene)bis-malemide). The PAM4 MAb is converted to Fab'-SH and then reacted with the activated MR23 Fab'-SH fragment to obtain a bispecific PAM4 antibody fusion protein. Bispecific antibody fusion proteins such as this one can be utilized in affinity enhancing systems, where the target antigen is pretargeted with the fusion protein and is subsequently targeted with a diagnostic or therapeutic agent that binds with the antibody-antigen complex formed by pretargeting.

Bispecific antibodies can be made by a variety of conventional methods, e.g., disulfide cleavage and reformation of mixtures of whole IgG or, preferably F(ab')$_2$ fragments, fusions of more than one hybridoma to form polyomas that produce antibodies having more than one specificity, and by genetic engineering. Bispecific antibody fusion proteins have been prepared by oxidative cleavage of Fab' fragments resulting from reductive cleavage of different antibodies. This is advantageously carried out by mixing two different F(ab')$_2$ fragments produced by pepsin digestion of two different antibodies, reductive cleavage to form a mixture of Fab' fragments, followed by oxidative reformation of the disulfide linkages to produce a mixture of F(ab')$_2$ fragments including bispecific antibody fusion proteins containing a Fab' potion specific to each of the original epitopes. General techniques for the preparation of antibody fusion proteins may be found, for example, in Nisonoff et al., *Arch Biochem. Biophys.* 93: 470 (1961), Hämmerling et al., *J. Exp. Med.* 128: 1461 (1968), and U.S. Pat. No. 4,331,647. Contemplated in the present invention is an antibody fusion protein or fragment thereof comprising at least one first PAM4 MAb or fragment thereof and at least one second MAb or fragment thereof, other than the PAM4 MAbs or fragments thereof of the present invention.

More selective linkage can be achieved by using a heterobifunctional linker such as maleimidehydroxysuccinimide ester. Reaction of the ester with an antibody or fragment will derivatize amine groups on the antibody or fragment, and the derivative can then be reacted with, e.g., and antibody Fab fragment having free sulfhydryl groups (or, a larger fragment or intact antibody with sulfhydryl groups appended thereto by, e.g., Traut's Reagent). Such a linker is less likely to crosslink groups in the same antibody and improves the selectivity of the linkage.

It is advantageous to link the antibodies or fragments at sites remote from the antigen binding sites. This can be accomplished by, e.g., linkage to cleaved interchain sulfydryl groups, as noted above. Another method involves reacting an antibody having an oxidized carbohydrate portion with another antibody that has at lease one free amine function. This results in an initial Schiff base (mime) linkage, which is preferably stabilized by reduction to a secondary amine, e.g., by borohydride reduction, to form the final composite. Such site-specific linkages are disclosed, for small molecules, in U.S. Pat. No. 4,671,958, and for larger addends in U.S. Pat. No. 4,699,784—incorporated by reference.

A polyspecific PAM4 antibody fusion protein can be obtained by adding PAM4 antigen binding moieties to a bispecific humanized or human PAM4 antibody fusion protein. For example, a bispecific antibody fusion protein can be reacted with 2-iminothiolane to introduce one or more sulfhydryl groups for use in coupling the bispecific fusion protein to a third PAM4 MAb or fragment, using the bis-maleimide activation procedure described above. These techniques for producing antibody fusion proteins are well known to those of skill in the art. See, for example, U.S. Pat. No. 4,925,648, which is incorporated by reference in its entirety.

ScFvs with linkers greater than 12 amino acid residues in length (for example, 15- or 18-residue linkers) allow interacting between the $V_H$ and $V_L$ domains on the same chain and generally form a mixture of monomers, dimers (termed diabodies) and small amounts of higher mass multimers, (Kortt et al., Eur. J. Biochem. (1994) 221: 151-157). ScFvs with linkers of 5 or less amino acid residues, however, prohibit intramolecular pairing of the $V_H$ and $V_L$ domains on the same chain, forcing pairing with $V_H$ and $V_L$ domains on a different chain. Linkers between 3- and 12-residues form predominantly dimers (Atwell et al., Protein Engineering (1999) 12: 597-604). With linkers between 0 and 2 residues, trimeric (termed triabodies), tetrameric (termed tetrabodies) or higher oligomeric structures of scFvs are formed; however, the exact patterns of oligomerization appear to depend on the composition as well as the orientation of the V-domains, in addition to the linker length. For example, scFvs of the anti-neuraminidase antibody NC10 formed predominantly trimers ($V_H$ to $V_L$ orientation) or tetramers ($V_L$ to $V_H$ orientation) with 0-residue linkers (Dolezal et al., Protein Engineering (2000) 13: 565-574). For scFvs constructed from NC10 with 1- and 2-residue linkers, the $V_H$ to $V_L$ orientation formed predominantly diabodies (Atwell et al., Protein Engineering (1999) 12: 597-604); in contrast, the $V_L$ to $V_H$ orientation formed a mixture of tetramers, trimers, dimers, and higher mass multimers (Dolezal et al., Protein Engineering (2000) 13: 565-574). For scFvs constructed from the anti-CD19 antibody HD37 in the $V_H$ to $V_L$ orientation, the 0-residue linker formed exclusively trimers and the 1-residue linker formed exclusively tetramers (Le Gall et al., FEBS Letters (1999) 453: 164-168).

Expression Vectors and Host Cells

An expression vector is a DNA molecule comprising a gene that is expressed in a host cell. Typically, gene expression is placed under the control of certain regulatory elements, including constitutive or inducible promoters, tissue-specific regulatory elements, and enhancers. Such a gene is said to be "operably linked to" the regulatory elements. A promoter is a DNA sequence that directs the transcription of a structural gene. A structural gene is a DNA sequence that is transcribed into messenger RNA (mRNA) which is then translated into a sequence of amino acids characteristic of a specific polypeptide. Typically, a promoter is located in the 5' region of a gene, proximal to the transcriptional start site of a structural gene. If a promoter is an inducible promoter, then the rate of transcription increases in response to an inducing agent. In contrast, the rate of transcription is not regulated by an inducing agent if the promoter is a constitutive promoter. An enhancer is a DNA regulatory element that can increase the efficiency of transcription, regardless of the distance or orientation of the enhancer relative to the start site of transcription.

An isolated DNA molecule is a fragment of DNA that is not integrated in the genomic DNA of an organism. For example, a cloned PAM4 antigen gene is a DNA fragment that has been separated from the genomic DNA of a mammalian cell. Another example of an isolated DNA molecule is a chemically-synthesized DNA molecule that is not integrated in the genomic DNA of an organism. Complementary DNA (cDNA) is a single-stranded DNA molecule that is formed from an mRNA template by the enzyme reverse transcriptase. Typically, a short synthetic oligo nucleotide complementary to a portion of the mRNA is employed as a primer for the initiation of reverse transcription to generate the first stand DNA. Those skilled in the art also use the term "cDNA" to refer to a double-stranded DNA molecule consisting of such a single-stranded DNA molecule and its complementary DNA strand.

A cloning vector is a DNA molecule, such as a plasmid, cosmid, or bacteriophage, that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide tetracycline resistance or ampicillin resistance. A recombinant host may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell. The term expression refers to the biosynthesis of a gene product. For example, in the case of a structural gene, expression involves transcription of the structural gene into mRNA and the translation of mRNA into one or more polypeptides.

Suitable host cells include microbial or mammalian host cells. A preferred host is the human cell line, PER.C6, which was developed for production of MAbs, and other fusion proteins. Accordingly, a preferred embodiment of the present invention is a host cell comprising a DNA sequence encoding the PAM4 MAb, conjugate, fusion protein or fragments thereof. PER.C6 cells (WO 97/00326) were generated by transfection of primary human embryonic retina cells, using a plasmid that contained the Adserotype 5 (Ad5) E1A- and E1B-coding sequences (Ad5 nucleotides 459-3510) under the control of the human phosphoglycerate kinase (PGK) promoter. E1A and E1B are adenovirus early gene activation protein 1A and 1B, respectively. The methods and compositions are particularly useful for generating stable expression of human recombinant proteins of interest that are modified post-translationally, e.g. by glycosylation. Several features make PER.C6 particularly useful as a host for recombinant protein production, such as PER.C6 is a fully characterized human cell line and it was developed in compliance with good laboratory practices. Moreover, PER.C6 can be grown as a suspension culture in defined serum-free medium devoid of any human- or animal-derived proteins and its growth is compatible with roller bottles, shaker flasks, spinner flasks and bioreactors with doubling times of about 35 hours. Finally, the presence of E1A causes an up regulation of expression of genes that are under the control of the CMV enhancer/promoter and the presence of E13 prevents p53-dependent apoptosis possibly enhanced through over expression of the recombinant transgene. In one embodiment, the cell is capable of producing 2 to 200-fold more recombinant protein and/or proteinaceous substance than conventional mammalian cell lines.

Humanized and Human PAM4 Antibodies Use for Treatment and Diagnosis

Contemplated in the present invention is a method of diagnosing or treating a malignancy in a subject comprising administering to the subject a therapeutically effective amount of a therapeutic conjugate comprising a PAM4 MAb or fragment thereof or an antibody fusion protein or fragment thereof, wherein the PAM4 MAb or fragment thereof or antibody fusion protein or fragment thereof is bound to at least one diagnostic and/or therapeutic agent and then formulated in a pharmaceutically suitable excipient. Also preferred is a method for diagnosing or treating cancer, comprising: administering a multivalent, multispecific antibody or fragment thereof comprising one or more antigen binding sites toward a PAM4 antigen and one or more hapten binding sites to a subject in need thereof, waiting a sufficient amount of time for an amount of the non-antibody to clear the subject's blood stream; and then administering to the subject a carrier molecule comprising a diagnostic/detection agent, a therapeutic agent, or a combination thereof, that binds to the binding site of the multivalent, multispecific antibody or fragment thereof. In a preferred embodiment, the cancer is a pancreatic cancer. In another preferred embodiment, the antibody is a multivalent, monospecific antibody or fragment thereof.

The use of MAbs for in vitro diagnosis is well-known. See, for example, Carlsson et al., *Bio/Technology* 7 (6): 567 (1989). For example, MAbs can be used to detect the presence of a tumor-associated antigen in tissue from biopsy samples. MAbs also can be used to measure the amount of tumor-associated antigen in clinical fluid samples using techniques such as radioimmunoassay, enzyme-linked immunosorbent assay, and fluorescence immunoassay.

Conjugates of tumor-targeted MAbs and toxins can be used to selectively kill cancer cells in vivo (Spalding, *Bio/Technology* 9(8): 701 (1991); Goldenberg, *Scientific American Science & Medicine* 1(1): 64 (1994)). For example, therapeutic studies in experimental animal models have demonstrated the anti-tumor activity of antibodies carrying cytotoxic radionuclides. See Example 3 and 5 for a discussion of animal models and therapeutic studies. (Goldenberg et al., *Cancer Res.* 41: 4354 (1981), Cheung et al., *J. Nat'l Cancer Inst.* 77: 739 (1986), and Senekowitsch et al., *J. Nucl. Med.* 30: 531 (1989)).

Humanized and fully human antibodies and fragments thereof are suitable for use in therapeutic methods and diagnostic methods. Accordingly, contemplated in the present invention is a method of delivering a diagnostic or therapeutic agent, or a combination thereof, to a target comprising (i) providing a composition that comprises a PAM4 antibody or fragment thereof conjugated to at least one diagnostic and/or therapeutic agent and (ii) administering to a subject in need thereof the diagnostic or therapeutic antibody conjugate. In a preferred embodiment, the PAM4 antibodies and fragments thereof are humanized or fully human. In another embodiment, the humanized and fully human PAM4 antibodies and fragments thereof of the present invention are used in methods for treating malignancies.

Also described herein is a cancer cell targeting diagnostic or therapeutic conjugate comprising an antibody component that comprises a PAM4 MAb or fragment thereof of any of the antibodies of the present invention, or an antibody fusion protein or fragment thereof, wherein the antibody component is bound to at least one diagnostic or at least one therapeutic agent. Preferably, the diagnostic conjugate is a photoactive diagnostic/detection agent, an ultrasound detectable agent or an MRI contrast agent. Still preferred, the diagnostic/detection agent is a radionuclide with an energy between 20 and 4,000 keV.

Another embodiment of the present invention is a method for diagnosing or treating a malignancy comprising administering a therapeutically or diagnostically effective amount of at least one naked PAM4 antibody or fragment thereof and/or PAM4 fusion protein or fragment therof, and optionally formulating the PAM4 antibody, fusion protein, or fragments thereof in a pharmaceutical excipient.

The compositions for treatment contain at least one humanized or fully human PAM4 antibody or fragment thereof either alone and unconjugated, or conjugated or unconjugated and in combination with other antibodies or fragments thereof, such as other humanized or chimeric antibodies, human antibodies, therapeutic agents or immunomodulators. Naked or conjugated antibodies to the same or different epitope or antigen may also be combined with one or more of the PAM4 antibodies or fragments thereof of the present invention.

Accordingly, the present invention contemplates the administration of PAM4 antibodies and fragments thereof, including PAM4 fusion proteins and fragments thereof, alone, as a naked antibody or antibody fragment, or administered as a multimodal therapy. Preferably, the antibody is a humanized or fully human PAM4 antibody or fragment thereof. Multimodal therapies of the present invention further include immunotherapy with a naked PAM4 antibody supplemented with administration of other antibodies in the form of naked antibodies, fusion proteins, or as immunoconjugates. For example, a humanized or fully human PAM4 antibody may be combined with another naked humanized PAM4 or other antibody, or a humanized PAM4, or other antibody conjugated to an isotope, one or more chemotherapeutic agents, cytokines, toxins or a combination thereof. For example, the present invention contemplates treatment of a naked or conjugated PAM4 antibody or fragments thereof before, in combination with, or after other pancreatic tumor associated antibodies such as CA19.9, DUPAN2, SPAN1, Nd2, B72.3, CC49, Ia3, aLe$^a$ antibodies, and other Lewis antigens (e.g., Le(y)), as well as antibodies against carcinoembryonic antigen (CEA), colon-specific antigen-p (CSAp), MUC1, MUC2, MUC3, MUC4, HER2/neu, EGFR, angiogenesis factors (e.g., VEGF), insulin-like growth factor (IGF), tenascin, platelet derived growth factor, and IL-6, as well as products of oncogenes and antibodies against tumor necrosis substances. These solid tumor antibodies may be naked or conjugated to, inter alia, drugs, toxins, isotopes, external radiation or immunomodulators. A fusion protein of a humanized or fully human PAM4 antibody and a toxin or may also be used in this invention. Many different antibody combinations may be constructed, either as naked antibodies or as partly naked and partly conjugated with a therapeutic agent or immunomodulator. Alternatively, different naked antibody combinations may be employed for administration in combination with other therapeutic agents, such as a cytotoxic drug or with radiation, given consecutively, simultaneously, or sequentially.

The monospecific antibodies described herein that are linked to diagnostic or therapeutic agents directly target PAM4 positive tumors. The monospecific molecules bind selectively to targeted antigens and as the number of binding sites on the molecule increases, the affinity for the target cell increases and a longer residence time is observed at the desired location. Moreover, non-antigen bound molecules are cleared from the body quickly and exposure of normal tissues is minimized. A use of multispecific antibodies is in AES systems, where PAM4 pre-targets positive tumors for subsequent specific delivery of diagnostic or therapeutic agents. The agents are carried by histamine succinyl glycyl (HSG) containing peptides. The murine monoclonal antibody designated 679 (an IgG1, K) binds with high affinity to molecules containing the tri-peptide moiety, HSG (Morel et al, Molecular Immunology, 27, 995-1000, 1990). 679 MAb can form a bispecific antibody with hPAM4 that binds with HSG and the target antigen. Alternative haptens may also be utilized. These antibodies bind selectively to targeted antigens allowing for increased affinity and a longer residence time at the desired location. Moreover, non-antigen bound diabodies are cleared from the body quickly and exposure of normal tissues is minimized. PAM4 antibodies and fragments thereof and conjugates can be used to diagnose and treat mammalian disorders such as cancer.

Delivering a diagnostic or a therapeutic agent to a target for diagnosis or treatment in accordance with the invention includes providing the PAM4 antibody or fragments thereof with a diagnostic or therapeutic agent and administering to a subject in need thereof with the antibody. Diagnosis further requires the step of detecting the bound proteins with known techniques.

In the context of this application, the terms "diagnosis" or "detection" can be used interchangeably. Whereas diagnosis usually refers to defining a tissue's specific histological status, detection recognizes and locates a tissue, lesion or organism containing a particular antigen.

Administration of the antibodies and their fragments of the present invention with diagnostic or therapeutic agents can be effected in a mammal by intravenous, intraarterial, intraperitoneal, intramuscular, subcutaneous, intrapleural, intrathecal, perfusion through a regional catheter, or direct intralesional injection. When administering the antibody by injection, the administration may be by continuous infusion or by single or multiple boluses.

The antibody with the diagnostic or therapeutic agent may be provided as a kit for human or mammalian therapeutic and diagnostic use in a pharmaceutically acceptable injection vehicle, preferably phosphate-buffered saline (PBS) at physiological pH and concentration. The preparation preferably will be sterile, especially if it is intended for use in humans. Optional components of such kits include stabilizers, buffers, labeling reagents, radioisotopes, paramagnetic compounds, second antibody for enhanced clearance, and conventional syringes, columns, vials and the like.

Naked Antibody Therapy

A therapeutically effective amount of a naked humanized and fully human PAM4 antibody, or fragments thereof, or PAM4 fusion proteins or fragments thereof, can be formulated in a pharmaceutically acceptable excipient. The efficacy of the naked humanized and fully human PAM4 antibodies and their fragments can also be enhanced by supplementing these naked antibodies with one or more other naked antibodies, with one or more immunoconjugates of humanized and fully human PAM4 antibodies, conjugated with one or more therapeutic agents, including drugs, toxins, immunomodulators, hormones, oligonucleotides, hormone antagonists, enzymes, enzyme inhibitors, therapeutic radionuclides, an angiogenesis inhibitor, etc., administered concurrently or sequentially or according to a prescribed dosing regimen, with the PAM4 antibodies or fragments thereof. The naked antibodies that may supplement the naked PAM4 antibodies and fragments thereof may be directed against either the same tumor type or against immunomodulator cells (e.g., $CD40^+$ cells) that can be recruited to enhance the antitumor effects of the naked antibodies of choice.

PAM4 Immunoconjugates

The present invention also contemplates the use of humanized and human PAM4 antibodies and fragments thereof conjugated to at least one therapeutic and/or diagnostic/detection agent for therapy or diagnosis. For immunotherapy, the objective is to deliver cytotoxic doses of radioactivity, toxin, or drug to target cells, while minimizing exposure to non-target tissues. The PAM4 antibodies of the present invention can be used to diagnose and treat pancreatic tumors.

Any of the antibodies, antibody fusion proteins, and fragments thereof of the present invention can be conjugated with one or more therapeutic or diagnostic/detection agents. Generally, one therapeutic or diagnostic/detection agent is attached to each antibody, fusion protein or fragment thereof but more than one therapeutic agent and/or diagnostic/detection agent can be attached to the same antibody or antibody fragment. If the Fc region is absent (for example when the antibody used as the antibody component of the immunoconjugate is an antibody fragment), it is possible to introduce a carbohydrate moiety into the light chain variable region of a full length antibody or antibody fragment. See, for example, Leung et al., *J. Immunol.* 154: 5919 (1995); Hansen et al., U.S. Pat. No. 5,443,953 (1995), Leung et al., U.S. Pat. No. 6,254,868, all of which are incorporated in their entirety by reference. The engineered carbohydrate moiety is used to attach the therapeutic or diagnostic/detection agent.

Methods for conjugating peptides to antibody components via an antibody carbohydrate moiety are well-known to those of skill in the art. See, for example, Shih et al., *Int. J. Cancer* 41: 832 (1988); Shih et al., *Int. J. Cancer* 46: 1101 (1990); and Shih et al., U.S. Pat. No. 5,057,313, all of which are incorporated in their entirety by reference. The general method involves reacting an antibody component having an oxidized carbohydrate portion with a carrier polymer that has at least one free amine function and that is loaded with a plurality of peptide. This reaction results in an initial Schiff base (imine) linkage, which can be stabilized by reduction to a secondary amine to form the final conjugate.

The antibody fusion proteins and fragments thereof of the present invention comprise two or more antibodies or fragments thereof and each of the antibodies that compose this fusion protein can contain at least one therapeutic agent and/or diagnostic/detection agent. For example, an antibody fusion protein may comprise one antibody (two antigen binding sites) and an antibody fragment, two antibody fragments, or two antibodies. The antibody fusion protien may then be conjugated to at least one diagnostic/detection and/or therapeutic agent.

Accordingly, one or more of the antibodies or fragments thereof of the antibody fusion protein can have more than one therapeutic and/or diagnostic/detection agent attached. Further, the therapeutic agents do not need to be the same but can be different therapeutic agents, for example, one can attach a drug and a radioisotope to the same fusion protein. Particularly, an IgG can be radiolabeled with $^{131}I$ and attached to a drug. The $^{131}I$ can be incorporated into the tyrosine of the IgG and the drug attached to the epsilon amino group of the IgG lysines. Both therapeutic and diagnostic/detection agents also can be attached to reduced SH groups and to the carbohydrate side chains.

A wide variety of diagnostic and therapeutic reagents can be administered concurrently or sequentially, or advantageously conjugated to the antibodies of the invention, for example, drugs, toxins, oligonucleotides, immunomodulators, hormones, hormone antagonists, enzymes, enzyme inhibitors, therapeutic radionuclides, an angiogenesis inhibitor, etc. The therapeutic agents recited here are those agents that also are useful for administration separately with the naked antibody as described above. Therapeutic agents include, for example, chemotherapeutic drugs such as vinca alkaloids, anthracyclines, gemcitabine, epidophyllotoxins, taxanes, antimetabolites, alkylating agents, antibiotics, SN-38, COX-2 inhibitors, antimitotics, antiangiogenic and apoptotoic agents, particularly doxorubicin, methotrexate, taxol, CPT-11, camptothecans, and others from these and other classes of anticancer agents, and the like. Other useful cancer chemotherapeutic drugs for administering concurrently or sequentially, or for the preparation of immunoconjugates and antibody fusion proteins include nitrogen mustards, alkyl sulfonates, nitrosoureas, triazenes, folic acid analogs, COX-2 inhibitors, pyrimidine analogs, purine analogs, platinum coordination complexes, hormones, and the like. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art.

In one embodiment, the humanized PAM4 antibodies and fragments thereof of the present invention is conjugated to gemcitabine. In another embodiment, gemcitabine is given before, after, or concurrently with a naked or conjugated humanized PAM4 antibody or fragment thereof of the present invention. Preferably, the conjugated humanized PAM4 antibody or antibody fragment is conjugated to a radionuclide.

A toxin can be of animal, plant or microbial origin. A toxin, such as *Pseudomonas* exotoxin, may also be complexed to or form the therapeutic agent portion of an immunoconjugate of the PAM4 and hPAM4 antibodies of the present invention. Other toxins suitably employed in the preparation of such conjugates or other fusion proteins, include ricin, abrin, ribonuclease (RNase), DNase I, *Staphy-* lococcal enterotoxin-A, pokeweed antiviral protein, gelonin, diphtherin toxin, *Pseudomonas* exotoxin, and *Pseudomonas* endotoxin. See, for example, Pastan et al., *Cell* 47:641 (1986), and Goldenberg, *CA—A Cancer Journal for Clinicians* 44:43 (1994). Additional toxins suitable for use in the present invention are known to those of skill in the art and are disclosed in U.S. Pat. No. 6,077,499, which is incorporated in its entirety by reference.

An immunomodulator, such as a cytokine, may also be conjugated to, or form the therapeutic agent portion of the PAM4 and hPAM4 immunoconjugate, or may be administered with, but unconjugated to, the humanized or human PAM4 antibody or fragment thereof, or PAM4 fusion protein or fragment thereof of the present invention. The PAM4 fusion protein or fragment thereof may comprise one or more antibodies or fragments thereof binding to different antigens. For example, the fusion protein may bind the PAM4 antigen as well as immunomodulating cells or factors. Alternatively, subjects can receive a naked PAM4 antibody, fusion protein, or fragment thereof and a separately administered cytokine, which can be administered before, concurrently or after administration of the naked PAM4 antibodies. As used herein, the term "immunomodulator" includes cytokines, stem cell growth factors, lymphotoxins, such as tumor necrosis factor (TNF), and hematopoietic factors, such as interleukins (e.g., interleukin-1 (IL-1), IL-2, IL-3, IL-6, IL-10, IL-12 and IL-18, IL-21), colony stimulating factors (e.g., granulocyte-colony stimulating factor (G-CSF) and granulocyte macrophage-colony stimulating factor (GM-CSF)), interferons (e.g., interferons-α, -β and -γ), the stem cell growth factor designated "S1 factor," erythropoietin and thrombopoietin. Examples of suitable immunomodulator moieties include IL-2, IL-6, IL-10, IL-12, IL-18, IL-21, interferon-γ, TNF-α, and the like.

Alternatively, the antibodies and fragments of the present invention can be detectably labeled by linking the antibody to an enzyme. When the antibody-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label antibody include malate dehydrogenase, staphylococcal nuclease, delta-V-steroid isomerase, yeast alcohol dehydrogenase, α-glycerophosphate dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase and acetylcholinesterase.

A therapeutic or diagnostic/detection agent can be attached at the hinge region of a reduced antibody component via disulfide bond formation. As an alternative, such agents can be attached to the antibody component using a heterobifunctional cross-linker, such as N-succinyl 3-(2-pyridyldithio)proprionate (SPDP). Yu et al., *Int. J. Cancer* 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the therapeutic or diagnostic/detection agent can be conjugated via a carbohydrate moiety in the Fc region of the antibody. The carbohydrate group can be used to increase the loading of the same agent that is bound to a thiol group, or the carbohydrate moiety can be used to bind a different peptide.

In the methods of the invention, the targetable construct may comprise one or more radioactive isotopes useful for detecting diseased tissue. Particularly useful diagnostic radionuclides include, but are not limited to, $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94}$mTc, $^{94}$Tc, $^{99}$mTc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, or other gamma-, beta-, or positron-emitters, preferably with a decay energy in the range of 20 to 4,000 keV, more preferably in the range of 25 to 4,000 keV, and even more preferably in the range of 25 to 1,000 keV, and still more preferably in the range of 70 to 700 keV. Total decay energies of useful positron-emitting radionuclides are preferably <2,000 keV, more preferably under 1,000 keV, and most preferably <700 keV. Radionuclides useful as diagnostic/detection agents utilizing gamma-ray detection include, but are not limited to: $^{51}$Cr, $^{57}$Co, $^{58}$Co, $^{59}$Fe, $^{67}$Cu, $^{67}$Ga, $^{75}$Se, $^{97}$Ru, $^{99m}$Tc, $^{111}$In, $^{114m}$In, $^{123}$I, $^{125}$I, $^{131}$I, $^{169}$Yb, $^{197}$Hg, and $^{201}$Tl. Decay energies of useful gamma-ray emitting radionuclides are preferably 20-2000 keV, more preferably 60-600 keV, and most preferably 100-300 keV.

In the methods of the invention, the targetable construct may comprise one or more radioactive isotopes useful for treating diseased tissue. Particularly useful therapeutic radionuclides include, but are not limited to $^{111}$In, $^{177}$Lu, $^{212}$Bi, $^{213}$Bi, $^{211}$At, $^{62}$Cu, $^{64}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. The therapeutic radionuclide preferably has a decay energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV.

For example, $^{67}$Cu, considered one of the more promising radioisotopes for radioimmunotherapy due to its 61.5 hour half-life and abundant supply of beta particles and gamma rays, can be conjugated to a PAM4 antibody using the chelating agent, p-bromoacetamido-benzyl-tetraethylamine-tetraacetic acid (TETA). Chase, supra. Alternatively, $^{90}$Y, which emits an energetic beta particle, can be coupled to a PAM4 antibody, fusion protein, or fragment thereof, using diethylenetriaminepentaacetic acid (DTPA).

Additional potential radioisotopes include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like.

In another embodiment, a radiosensitizer can be used in combination with a naked or conjugated PAM4 antibody or antibody fragment of the present invention. For example, the radiosensitizercan be used in combination with a radiolabeled PAM4 antibody or antibody fragment. The addition of the radiosensitizer can result in enhanced efficacy when compared to treatment with the radiolabeled antibody or antibody fragment alone. Radiosensitizers are described in D. M. Goldenberg (ed.), CANCER THERAPY WITH RADIOLABELED ANTIBODIES, CRC Press (1995), which is incorporated herein by reference in its entirety.

The PAM4 antibody or fragment thereof, or PAM4 fusion protein or fragment thereof of the present invention that have a boron addend-loaded carrier for thermal neutron activation therapy will normally be effected in similar ways. However, it will be advantageous to wait until non-targeted PAM4 immunoconjugate clears before neutron irradiation is performed. Clearance can be accelerated using an antibody that binds to the PAM4 antibody. See U.S. Pat. No. 4,624,846 for a description of this general principle. For example, boron addends such as carboranes, can be attached to PAM4 antibodies. Carboranes can be prepared with carboxyl functions on pendant side chains, as is well-known in the art. Attachment of carboranes to a carrier, such as aminodextran, can be achieved by activation of the carboxyl groups of the carboranes and condensation with amines on the carrier. The intermediate conjugate is then conjugated to the PAM4 antibody. After administration of the PAM4 antibody conjugate, a boron addend is activated by thermal neutron irradiation and converted to radioactive atoms which decay by α-emission to produce highly toxic, short-range effects.

Furthermore, the present invention includes methods of diagnosing cancer in a subject. Diagnosis may be accomplished by administering a diagnostically effective amount of a diagnostic conjugate, formulated in a pharmaceutically suitable excipient, and detecting said label. The PAM4 antibodies, fusion proteins, and fragments thereof may be conjugated to the diagnostic/detection agent or be administered unconjugated to the diagnostic/detection agent, but before, concurrently, or after administration of the diagnostic/detection agent. Radioactive agents that can be used as diagnostic/detection agents were discussed above. A suitable non-radioactive diagnostic/detection agent is a contrast agent suitable for magnetic resonance imaging, X-rays, computed tomography or ultrasound. Magnetic imaging agents include, for example, non-radioactive metals, such as manganese, iron and gadolinium, complexed with metal-chelate combinations that include 2-benzyl-DTPA and its monomethyl and cyclohexyl analogs, when used along with the antibodies of the invention. See U.S. Ser. No. 09/921,290 filed on Oct. 10, 2001, which is incorporated in its entirety by reference.

Contrast agents, such as MRI contrast agents, contemplated in the present invention include, for example, gadolinium ions, lanthanum ions, dysprosium ions, iron ions, manganese ions or other comparable label, CT contrast agents, and ultrasound contrast agents are suitable for use in the present invention.

Paramagnetic ions suitable for the present invention include include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred.

Ions useful in other contexts, such as X-ray imaging, include but are not limited to lanthanum (III), gold (III), lead (II), and especially bismuth (III). Fluorescent labels include rhodamine, fluorescein and renographin. Rhodamine and fluorescein are often linked via an isothiocyanate intermediate.

Metals are also useful in diagnostic/detection agents, including those for magnetic resonance imaging techniques. These metals include, but are not limited to: Gadolinium, manganese, iron, chromium, copper, cobalt, nickel, dysprosium, rhenium, europium, terbium, holmium and neodymium. In order to load an antibody component with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose. Chelates are coupled to the PAM 4 antibody, fusion protein, or fragments thereof using standard chemistries. The chelate is normally linked to the antibody by a group which enables formation of a bond to the molecule with minimal loss of immunoreactivity and minimal aggregation and/or internal cross-linking. Other, more unusual, methods and reagents for conjugating chelates to antibodies are disclosed in U.S. Pat. No. 4,824,659 to Hawthorne, entitled "Antibody Conjugates", issued Apr. 25, 1989, the disclosure of which is incorporated herein in its entirety by reference. Particularly useful metal-chelate combinations include 2-benzyl-DTPA and its monomethyl and cyclohexyl analogs, used with diagnostic isotopes in the general energy range of 20 to 2,000 keV. The same chelates, when complexed with non-radioactive metals, such as manganese, iron and gadolinium are useful for MRI, when used along with the antibodies of the invention. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}$Ra for RAIT are encompassed by the invention.

Radiopaque and contrast materials are used for enhancing X-rays and computed tomography, and include iodine compounds, barium compounds, gallium compounds, thallium compounds, etc. Specific compounds include barium, diatrizoate, ethiodized oil, gallium citrate, iocarmic acid, iocetamic acid, iodamide, iodipamide, iodoxamic acid, iogulamide, iohexol, iopamidol, iopanoic acid, iprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, and thallous chloride.

The antibodies, fusion proteins, and fragments thereof of the present invention also can be labeled with a fluorescent compound. The presence of a fluorescent-labeled MAb is determined by exposing the antibody to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine. Fluorescently-labeled antibodies are particularly useful for flow cytometry analysis.

Alternatively, the antibodies, fusion proteins, and fragments thereof of this invention can be detectably labeled by coupling the antibody to a chemiluminescent compound. The presence of the chemiluminescent-tagged MAb is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label the antibodies and fragments thereof the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Accordingly, a method of diagnosing a malignancy in a subject is described, comprising performing an in vitro diagnosis assay on a specimen (fluid, tissue or cells) from the subject with a composition comprising a naked PAM4 MAb or fragment thereof or a naked antibody fusion protein or fragment thereof. Immunohistochemistry can be used to detect the presence of PAM4 in a cell or tissue. Preferably, the malignancy that is being diagnosed is a cancer. Most preferably, the cancer is pancreatic cancer.

Additionally, a chelator such as DTPA, DOTA, TETA, or NOTA or a suitable peptide, to which a detectable label, such as a fluorescent molecule, or cytotoxic agent, such as a heavy metal or radionuclide, can be conjugated. For example, a therapeutically useful immunoconjugate can be obtained by conjugating a photoactive agent or dye to an antibody fusion protein. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy (Jori et al. (eds.), PHOTODYNAMIC THERAPY OF TUMORS AND OTHER DISEASES (Libreria Progetto 1985); van den Bergh, *Chem. Britain* 22:430 (1986)). Moreover, monoclonal antibodies have been coupled with photoactivated dyes for achieving phototherapy. Mew et al., *J. Immunol.* 130:1473 (1983); idem., *Cancer Res.* 45:4380 (1985); Oseroff et al., *Proc. Natl. Acad. Sci. USA* 83:8744 (1986); idem., *Photochem. Photobiol.* 46:83 (1987); Hasan et al., *Prog. Clin. Biol. Res.* 288:471 (1989); Tatsuta et al., *Lasers Surg. Med.* 9:422 (1989); Pelegrin et al., *Cancer* 67:2529 (1991). However, these earlier studies did not include use of endoscopic therapy applications, especially with the use of antibody fragments or subfragments. Thus, the present invention contemplates the therapeutic use of immunoconjugates comprising photoactive agents or dyes.

For purposes of therapy, the PAM4 antibodies and fragments thereof of the present invention are administered to a patient in a therapeutically effective amount. An antibody is said to be administered in a "therapeutically effective amount" if the amount administered is physiologically significant. An agent is physiologically significant if its presence results in a detectable change in the physiology of a recipient patient.

A diagnostic/detection agent is a molecule or atom, which may be administered conjugated to an antibody moiety, i.e., antibody or antibody fragment, or subfragment, fusion protein, and fragments thereof and is useful in diagnosing/detecting a disease by locating the cells containing the disease-associated antigen. Useful diagnostic/detection agents include, but are not limited to, radioisotopes, dyes (such as with the biotin-streptavidin complex), radiopaque materials (e.g., iodine, barium, gallium, and thallium compounds and the like), contrast agents, fluorescent compounds or molecules and enhancing agents (e.g., paramagnetic ions) for magnetic resonance imaging (MRI). U.S. Pat. No. 6,331,175 describes MRI technique and the preparation of antibodies conjugated to a MRI enhancing agent and is incorporated in its entirety by reference. Preferably, the diagnostic/detection agents are selected from the group consisting of radioisotopes for nuclear imaging, endoscopic and intravascular detection, enhancing agents for use in magnetic resonance imaging or in ultrasonography, radiopaque and contrast agents for X-rays and computed tomography, and fluorescent compounds for fluoroscopy, including endoscopic fluoroscopy. Fluorescent and radioactive agents conjugated to antibodies or used in bispecific, pretargeting methods, are particularly useful for endoscopic, intraoperative or intravascular detection of the targeted antigens associated with diseased tissues or clusters of cells, such as malignant tumors, as disclosed in Goldenberg U.S. Pat. Nos. 5,716,595, 6,096,289 and U.S. application Ser. No. 09/348,818, incorporated herein by reference in their entirety, particularly with gamma-, beta-, and positron-emitters. Endoscopic applications may be used when there is spread to a structure that allows an endoscope, such as the colon. Radionuclides useful for positron emission tomography include, but are not limited to: F-18, Mn-51, Mn-52m, Fe-52, Co-55, Cu-62, Cu-64, Ga-68, As-72, Br-75, Br-76, Rb-82m, Sr-83, Y-86, Zr-89, Tc-94m, In-110, I-120, and I-124. Total decay energies of useful positron-emitting radionuclides are preferably <2,000 keV, more preferably under 1,000 keV, and most preferably <700 keV. Radionuclides useful as diagnostic/detection agents utilizing gamma-ray detection include, but are not limited to: Cr-51, Co-57, Co-58, Fe-59g, Cu-67, Ga-67, Se-75, Ru-97, Tc-99m, In-111, In-114m, I-123, I-125, I-131, Yb-169, Hg-197, and Tl-201. Decay energies of useful gamma-ray emitting radionuclides are preferably 20-2000 keV, more preferably 60-600 keV, and most preferably 100-300 keV.

In Vitro Diagnosis

The present invention contemplates the use of PAM4 antibodies, including PAM4 fusion proteins and fragments thereof, to screen biological samples in vitro for the presence of the PAM4 antigen. In such immunoassays, the PAM4 antibody, fusion protein, or fragment thereof may be utilized in liquid phase or bound to a solid-phase carrier, as described below. In a preferred embodiment, the PAM4 antibody or fragment thereof is humanized. Also preferred, the PAM4 antibody or fragment thereof is fully human. Still preferred, the PAM4 fusion protein comprises a humanized or fully human PAM4 antibody.

One example of a screening method for determining whether a biological sample contains the PAM4 antigen is the radioimmunoassay (RIA). For example, in one form of RIA, the substance under test is mixed with PAM4 antigen MAb in the presence of radiolabeled PAM4 antigen. In this method, the concentration of the test substance will be inversely proportional to the amount of labeled PAM4 antigen bound to the MAb and directly related to the amount of free, labeled PAM4 antigen. Other suitable screening methods will be readily apparent to those of skill in the art.

Alternatively, in vitro assays can be performed in which a PAM4 antibody, fusion protein, or fragment thereof is bound to a solid-phase carrier. For example, MAbs can be attached to a polymer, such as aminodextran, in order to link the MAb to an insoluble support such as a polymer-coated bead, a plate or a tube.

Other suitable in vitro assays will be readily apparent to those of skill in the art. The specific concentrations of detectably labeled PAM4 antibody and PAM4 antigen, the temperature and time of incubation, as well as other assay conditions may be varied, depending on various factors including the concentration of the PAM4 antigen in the sample, the nature of the sample, and the like. The binding activity of a sample of PAM4 antibody may be determined according to well-known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

The presence of the PAM4 antigen in a biological sample can be determined using an enzyme-linked immunosorbent assay (ELISA). In the direct competitive ELISA, a pure or semipure antigen preparation is bound to a solid support that is insoluble in the fluid or cellular extract being tested and a quantity of detectably labeled soluble antibody is added to permit detection and/or quantitation of the binary complex formed between solid-phase antigen and labeled antibody.

In contrast, a "double-determinant" ELISA, also known as a "two-site ELISA" or "sandwich assay," requires small amounts of antigen and the assay does not require extensive purification of the antigen. Thus, the double-determinant ELISA is preferred to the direct competitive ELISA for the detection of an antigen in a clinical sample. See, for example, the use of the double-determinant ELISA for quantitation of the c-myc oncoprotein in biopsy specimens. Field et al., *Oncogene* 4: 1463 (1989); Spandidos et al., *AntiCancer Res.* 9: 821 (1989).

In a double-determinant ELISA, a quantity of unlabeled MAb or antibody fragment (the "capture antibody") is bound to a solid support, the test sample is brought into contact with the capture antibody, and a quantity of detectably labeled soluble antibody (or antibody fragment) is added to permit detection and/or quantitation of the ternary complex formed between the capture antibody, antigen, and labeled antibody. An antibody fragment is a portion of an antibody such as $F(ab')_2$, $F(ab)_2$, Fab', Fab, and the like. In the present context, an antibody fragment is a portion of a PAM4 MAb that binds to an epitope of the PAM4 antigen. The term "antibody fragment" also includes any synthetic or genetically engineered protein that acts like an antibody by binding to a specific antigen to form a complex. For example, antibody fragments include isolated fragments consisting of the light chain variable region, "Fv" fragments consisting of the variable regions of the heavy and light chains, and recombinant single chain polypeptide molecules in which light and heavy variable regions are connected by a peptide linker. An antibody fusion protein is a recombinantly produced antigen-binding molecule in which two or more of the same or different single-chain antibody or antibody fragment segments with the same or different specificities are linked. The fusion protein may comprise a single antibody component, a multivalent or multispecific combination of different antibody components or multiple copies of the same antibody component. The fusion protein may additionally comprise an antibody or an antibody fragment conjugated to a diagnostic/detection and/or a therapeutic agent. The term PAM4 antibody includes humanized, human and murine antibodies, antibody fragments thereof, immunoconjugates and fragments thereof and antibody fusion proteins and fragments thereof.

Methods of performing a double-determinant ELISA are well-known. See, for example, Field et al., supra, Spandidos et al., supra, and Moore et al., "Twin-Site ELISAs for fos and myc Oncoproteins Using the AMPAK System," in METHODS IN MOLECULAR BIOLOGY, VOL. 10, pages 273-281 (The Humana Press, Inc. 1992).

In the double-determinant ELISA, the soluble antibody or antibody fragment must bind to a PAM4 epitope that is distinct from the epitope recognized by the capture antibody. The double-determinant ELISA can be performed to ascertain whether the PAM4 antigen is present in a biopsy sample. Alternatively, the assay can be performed to quantitate the amount of PAM4 antigen that is present in a clinical sample of body fluid. The quantitative assay can be performed by including dilutions of purified PAM4 antigen.

The PAM4 Mabs, fusion proteins, and fragments thereof of the present invention also are suited for the preparation of an assay kit. Such a kit may comprise a carrier means that is compartmentalized to receive in close confinement one or more container means such as vials, tubes and the like, each of said container means comprising the separate elements of the immunoassay.

For example, there may be a container means containing the capture antibody immobilized on a solid phase support, and a further container means containing detectably labeled antibodies in solution. Further container means may contain standard solutions comprising serial dilutions of PAM4 antigen. The standard solutions of PAM4 antigen may be used to prepare a standard curve with the concentration of PAM4 antigen plotted on the abscissa and the detection signal on the ordinate. The results obtained from a sample containing PAM4 antigen may be interpolated from such a plot to give the concentration of PAM4 antigen in the biological sample.

PAM4 antibodies, fusion proteins, and fragments thereof of the present invention also can be used to detect the presence of the PAM4 antigen in tissue sections prepared from a histological specimen. Such in situ detection can be used to determine the presence of the PAM4 antigen and to determine the distribution of the PAM4 antigen in the examined tissue. In situ detection can be accomplished by applying a detectably-labeled PAM4 antibody to frozen tissue sections. Studies indicate that the PAM4 antigen is preserved in paraffin-embedded sections. General techniques of in situ detection are well-known to those of ordinary skill. See, for example, Ponder, "Cell Marking Techniques and Their Application," in MAMMALIAN DEVELOPMENT: A PRACTICAL APPROACH 113-38 Monk (ed.) (IRL Press 1987), and Coligan at pages 5.8.1-5.8.8.

PAM4 antibodies, fusion proteins, and fragments thereof can be detectably labeled with any appropriate marker moiety, for example, a radioisotope, an enzyme, a fluorescent label, a dye, a chromagen, a chemiluminescent label, a bioluminescent labels or a paramagnetic label. Methods of making and detecting such detectably-labeled PAM4 antibodies are well-known to those of ordinary skill in the art, and are described in more detail below.

The marker moiety can be a radioisotope that is detected by such means as the use of a gamma counter or a scintillation counter or by autoradiography. In a preferred embodiment, the diagnostic conjugate is a gamma-, beta- or a positron-emitting isotope. A marker moiety in the present description refers to a molecule that will generate a signal under predetermined conditions. Examples of marker moieties include radioisotopes, enzymes, fluorescent labels, chemiluminescent labels, bioluminescent labels and paramagnetic labels. As used herein, a diagnostic or therapeutic agent is a molecule or atom which is conjugated to an antibody moiety to produce a conjugate which is useful for diagnosis and for therapy. Examples of diagnostic or therapeutic agents include drugs, toxins, oligonucleotides, immunomodulators, cytokines, hormones, hormone antagonists, enzymes, enzyme inhibitors, isotopes, other antibodies, chelators, dyes, chromagens, boron compounds, and marker moieties.

In one embodiment, an oligonucleotide, such as an antisense molecule inhibiting bcl-2 expression is described in U.S. Pat. No. 5,734,033 (Reed), which is incorporated by reference in its entirety, may be conjugated to, or form the therapeutic agent portion of an immunoconjugate or antibody fusion protein of the present invention. Alternatively, the oligonucleotide may be administered concurrently or sequentially with a naked or conjugated PAM4 antibody or antibody fragment of the present invention. In a preferred embodiment, the oligonucleotides is an antisense oligonucleotide that preferably is directed against an oncogene or oncogene product of a B-cell malignancy, such as bcl-2.

Those of skill in the art will know of other suitable labels, which can be employed in accordance with the present invention. The binding of marker moieties to PAM4 antibodies can be accomplished using standard techniques known to the art. Typical methodology in this regard is described by Kennedy et al., *Clin. Chim. Acta* 70: 1 (1976), Schurs et al., *Clin. Chim. Acta* 81: 1 (1977), Shih et al., *Int'l J. Cancer* 46: 1101 (1990).

The above-described in vitro and in situ detection methods may be used to assist in the diagnosis or staging of a pathological condition. For example, such methods can be used to detect tumors that express the PAM4 antigen such as pancreatic cancer.

In Vivo Diagnosis

The present invention also contemplates the use of PAM4 antibodies for in vivo diagnosis. The method of diagnostic imaging with radiolabeled MAbs is well-known. In the technique of immunoscintigraphy, for example, antibodies are labeled with a gamma-emitting radioisotope and introduced into a patient. A gamma camera is used to detect the location and distribution of gamma-emitting radioisotopes. See, for example, Srivastava (ed.), RADIOLABELED MONOCLONAL ANTIBODIES FOR IMAGING AND THERAPY (Plenum Press 1988), Chase, "Medical Applications of Radioisotopes," in REMINGTON'S PHARMACEUTICAL SCIENCES, 18th Edition, Gennaro et al. (eds.), pp. 624-652 (Mack Publishing Co., 1990), and Brown, "Clinical Use of Monoclonal Antibodies," in BIOTECHNOLOGY AND PHARMACY 227-49, Pezzuto et al. (eds.) (Chapman & Hall 1993).

For diagnostic imaging, radioisotopes may be bound to the PAM4 antibody either directly, or indirectly by using an intermediary functional group. Useful intermediary functional groups include chelators such as ethylenediaminetetraacetic acid and diethylenetriaminepentaacetic acid. For example, see Shih et al., supra, and U.S. Pat. No. 5,057,313.

The radiation dose delivered to the patient is maintained at as low a level as possible through the choice of isotope for the best combination of minimum half-life, minimum retention in the body, and minimum quantity of isotope which will permit detection and accurate measurement. Examples of radioisotopes that can be bound to PAM4 antibody and are appropriate for diagnostic imaging include $^{99m}$Tc and $^{111}$In.

The PAM4 antibodies, fusion proteins, and fragments thereof also can be labeled with paramagnetic ions and a variety of radiological contrast agents for purposes of in vivo diagnosis. Contrast agents that are particularly useful for magnetic resonance imaging comprise gadolinium, manganese, dysprosium, lanthanum, or iron ions. Additional agents include chromium, copper, cobalt, nickel, rhenium, europium, terbium, holmium, or neodymium. PAM4 antibodies and fragments thereof can also be conjugated to ultrasound contrast/enhancing agents. For example, the ultrasound contrast agent is a liposome that comprises a humanized PAM4 IgG or fragment thereof. Also preferred, the ultrasound contrast agent is a liposome that is gas filled.

In a preferred embodiment, a bispecific antibody can be conjugated to a contrast agent. For example, the bispecific antibody may comprise more than one image-enhancing agent for use in ultrasound imaging. In a preferred embodiment, the contrast agent is a liposome. Preferably, the liposome comprises a bivalent DTPA-peptide covalently attached to the outside surface of the liposome. Still preferred, the liposome is gas filled.

Pharmaceutically Suitable Excipient

Additional pharmaceutical methods may be employed to control the duration of action of a PAM4 antibody in a therapeutic application. Control release preparations can be prepared through the use of polymers to complex or adsorb the PAM4 antibody, fusion protein, and fragment thereof. For example, biocompatible polymers include matrices of poly(ethylene-co-vinyl acetate) and matrices of a polyanhydride copolymer of a stearic acid dimer and sebacic acid. Sherwood et al., *Bio/Technology* 10: 1446 (1992). The rate of release of a PAM4 antibody, fusion protein, and fragment thereof from such a matrix depends upon the molecular weight of the PAM4 antibody, fusion protein, and fragment thereof the amount of PAM4 antibody within the matrix, and the size of dispersed particles. Saltzman et al., *Biophys. J.* 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The humanized and human PAM4 antibodies and fragments thereof to be delivered to a subject can consist of the antibody, immunoconjugate, fusion protein, or fragments thereof alone, or can comprise one or more pharmaceutically suitable excipients, one or more additional ingredients, or some combination of these.

The immunoconjugate, naked antibody, and fragments thereof of the present invention can be formulated according to known methods to prepare pharmaceutically useful compositions, whereby the immunoconjugate or naked antibody is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The immunoconjugate or naked antibody of the present invention can be formulated for intravenous administration via, for example, bolus injection or continuous infusion. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The immunoconjugate, naked antibody, and fragments thereof may also be administered to a mammal subcutaneously or even by other parenteral routes. In a preferred embodiment, the PAM4 antibody or fragment thereof is administered in a dosage of 20 to 2000 milligrams protein per dose. Moreover, the administration may be by continuous infusion or by single or multiple boluses. In general, the dosage of an administered immunoconjugate, fusion protein or naked antibody for humans will vary depending upon such factors as the patient's age, weight, height, sex, general medical condition and previous medical history. Typically, it is desirable to provide the recipient with a dosage of immunoconjugate, antibody fusion protein or naked antibody that is in the range of from about 1 mg/kg to 20 mg/kg as a single intravenous infusion, although a lower or higher dosage also may be administered as circumstances dictate. This dosage may be repeated as needed, for example, once per week for four to ten weeks, preferably once per week for eight weeks, and more preferably, once per week for four weeks. It may also be given less frequently, such as every other week for several months. The dosage may be given through various parenteral routes, with appropriate adjustment of the dose and schedule.

The PAM4 antibodies, fusion proteins, and fragments thereof of the present invention can be formulated according to known methods to prepare pharmaceutically useful compositions, whereby PAM4 antibodies, fusion proteins and fragments thereof are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, REMINGTON'S PHARMACEUTICAL SCIENCES, 18th Ed. (1990).

For purposes of therapy, the immunoconjugate, or naked antibody is administered to a mammal in a therapeutically effective amount. A suitable subject for the present invention are usually a human, although a non-human animal subject is also contemplated. An antibody preparation is said to be administered in a "therapeutically effective amount" if the amount administered is physiologically significant. An agent is physiologically significant if its presence results in a detectable change in the physiology of a recipient mammal.

EXAMPLES

The examples below are illustrative of embodiments of the current invention and should not be used, in any way, to limit the scope of the claims.

The following examples discuss experimental studies employing PAM4 MAb and the CaPan1 human pancreatic cancer. The CaPan1 human pancreatic cancer is carried as a xenograft in both subcutaneous and orthotopic sites. The MAb and agent have resulted in significantly improved survival time. High concentrations of PAM4 monoclonal antibody are shown to target xenografted human tumor models to target the majority of pancreatic tumors within an initial group of patients. Employing an in vitro immunoassay to quantitate PAM4-reactive antigen in the blood of patients appears promising in its ability to discriminate pancreatic cancer from pancreatitis, as well as other disease and normal groups.

Clinical studies with PAM4 MAb have shown that a majority of the lesions were targeted in patients and that there is no indication of uptake in normal tissues. Dosimetry indicated that it was possible to deliver 10 to 20 cGy/mCi to tumors, with a tumor to red marrow dose ratio of 3:1 to 10:1. These data suggest that PAM4 may be useful for development of a phase-I trial for the treatment of pancreatic cancer.

Example 1

Immunohistochemistry Staining Studies

Immunohistochemistry on normal adult tissues showed that the PAM4 reactive epitope was restricted to the gastrointestinal tract where staining was weak, yet definitely positive (Table 1). Normal pancreatic tissue, including ducts, ductules, acini, and islet cells, were negative for staining. A PAM4 based enzyme immunoassay with tissue homogenates as antigens generally supported the immunohistology data (Table 2). The PAM4 epitope was absent from normal pancreas and other nongastrointestinal tissues. In neoplastic tissues, PAM4 was reactive with twenty one out of twenty five (85%) pancreatic cancers (Table 3). PAM4 reactivity appeared to correlate with the stage of tumor differentiation. For example, twenty out of twenty one well and moderately differentiated pancreatic tumors were positive whereas only one out of four poorly differentiated tumors were positive. Generally, poorly differentiated tumors represent less than 10% of all pancreatic cancers.

These studies have shown the PAM4 reactivity and tissue distribution (both normal and cancer) to be unlike that reported for CA19.9, DUPAN2, SPAN1, Nd2, B72.3, and the Lewis antigens. Together with crossblocking studies performed with certain of these MAbs, the data suggests that the PAM4 MAb recognizes a unique and novel epitope. When compared to CA19.9, DUPAN2, and aLe$^a$, PAM4 appears to be more restricted in its tissue distribution and it is reactive with a higher percentage of pancreatic tumors. Moreover, it gives a greater overall intensity of reaction at equivalent concentrations and is reactive with a higher percentage of cells within the tumors. Finally, PAM4 was found to be only weakly reactive with three out of twelve chronic pancreatitis specimens, whereas CA19.9 and DUPAN2 were strongly reactive with all twelve specimens. Although it is recognized that specificity is dependent upon the type of assay employed and the range and number of tissues examined, the ability of PAM4 to discriminate between normal and neoplastic pancreatic tissue, its ability to react with a large percentage of the cancer specimens, as well as the high intensity of the reactions, were important rationales for pursuing developmental studies of clinical application.

TABLE 1

Immunoperoxidase Staining of Normal Adult Tissues with MAb PAM4

| Tissue | Staining Reaction |
|---|---|
| Pancreas (22)[a] | |
| Ducts | — |
| Acini | — |
| Islets | — |
| Submaxillary gland (2) | — |
| Esophagus (2) | — |
| Stomach (3) | +mucus secreting cells |
| Duodenum (3) | +goblet cells |
| Jejunum (3) | +goblet cells |
| Ileum (3) | +goblet cells |
| Colon (5) | +goblet cells |
| Liver (3) | — |
| Gallbladder (2) | — |
| Bronchus (3) | — |
| Lung (3) | — |
| Heart (3) | — |
| Spleen (3) | — |
| Kidney (3) | — |
| Bladder (3) | — |
| Prostate (2) | — |
| Testes (2) | — |
| Uterus (2) | — |
| Ovary (2) | — |

[a]( ) number of individual specimens examined.

TABLE 2

Monoclonal Antibody PAM4 Reactivity with Normal Adult Tissue Homogenates by EIA

| Tissue | ug/g tissue[a] |
|---|---|
| Pancreas | 6.4 |
| Esophagus | 8.1 |
| Stomach | 61.3 |
| Duodenum | 44.7 |
| Jejunum | 60.6 |
| Colon | 74.5 |
| Liver | 0.0 |
| Gallbladder | 5.6 |
| Heart | 3.7 |
| Spleen | 3.4 |
| Kidney | 6.6 |
| Bladder | 4.9 |
| Thyroid | 3.5 |
| Adrenal | 1.3 |
| Ureter | 2.6 |
| Testes | 3.9 |
| CaPan1 Pancreatic Tumor | 569 |

[a]values are mean from two autopsy specimens

TABLE 3

Immunohistochemical Reactivity of Several Monoclonal Antibodies with Pancreatic Tumors

| | Differentiation | PAM4 | CA19.9 | aLe[a] | DUPAN2 |
|---|---|---|---|---|---|
| 1 | W | +++ | − | − | +++ |
| 2 | M | ++ | +++ | +++ | + |
| 3 | M | + | − | + | + |
| 4 | M | +++ | +++ | +++ | + |
| 5 | M | ++ | + | − | − |
| 6 | M | + | ND | ND | ND |
| 7 | M* | +++ | +++ | +++ | +++ |
| 8 | M | + | − | − | +++ |
| 9 | M | ++ | + | ++ | − |
| 10 | M* | ++ | ++ | ++ | +++ |
| 11 | M | ++ | +++ | +++ | + |
| 12 | M | ++ | + | + | +++ |
| 13 | M | + | +++ | +++ | + |
| 14 | M | ++ | + | + | ++ |
| 15 | M | +++ | + | + | ++ |
| 16 | M | + | + | ++ | − |
| 17 | M | − | + | + | − |
| 18 | M | ++ | ++ | ++ | ++ |
| 19 | M | +++ | + | +++ | ++ |
| 20 | M | + | − | − | − |
| 21 | M | +++ | +++ | + | ++ |
| 22 | P | + | + | + | +++ |
| 23 | P | − | − | − | − |
| 24 | P | − | − | − | − |
| 25 | P | − | − | + | − |
| TOTAL | | 21/25 | 17/24 | 18/24 | 16/24 |

−: Negative;
+: 5-20% of tissue is stained;
++: 21-50% of tissue is stained;
+++: >50% of tissue is stained;
W, M, P: Well, moderate, or poor differentiation;
*Metastatic tissue;
ND: Not Done

TABLE 4

Immunoperoxidase Staining of Neoplastic Tissues with MAb PAM4

| Tissue | Positive/Total |
|---|---|
| Pancreas | 21/25 |
| Colon | 10/26 |
| Stomach | 1/5 |
| Lung | 1/15 |
| Breast | 0/30 |
| Ovarian | 0/10 |
| Prostate | 0/4 |
| Liver | 0/10 |
| Kidney | 0/4 |

Example 2

In Vivo Biodistribution and Tumor Targeting of Radiolabeled PAM4

Initial biodistribution studies of PAM4 were carried out in a series of four different xenografted human pancreatic tumors covering the range of expected differentiation. Each of the four tumor lines employed, AsPc1, BxPc3, Hs766T and CaPan1, exhibited concentrations of $^{131}$I-PAM4 within the tumors (range: 21%-48% ID/g on day three) that was significantly ($p<0.01$-0.001) higher than concomitantly administered nonspecific, isotype-matched Ag8 antibody (range: 3.6%-9.3% ID/g on day three). The biodistribution data were used to estimate potential radiation doses to the tumor of 12,230; 10,684; 6,835; and 15,843 cGy/mCi of injected dose to AsPc1, BxPc3, Hs766T and CaPan1, respectively. With an actual maximum tolerated dose (MTD) of 0.7mCi, PAM4 could provide substantial rad dose to each of the xenografted tumor models. In each tumor line the blood levels of radiolabeled PAM4 were significantly ($p<0.01$-0.001) lower than the nonspecific Ag8. Potential radiation doses to the blood from PAM4 were 1.4-4.4 fold lower than from Ag8. When radiation doses to the tumor from PAM4 were normalized to the blood doses from PAM4, the tumors received doses that were 2.2; 3.3; 3.4; and 13.1-fold higher than blood, respectively. Importantly, potential radiation doses to non-tumor tissues were minimal.

The biodistribution of PAM4 was compared with an anti-CEA antibody, MN14, using the CaPan1 tumor model. The concentration of PAM4 within the tumor was much greater than the MN14 at early timepoints, yielding tumor:blood ratios at day three of 12.7±2.3 for PAM4 compared to 2.7±1.9 for MN14. Although PAM4 uptake within the tumor was significantly higher than for MN14 at early timepoints (day one—p<0.001; day three—p<0.01), dosimetry analyses indicated only a 3.2-fold higher dose to the tumor from PAM4 as compared to MN14 over the fourteen day study period. This was due to a rapid clearance of PAM4 from the tumor, such that at later timepoints similar concentrations of the two antibodies were present within the tumors. A rapid clearance of PAM4 from the tumor was also noted in the BxPc3 and Hs766T but not AsPc1 tumor models. These observations were unlike those reported for other anti-mucin antibodies, as for example G9 and B72.3 in colorectal cancer, where each exhibited longer retention times as compared to the MN14 antibody. Results from studies on the metabolism of PAM4, indicate that after initial binding to the tumor cell, antibody is rapidly released, possibly being catabolized or being shed as an antigen:antibody complex. This might have had unfavorable implications for the use of the antibody in patients except that the blood clearance is also very rapid. These data suggest that $^{131}$I may not be the appropriate choice of isotope for therapeutic applications. A short-lived isotope, such as $^{90}$Y or $^{188}$Re, that can be administered frequently may prove to be a more effective reagent.

PAM4 showed no evidence of targeting to normal tissues, except in the CaPan1 tumor model, where a small but statistically significant splenic uptake was observed (range 3.1-7.5% ID/g on day three). This type of splenic targeting has been observed in the clinical application of the anti-mucin antibodies B72.3 and CC49. Importantly, these studies also reported that splenic targeting did not affect tumor uptake of antibody nor did it interfere with interpretation of the nuclear scans. These studies suggested that splenic targeting was not due to crossreactive antigens in the spleen, nor to binding by $F_c$ receptors, but rather to one or more of the following possibilities: direct targeting of antigen trapped in the spleen, or indirect uptake of antigen:antibody complexes formed either in the blood or released from the tumor site. The latter would require the presence of immune complexes in the blood; however, these were not observed when specimens as early as five minutes and as late as seven days were examined by gel filtration (HPLC, GF-250 column); radiolabeled antibody eluted as native material. The former explanation seems more likely in view of the fact that the CaPan1 tumor produced large quantities of PAM4-reactive antigen, 100 to 1000-fold higher than for the other tumor cell lines examined. The lack of splenic targeting by PAM4 in these other tumor lines suggests that this phenomenon was related to excessive antigen production. In any event, splenic targeting can be overcome by increasing the protein dose to 10 ug from the original 2 ug dose. A greater amount of the splenic entrapped antigen presumably was complexed with unlabeled PAM4 rather than radiolabeled antibody. Increasing the protein dose had no adverse effect upon targeting of PAM4 to the tumor or nontumor tissues. In fact, an increase of the protein dose to 100 ug more than doubled the concentration of radiolabeled PAM4 within the CaPan1 tumor.

Example 3

Development of Orthotopic Pancreatic Tumor Model in Athymic Nude Mice

In order to resemble the clinical presentation of pancreatic cancer in an animal model more closely, applicants developed an orthotopic model by injecting of tumor cells directly into the head of the pancreas. Orthotopic CaPan1 tumors grew progressively without overt symptoms until the development of ascites and death at ten to fourteen weeks. By three to four weeks post-implantation, animals developed a palpable tumor of approximately 0.2 g. Within eight weeks of growth, primary tumors of approximately 1.2 g along with metastases to the liver and spleen were observed (1-3 metastatic tumors/animal; each tumor <0.1 g). At ten to fourteen weeks seeding of the diaphragm with development of ascites were evident. Ascites formation, and occasional jaundice, were usually the first overt indications of tumor growth. Ascites is an accumulation of fluid in the abdominal cavity and jaundice is a yellowing of the skin and eyes due to excessive bile pigments in the blood. At this time tumors were quite large, 1 to 2 g, and animals had at most only three to four weeks until death occurred.

Radiolabeled $^{131}$I-PAM4, administered to animals bearing four week old orthotopic tumors (approximately 0.2 g) showed specific targeting to the primary tumor with localization indices of 7.9±3.0 at day one increasing to 22.8±15.3 at day fourteen. No evidence of specific targeting to other tissues was noted. In one case where tumor metastases to the liver and spleen were observed, both metastases were targeted, and had high concentrations of radiolabeled antibody. In addition, approximately half of the animals developed a subcutaneous tumor at the incision site. No significant differences were noted in the targeting of orthotopic and subcutaneous tumors within the same animal, and no significant differences were observed in the targeting of orthotopic tumor whether or not the animal had an additional subcutaneous tumor. The estimated radiation doses from PAM4 were 6,704 and 1,655 cGy/mCi to the primary tumor and blood, respectively.

Example 4

Development of an Enzyme Immunoassay for Quantification of Circulating Tumor Antigen We have developed an enzyme immunoassay employing PAM4 as the capture reagent with an unlabeled, purified IgG derived from rabbit polyclonal, anti-pancreatic mucin, followed by peroxidase labeled donkey anti-rabbit IgG as the detection reagent. The following results were obtained through use of this assay.

Within the range of antigen detected by the assay, coefficient of variation values were obtained of less than 10%. Sera from twenty five healthy individuals were examined and exhibited a mean ±S.D. of 4.0±3.1 units. A cutoff value for positive response was then set to the mean +2 S.D.=10.2 units. Out of a total of thirty seven pancreatic cancer patients, thirty two or 86% were positive by this assay, whereas only three out of thirteen pancreatitis patients were positive. PAM4 antigen was elevated in 55% ($^{18}$/$_{33}$) of colorectal cancer patients, a number roughly similar to the 40% of colorectal cancer specimens reactive with PAM4 by immunohistochemistry. Amongst other cancers, PAM4 antigen was positive in four out of sixteen ovarian cancer, and five out of twenty breast cancer patients, all of whom had extensive disease. Also, as can be seen in Table 5 below the median value for pancreatic cancer (84.5 units) is on the order of ten fold greater than for all of the other cancer groups (except biliary cancer) even though the overwhelming majority of these cases were late stage, large tumor burden.

TABLE 5

PAM4 Reactivity with Sera

| | | Units/ml | | | |
|---|---|---|---|---|---|
| | n | Mean | SD | Median | Range | % Positive[a] |
| Normal | 25 | 4.0 | 3.1 | 4.7 | 0.0-9.4 | 0% |
| Pancreatitis | 13 | 14.6 | 20.3 | 6.8 | 0.4-66.7 | 23% |
| Pancreatic CA | 37 | 317.5 | 427.1 | 84.5 | 0.9-1000 | 86% |
| Biliary CA | 8 | 155.4 | 343.8 | 37.8 | 6.6-1000 | 63% |
| Hepatoma CA | 30 | 7.9 | 8.0 | 6.4 | 0.0-32.8 | 30% |
| Colorectal CA | 33 | 50.0 | 171.6 | 11.8 | 3.4-1000 | 55% |
| Lung CA | 38 | 25.8 | 44.6 | 9.3 | 0.0-196.0 | 39% |
| Breast CA | 20 | 11.1 | 18.5 | 5.8 | 0.0-83.3 | 25% |
| Ovarian CA | 16 | 68.9 | 248.4 | 5.5 | 0.0-1000 | 25% |
| Non-Hodgkin's Lymphoma | 14 | 6.6 | 3.1 | 7.5 | 2.2-12.8 | 14% |

[a]Cutoff 10.2 units/ml (mean + 2 S.D.)

In addition to these findings, a preliminary study was performed in the orthotopic model to examine the potential use of this PAM4 assay in management. At two weeks post-implantation of orthotopic CaPan1 tumor (estimated tumor mass of 0.15 g), none of the animals had detectable antigen in the blood. At four weeks (estimated tumor mass of 0.2 g) one out of five animals had a detectable level of antigen, (72 units), and at six weeks (estimated tumor volume of 0.4 g) four out of five had quantifiable antigen (range: 98-6080 units). A severe limiting factor in terms of determining the earliest time point at which serum borne antigen could be detected was the limited amount of blood obtainable, such that repeated bleedings could be performed. Thus sera were diluted 1:10 prior to assay.

Example 5

Experimental Radioimmunotherapy of Pancreatic Cancer

The initial studies on the use of $^{131}$I-PAM4 for therapy were carried out with the CaPan1 tumor, which was grown as a subcutaneous xenograft in athymic mice. Animals bearing a 0.25 g tumor were administered 350 μCi, $^{131}$I-PAM4 in an experiment that also compared the therapeutic effects of a similar dose of nonspecific Ag8. The MTD for administration of $^{131}$I-PAM4 to animals bearing 1 cm$^3$ tumors is 700 μCi. By weeks five and six, the PAM4 treated animals showed a dramatic regression of tumor, and even at week twenty seven, five out of eight remained tumor free. The untreated, as well as Ag8-treated animals, showed rapid progression of tumor growth although a significant difference was noted between these two control groups. At seven weeks, tumors from the untreated group had grown 20.0±14.6-fold from the initial timepoint whereas the $^{131}$I-Ag8-treated tumors had grown only 4.9±1.8-fold. At this time point, the PAM4 tumors had regressed to 0.1±0.1-fold of their original size, a significant difference from both untreated (p<0.001) and nonspecific Ag8-treated (p<0.01) animals.

Although the CaPan1 tumors were sensitive to treatment with $^{131}$I-PAM4, the outcome, that is, regression or progression of the tumor, is dependent upon many factors including initial tumor size. Thus, groups of animals bearing CaPan1 tumor burdens of 0.25 g, 0.5 g, 1.0 g, or 2.0 g were treated with a single dose of the 350 μCi $^{131}$I-PAM4. The majority of animals having tumors of initial size 0.25 g and 0.5 g (nine of ten animals in each group) showed tumor regression or growth inhibition for at least sixteen weeks post treatment. In the 1.0 g tumor group five out of seven showed no tumor growth for the sixteen week period and in the 2.0 g tumor group six out of nine showed no tumor growth for a period of six weeks before progression occurred. Although a single 350 μCi dose was not as effective against the larger tumors, a single dose may very well not be the appropriate regimen; toxicity studies indicating the ability to give multiple cycles of radioimunotherapy. Animals bearing CaPan1 tumors averaging 1.0 g, were given either a single dose of 350 μCi $^{131}$I-PAM4, two doses given at times zero and four weeks or were left untreated. The untreated group had a mean survival time of 3.7+/−1.0 weeks (survival defined as time for tumor to reach 5 cm$^3$). Animals died as early as three weeks, with no animal surviving past six weeks. A single dose of 350 μCi $^{131}$I-PAM4 produced a significant increase in the survival time to 18.8+/−4.2 weeks (p<0.0001). The range of animal deaths extended from weeks thirteen to twenty five. None of the animals were alive at the end of the study period of twenty six weeks.

A significant increase in survival time was observed for the two dose group as compared to the single dose group. Half of the animals were alive at the twenty six week timepoint with tumor sizes from 1.0-2.8 cm$^3$, and a mean tumor growth rate of 1.6+/−0.7 fold from initial tumor size. For those animals that were non-survivors at twenty six weeks, the mean survival time (17.7+/−5.3 weeks) was similar to the single dose group.

Therapy studies with PAM4 have also used the orthotopic tumor model. Groups of animals bearing four week old orthotopic tumors (estimated tumor weight of 0.25 g) were either left untreated or treated with a single dose of either 350 uCi $^{131}$I-PAM4 or 350 uCi of $^{131}$I-nonspecific Ag8. The untreated animals had a 50% death rate by week ten with no survivors at week fifteen. Animals administered nonspecific $^{131}$I-Ag8 at four weeks of tumor growth, showed a 50% death rate at week seven with no survivors at week fourteen. Although statistically (logrank analysis) there were no differences between these two groups, it is possible that radiation toxicity had occurred in about half of the Ag8 treated animals. Radiolabeled PAM4, however, provided a significant survival advantage (p<0.001) as compared to the untreated or Ag8 treated animals, with 70% survival at sixteen weeks, the end of the experiment. At this time the surviving animals were sacrificed to determine tumor size. All animals had tumor with an average weight of 1.2 g, as well as one or two small (<0.1 g) metastases evident in four of the seven animals. At sixteen weeks of growth, these tumors were more representative of an eight week old tumor.

Example 6

Combined Modality Gemzar Chemotherapy and $^{131}$I-PAM4 Radioimmunotherapy

Initial studies into the combined use of gemcitabine (gemzar) with $^{131}$I-PAM4 radioimmunotherapy were performed as a checkerboard array; a single dose of Gemzar (0, 100, 200, 500 mg/kg) versus a single dose of $^{131}$I-PAM4 ([MTD=700 µCi] 100%, 75%, 50%, 0% of the MTD). The combined MTD was found to be 500 mg/kg Gemzar with 350 µCi $^{131}$I-PAM4 (50% MTD). Toxicity, as measured by loss of body weight, went to the maximum considered as nontoxic; that is 20% loss in body weight. Although the combined treatment protocol was significantly more effective than gemzar alone, the treatment was no more effective than radioimmunotherapy alone. The next studies were performed at a low dose of gemzar and radioimmunotherapy to examine if a true synergistic therapeutic effect would be observed. Animals bearing tumors of approximately 1 cm$^3$ (approximately 5% of body weight) were administered gemzar, 100 mg/kg on days zero, three, six, nine, and twelve, with 100 µCi of $^{131}$I-PAM4 given on day zero. A therapeutic effect was observed with statistically significant (p<0.0001) regression (two of five tumors less than 0.1 cm$^3$) and/or growth inhibition of the tumors compared to gemzar alone. Of additional note, in terms of body weight, toxicity was not observed. The combination treatment protocol can, if necessary, be delivered in multiple cycles, with the second treatment cycle beginning in week four as was done with the radioimmunotherapy alone studies described above.

Example 7

Humanized PAM4 Mab

A preferred embodiment of this invention utilizes the monoclonal antibody, MAb hPAM4, which is a humanized IgG of the murine PAM4 raised from a pancreatic cancer mucin. Humanization of the murine PAM4 sequences is utilized to reduce the human antimouse antibody response that patients experience. To produce the humanized PAM4, murine complementarity determining regions (CDR) are transferred from heavy and light variable (V) chains of the mouse immunoglobulin into a human V-domain, followed by the replacement of some human residues in the framework regions with their murine counterparts. Humanized monoclonal antibodies in accordance with this invention are suitable for use in in vitro and in vivo diagnostic and therapeutic methods.

Comparison of the variable (V) region framework (FR) sequences of the murine PAM4 MAb (FIGS. 1A and 1B) to registered human antibodies in the Kabat database showed that the FRs of PAM4 Vκ and VH exhibited the highest degree of sequence homology to that of the human antibodies Walker Vκ and Wil2 VH, respectively. Therefore, the Walker Vκ and Wil2 VH FRs were selected as the human frameworks into which the murine CDRs for PAM4 Vκ and V$_H$ were grafted, respectively (FIG. 3). The FR4 sequence of the human antibody, NEWM, however, was used to replace the Wil2 FR4 sequence for the humanization of the PAM4 heavy chain (FIG. 3B). A few amino acid residues in PAM4 FRs that flank the putative CDRs were maintained in hPAM4 based on the consideration that these residues have more impact on Ag binding than other FR residues. These residues are 21M, 47W, 59P, 60A, 85S, 87F, and 100G of Vκ and 27Y, 30P, 38K, 48I, 66K, 67A, and 69L of VH. The DNA and amino acid sequences of hPAM4 Vκ (SEQ ID NO: 16) and VH (SEQ ID NO: 19) are shown in FIGS. 3A and 3B, respectively.

A modified strategy as described by Leung et al. (Leung et al., 1994)) was used to construct the designed Vκ and VH genes for hPAM4 using a combination of long oligonucleotide syntheses and PCR as illustrated in FIG. 4. For the construction of the hPAM4 VH domain, two long oligonucleotides, hPAM4VHA (173-mer) and hPAM4VHB (173-mer) were synthesized on an automated DNA synthesizer (Applied Biosystem).

hPAM4VHA represents nt 17 to 189 of the hPAM4 V$_H$ domain.

```
5'- AGTCTGGGGC TGAGGTGAAG AAGCCTGGGG CCTCAGTGAA

GGTCTCCTGC GAGGCTTCTG GATACACATT CCCTAGCTAT

GTTTTGCACT GGGTGAAGCA GGCCCCTGGA CAAGGGCTTG

AGTGGATTGG ATATATTAAT CCTTACAATG ATGGTACTCA

GTACAATGAG AAG-3'
(SEQ ID NO:20)
``` hPAM4VHB represents the minus strand of the hPAM4 VH domain complementary to nt 169 to 341.

```
5'- AGGGTTCCCT GGCCCCAGTA AGCAAATCCG TAGCTACCAC

CGAAGCCTCT TGCACAGTAA TACACGGCCG TGTCGTCAGA

TCTCAGCCTG CTCAGCTCCA TGTAGGCTGT GTTGATGGAC

GTGTCCCTGG TCAGTGTGGC CTTGCCTTTG AACTTCTCAT

TGTACTGAGT ACC-3'
(SEQ ID NO: 21)
```

The 3'-terminal sequences (21 nt residues) of hPAM4VHA and VHB are complementary to each other. Under defined PCR condition, 3'-ends of hPAM4VHA and VHB anneal to form a short double stranded DNA flanked by the rest of the long oligonucleotides. Each annealed end serves as a primer for the transcription of the single stranded DNA, resulting in a double strand DNA composed of the nt 17 to 341 of hPAM4 VH. This DNA was further amplified in the presence of two short oligonucleotides, hPAM4VHBACK and hPAM4VHFOR to form the full-length hPAM4 VH. The underlined portions are restriction sites for subcloning as shown in FIG. 4B.

```
hPAM4VHBACK
5'-CAG GTG CAG CTG CAG CAG TCT GGG GCT GAG

GTG A-3'
(SEQ ID NO:22)

hPAM4VHFOR
5'-TGA GGA GAC GGT GAC CAG GGT TCC CTG GCC

CCA-3'
(SEQ ID NO:23)
```

A minimal amount of hPAM4VHA and VHB (determined empirically) was amplified in the presence of 10 µL of 10×PCR Buffer (500 mM KCL, 100 mM Tris. HCL buffer, pH 8.3, 15 mM MgCl$_2$), 2 µmol of hPAM4VHBACK and hPAM4VKFOR, and 2.5 units of Taq DNA polymerase (Perkin Elmer Cetus, Norwalk, Conn.). This reaction mixture was subjected to three cycles of polymerase chain reaction (PCR) consisting of denaturation at 94° C. for 1 minute, annealing at 45° C. for 1 minute, and polymerization at 72° C. for 1.5 minutes. This procedure was followed by 27 cycles of PCR reaction consisting of denaturation at 94° C. for 1 minute, annealing at 55° C. for 1 minute, and polymerization at 72° C. for 1 minute. Double-stranded PCR-amplified product for hPAM4 VH was gel-purified, restriction-digested with PstI and BstEII restriction sites and cloned into the complementary PstI/BstEII restriction sites of the heavy chain staging vector, VHpBS2, in which the $V_H$ sequence was fully assembled with the DNA sequence encoding the translation initiation codon and a secretion signal peptide in-frame ligated at the 5'-end and an intron sequence at the 3'-end. VHpBS2 is a modified staging vector of VHpBS (Leung et al., Hybridoma, 13:469 (1994)), into which a XhoI restriction site was introduced at sixteen bases upstream of the translation initiation codon to facilitate the next subcloning step. The assembled VH gene was subcloned as a XhoI-BamHI restriction fragment into the expression vector, pdHL2, which contains the expression cassettes for both human IgG heavy and light chains under the control of IgH enhancer and $MT_1$ promoter, as well as a mouse dhfr gene as a marker for selection and amplification (FIG. 4B). Since the heavy chain region of pdHL2 lacks a BamHI restriction site, this ligation requires use of a linker to provide a bridge between the BamHI site of the variable chain and the HindIII site present in the pdHL2 vector. The resulting expression vectors were designated as hPAM4VHpdHL2.

For constructing the full length DNA of the humanized Vκ sequence, hPAM4VKA (157-mer) and hPAM4VKB (156-mer) were synthesized as described above. hPAM4VKA and VKB were amplified by two short oligonucleotides hPAM4VKBACK and hPAM4VKFOR as described above.

hPAM4VKA represents nt 16 to 172 of the hPAM4 Vκ domain.

```
5'-CAGTCTCCAT CCTCCCTGTC TGCATCTGTA GGAGACAGAG

TCACCATGAC CTGCAGTGCC AGCTCAAGTG TAAGTTCCAG

CTACTTGTAC TGGTACCAAC AGAAACCAGG GAAAGCCCCC

AAACTCTGGA TTTATAGCAC ATCCAACCTG GCTTCTG-3'
(SEQ ID NO:24)
``` hPAM4VKB represents the minus strand of the hPAM4 Vκ domain complementary to nt 153 to 308.

```
5'-GTCCCCCCTC CGAACGTGTA CGGGTACCTA TTCCACTGAT

GGCAGAAATA AGAGGCAGAA TCTTCAGGTT GCAGACTGCT

GATGGTGAGA GTGAAGTCTG TCCCAGATCC ACTGCCACTG

AAGCGAGCAG GGACTCCAGA AGCCAGGTTG GATGTG-3'
(SEQ ID NO:25)
```

The 3'-terminal sequences (20 nt residues) of hPAM4VKA and VKB are complementary to each other. Under defined PCR condition, 3'-ends of hPAM4VKA and VKB anneal to form a short double stranded DNA flanked by the rest of the long oligonucleotides. Each annealed end serves as a primer for the transcription of the single stranded DNA, resulting in a double strand DNA composed of the nt 16 to 308 of hPAM4 Vκ. This DNA was further amplified in the presence of two short oligonucleotides, hPAM4VKBACK and hPAM4VKFOR to form the full-length hPAM4 Vκ. The underlined portions are restriction sites for subcloning as described below.

```
hPAM4VKBACK
5'-GAC ATC CAG CTG ACC CAG TCT CCA TCC TCC

CTG-3'
(SEQ ID NO:26)

hPAM4VKFOR
5'- TTA GAT CTC CAG TCG TGT CCC CCC TCC GAA

CGT-3'
```

Gel-purified PCR products for hPAM4 Vκ were restriction-digested with PvuII and BglII and cloned into the complementary PvuII/BclI sites of the light chain staging vector, VKpBR2. VKpBR2 is a modified staging vector of VKpBR (Leung et al., Hybridoma, 13:469 (1994)), into which a XbaI restriction site was introduced at sixteen bases upstream of the translation initiation codon. The assembled Vκ genes were subcloned as XbaI-BamHI restriction fragments into the expression vector containing the VH sequence, hPAM4VHpdHL2. The resulting expression vectors were designated as hPAM4pdHL2.

Approximately 30 ug of hPAM4pdHL2 was linearized by digestion with SalI and transfected into Sp2/0-Ag14 cells by electroporation at 450 V and 25 μF. The transfected cells were plated into 96-well plates and incubated in a $CO_2$ cell culture incubator for two days and then selected for MTX resistance. Colonies surviving selection emerged in two to three weeks and were screened for human antibody secretion by ELISA assay. Briefly, supernatants (~100 ul) from the surviving colonies were added into the wells of an ELISA microplate precoated with goat anti-human IgG F(ab')$_2$ fragment-specific Ab. The plate was incubated for one hour at room temperature. Unbound proteins were removed by washing three times with wash buffer (PBS containing 0.05% Tween-20). Horseradish peroxidase-conjugated goat anti-human IgG Fc fragment-specific Ab was added to the wells. Following incubation for one hour, a substrate solution (100 μL/well) containing 4 mM o-phenylenediamine dihydrochloride (OPD) and 0.04% $H_2O_2$ in PBS was added to the wells after washing. Color was allowed to develop in the dark for 30 minutes and the reaction was stopped by the addition of 50 μL of 4 N $H_2SO_4$ solution. The bound human IgG was measured by reading the absorbance at 490 nm on an ELISA reader. Positive cell clones were expanded and hPAM4 was purified from cell culture supernatant by affinity chromatography on a Protein A column.

The Ag-binding activity of hPAM4 was confirmed by ELISA assay in microtiter plate coated with pancreas cancer cell extractsAn ELISA competitive binding assay using PAM4-antigen coated plates were developed to assess the Ag-binding affinity of hPAM4 in comparison with that of a chimeric PAM4 composed of murine V and human C domains. Constant amounts of the HRP-conjugated cPAM4 mixed with varying concentrations of cPAM4 or hPAM4 were added to the coated wells and incubated at room temperature for 1-2 h. The amount of HRP-conjugated cPAM4 bound to the CaPan1 Ag was revealed by reading the absorbance at 490 nm after the addition of a substrate solution containing 4 mM o-phenylenediamine dihydrochloride and 0.04% $H_2O_2$. As shown by the competition assays in FIG. 4, hPAM4 and cPAM4 antibodies exhibited similar binding activities.

Suitable host cells include microbial or mammalian host cells. A preferred host is the human cell line, PER.C6, which was developed for production of MAbs, and other fusion proteins. Accordingly, a preferred embodiment of the present invention is a host cell comprising a DNA sequence encoding a PAM4 MAb, conjugate, fusion protein or fragments thereof. PER.C6 cells (WO 97/00326) were generated by transfection of primary human embryonic retina cells, using a plasmid that contained the Adserotype 5 (Ad5) E1A- and E1B-coding sequences (Ad5 nucleotides 459-3510) under the control of the human phosphoglycerate kinase (PGK) promoter. E1A and E1B are adenovirus early gene activation protein 1A and 1B, respectively. The methods and compositions are particularly useful for generating stable expression of human recombinant proteins of interest that are modified post-translationally, e.g. by glycosylation. Several features make PER.C6 particularly useful as a host for recombinant protein production, such as PER.C6 is a fully characterized human cell line and it was developed in compliance with good laboratory practices. Moreover, PER.C6 can be grown as a suspension culture in defined serum-free medium devoid of any human- or animal-derived proteins and its growth is compatible with roller bottles, shaker flasks, spinner flasks and bioreactors with doubling times of about 35 hours. Finally, the presence of E1A causes an up regulation of expression of genes that are under the control of the CMV enhancer/promoter and the presence of E1B prevents p53-dependent apoptosis possibly enhanced through over expression of the recombinant transgene. In one embodiment, the cell is capable of producing 2 to 200-fold more recombinant protein and/or proteinaceous substance than conventional mammalian cell lines. Another preferred cell is Sp210-Ag14 cell.

Example 8

Therapy of a Patient with Inoperable Pancreatic Carcinoma

A 56-year-old male with extensive, inoperable adenocarcinoma of the pancreas, substantial weight loss (30 lbs of weight or more), lethargy and weakness is given $^{90}$Y-PAM4 radiolabeled humanized antibody at a dose of 30 mCi of 90-Y and 50 mg antibody protein, in a two hour i.v. infusion. Five days later, the patient is then given a standard course of gemcitabine chemotherapy. If no evidence after a few months of side effects from therapy, the therapy regimen is repeated. During a follow-up examination a few weeks later, it is predicted that the patient will appear more active and the weight loss will slow. The CT scan of the pancreas is expected to suggest either stable disease or a slight reduction of tumor mass. A repeat examination a few months later should show, by computed tomography, a substantial reduction of tumor mass, and the patient may therefore be considered for resection of the pancreatic tumor mass.

Example 9

Pretargeting with Bispecific PAM4×734 and $^{99m}$Tc-or $^{111}$In-Labeled Peptide Haptens For imaging of pancreatic cancer using a pretargeted approach we prepared a bispecific F(ab')$_2$ antibody (bsMAb) consisting of a chimeric PAM4 (cPAM4) Fab' and a murine 734 (m734) Fab'. The m734 antibody recognizes an In-DTPA complex. This bsMAb was labeled with $^{125}$I and injected (7 Ci; 15 g) into athymic nude mice bearing a human pancreatic cancer xenograft (CaPan1). A non-targeting F(ab')$_2$ bsMAb made from chimeric rituximab (anti-CD20 monoclonal antibody) and m734, was labeled with $^{131}$I and co-injected as a control. At various time-points (4, 24, 36, 48, and 72-hours post-injection) mice were necropsied, the tissues removed and counted to determine percent-injected dose per gram (% ID/g). There was significantly greater tumor uptake of bsPAM4 at each time-point in comparison to the control bsRituximab (p<0.032 or better). Our past experience with this type of pre-targeting system suggested that a blood level of less than 1% ID/g was necessary to obtain good tumor:non-tumor ratios. At 36-hours post-administration of the bsPAM4 there was 1.10±0.40% ID/g in the blood which fell to 0.56±0.08% ID/g at 48 hours post-injection. Tumor uptake at these two time-points was 6.43±1.50% ID/g and 5.37±2.38% ID/g, respectively. These values were significantly higher than the control bsRituximab which had 0.65±0.33% ID/g and 0.47±0.19% ID/g in the tumor at 36 and 48 hours, respectively (p<0.018 and p<0.0098). Blood clearance rates, however, were very similar and were not significantly different.

Based on these data, a pre-targeting experiment was carried out in CaPan1 tumor-bearing mice in which radiolabeled peptide-haptens were injected 40-hours post-bsMAb administration. Two peptides, IMP-192 and IMP-156, were used, each containing divalent DTPA for recognition by the 734 MAb, but one has an additional group specific for binding $^{99m}$Tc stably (IMP-192). Tumor-bearing mice (tumor volume ~0.30 cm$^3$) were administered $^{125}$I-bsPAM4 (6 Ci; 15 g) followed 40 hours later by a radiolabeled peptide-hapten (34.5 Ci; 1.5×10$^{-11}$ moles; bsMAb:peptide=10:1). One group of mice received $^{99m}$Tc-labeled IMP192 while a second group of mice received $^{111}$In-labeled IMP156. Controls for non-specific targeting included two groups that received $^{125}$I-bsRituximab prior to administration of radiolabeled peptide and two other groups that received $^{111}$In- or $^{99m}$Tc-labeled peptide alone.

Mice were sacrificed at 3 and 24 hours after the administration of peptides and the % ID/g determined for the tumor and various tissues. Consistent with our previous findings, there was significantly greater bsPAM4 in the tumors in comparison to the non-targeting control bsRituximab, 8.2±3.4% and 0.3±0.08% ID/g, respectively (p<0.0001). This translated into a significantly greatly tumor uptake of $^{111}$In-IMP156 (20.2±5.5% ID/g vs. 0.9±0.1% ID/g, p<0.0001). There was also significantly greater tumor uptake of $^{99m}$Tc-IMP192 in the mice pre-targeted with bsPAM4 than in those pre-targeted with bsRituximab (16.8±4.8% ID/g vs. 1.1±0.2% ID/g, p<0.0005). Tumor uptake of each peptide, when administered alone, was significantly less than in those mice that received the bsPAM4 (0.2±0.05% ID/g and 0.1±0.03% ID/g for $^{99m}$Tc-IMP192 and $^{111}$In-IMP156, p<0.0004 and p<0.0001, respectively).

As with the 3-hour time-point, there was significantly more bsPAM4 in the tumors at 24 hours post-injection of peptide (64 hours post bsMAb administration) than bsRituximab (6.4±2.2% ID/g vs. 0.2±0.09% ID/g, respectively; p<0.0001). At this time-point there was 11.1±3.5% ID/g $^{111}$In-IMP156 and 12.9±4.2% ID/g $^{99m}$Tc-IMP192 in the tumors of mice pre-targeted with bsPAM4 versus 0.5±0.2% ID/g and 0.4±0.03% ID/g in bsRIT pre-targeted tumors (p<0.0008 and p<0.0002, respectively). In the mice that received peptide alone, there was significantly less $^{99m}$Tc-IMP192 in the tumors (0.06±0.02% ID/g, p<0.0007) and $^{111}$In-IMP156 (0.09±0.02% ID/g, p<0.0002) in comparison to the bsPAM4 pre-targeted peptides.

TABLE 6

Tumor:Non-Tumor Tissue Ratios at Early Time-Points.

| Tissue | Pre-targeted $^{111}$In-Peptide (3-Hours) | | Pre-targeted $^{99m}$Tc-Peptide (3-Hours) | | $^{125}$I-bsPAM4 F(ab')$_2$ (4-Hours) | |
|---|---|---|---|---|---|---|
| | Mean | (±STD) | Mean | (±STD) | Mean | (±STD) |
| Tumor | 1.00 | 0.00 | 1.00 | 0.00 | 1.00 | 0.00 |
| Liver | 36.07 | 11.74 | 16.66 | 7.19 | 2.34 | 0.61 |
| Spleen | 33.40 | 20.62 | 14.62 | 9.12 | 2.15 | 0.74 |
| Kidney | 7.79 | 2.81 | 8.13 | 3.33 | 1.10 | 0.20 |
| Lung | 44.55 | 12.99 | 15.75 | 5.85 | 1.58 | 0.37 |
| Blood | 36.47 | 8.28 | 9.93 | 5.21 | 0.47 | 0.11 |
| Bone | 123.24 | 40.00 | — | — | — | — |
| W. Bone | 378.00 | 124.57 | — | — | — | — |
| Pancreas | 155.55 | 30.07 | 73.29 | 32.85 | 4.65 | 1.23 |
| Tumor Wt. (g) (±STD) | 0.189 | (0.070) | 0.174 | (0.050) | 0.179 | (0.139) |

The table above presents the tumor:non-tumor ratios (T:NT) of various tissues for these groups, each at an early time-point post-administration of radiolabeled product. It is important to note that at 4-hours post-administration of bsPAM4×m734 F(ab')$_2$, the tumor:blood ratio was less than 2:1. However, at 3-hours post-administration, the pre-targeted $^{111}$In-IMP156 and $^{99m}$Tc-IMP192 had significantly greater tumor:nontumor ratios for all tissues examined and in particular tumor:blood ratios were equal to 36:1 and 9:1, (p<0.001 and p<0.011, respectively). When we examined tumor:blood ratios at the 24-hour time-point, the pre-targeted $^{111}$In-IMP156 and $^{99m}$Tc-IMP192 had significantly higher values, 274:1 and 80:1, respectively, versus 4:1 for $^{125}$I-bsPAM4 alone (p<0.0002). These data strongly suggest the ability to utilize this pretargeted bsPAM4 approach with short half-life, high energy radioisotopes that would then deliver high radiation dose to tumor with minimal radiation dose to non-tumor tissues.

It will be apparent to those skilled in the art that various modifications and variations can be made to the products, compositions, methods. and processes of this invention. Thus, it is intended that the present invention cover such modifications and variations, provided they come within the scope of the appended claims and their equivalents.

The disclosure of all publications, patents and patent applications cited above are expressly incorporated herein by reference in their entireties to the same extent as if each were incorporated by reference individually.

---

What is claimed is:

1. A humanized antibody or an antigen binding fragment thereof, comprising the complementarity-determining regions (CDRs) of a murine PAM4 monoclonal antibody (MAb) and the framework (FR) regions of the light and heavy chain variable regions of a human antibody and the light and heavy chain constant regions of a human antibody, wherein the CDRs of the light chain variable region of the humanized PAM4 Mab comprise CDR1 (SASSSVSSSYLY, SEQ ID NO:1); CDR2 (STSNLAS, SEQ ID NO:2); and CDR3 (HQWNRYPYT, SEQ ID NO:3); and the CDRs of the heavy chain variable region of the humanized PAM4 Mab comprise CDR1 (SYVLH, SEQ ID NO:4); CDR2 (YINPYNDGTQYNEKFKG, SEQ ID NO:5) and CDR3 (GFGGSYGFAY, SEQ ID NO:6), wherein said antibody or fragment thereof binds to a domain located between the amino terminus and the start of a repeat domain of MUC1.

2. The humanized antibody or fragment thereof of claim 1, wherein the FRs of the light and heavy chain variable regions of said humanized antibody or fragment thereof comprise at least one amino acid substituted from the corresponding FRs of a murine PAM4 Mab.

3. The humanized antibody or fragment thereof of claim 2, wherein said substituted amino acid from said murine PAM4 Mab is at least one amino acid selected from the group consisting of amino acid residue 5, 27, 30, 38, 48, 66, 67, and 69 of the murine heavy chain variable region of FIG. 1B, PAM4 VH amino acid sequence (SEQ ID NO: 11).

4. The humanized antibody or fragment thereof of claim 2, wherein said amino acid from said murine Mab is at least one amino acid selected from the group consisting of amino acid residue 21, 47, 59, 60, 85, 87, and 100 of the murine light chain variable region FIG. 1A, PAM4V$_k$ sequence (SEQ ID NO: 9).

5. The antibody or fragment thereof of claim 1, wherein said antibody or fragment thereof comprises a hPAM4 V$_H$ amino acid sequence (SEQ ID NO: 16) of FIG. 4A and a hPAM4 V$_k$ amino acid sequence (SEQ ID NO: 19) of FIG. 4B.

6. A cancer cell targeting diagnostic or therapeutic conjugate comprising an antibody component that comprises an antibody or fragment thereof of claim 1, wherein said antibody component is bound to at least one diagnostic and/or therapeutic agent.

7. The diagnostic conjugate according to claim 6, wherein said diagnostic/detection agent is selected from the group comprising a radionuclide, a contrast agent, and a photoactive diagnostic/detection agent.

8. The diagnostic conjugate of claim 7, wherein said diagnostic/detection agent is a radionuclide.

9. The diagnostic conjugate of claim 8, wherein said radionuclide has an energy between 20 and 4,000 keV.

10. The diagnostic conjugate of claim 8, wherein said radionuclide is a gamma-, beta- or a positron-emitting isotope.

11. The diagnostic conjugate of claim 10, wherein said radionuclide is selected from the group consisting of $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, or other gamma-, beta-, or positron-emitters.

12. The diagnostic conjugate of claim 7, wherein said diagnostic/detection agent is a radiological contrast agent.

13. The diagnostic conjugate of claim 12, wherein said contrast agent is a paramagnetic ion.

14. The diagnostic conjugate of claim 13, wherein said paramagnetic ion is a metal comprising chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III).

15. The diagnostic conjugate of claim 12, wherein said contrast agent is a metal comprising lanthanum (III), gold (III), lead (II), or bismuth (III).

16. The diagnostic conjugate of claim 7, wherein said diagnostic/detection agent is a photoactive diagnostic/detection agent.

17. The diagnostic conjugate of claim 16, wherein said photoactive diagnostic/detection agent is a fluorescent labeling compound selected from the group comprising fluorescein isothiocyanate, rhodamine, phycoerytherin, phycocyanin, allophycocyanin, o-phthaldehyde and fluorescamine.

18. The diagnostic conjugate of claim 16, wherein said photoactive diagnostic/detection agent is a chemiluminescent labeling compound selected from the group comprising luminol, isoluminol, an aromatic acridinium ester, an imidazole, an acridinium salt and an oxalate ester.

19. The diagnostic conjugate of claim 16, wherein said photoactive diagnostic/detection agent is a bioluminescent compound selected from the group comprising luciferin, luciferase and aequorin.

20. The therapeutic conjugate of claim 6, wherein said therapeutic agent is selected from the group consisting of a radionuclide, an immunomodulator, a hormone, a hormone antagonist, an oligonucleotide, an enzyme, an enzyme inhibitor, a photoactive therapeutic agent, a cytotoxic agent, an angiogenesis inhibitor, and a combination thereof.

21. The therapeutic conjugate of claim 20, wherein said oligonucleotide is an antisense oligonucleotide.

22. The therapeutic conjugate of claim 21, wherein said oligonucleotide is an antisense oligonucleotide against an oncogene.

23. The therapeutic conjugate of claim 22, wherein said oncogene is bcl-2 or p53.

24. The therapeutic conjugate of claim 20, wherein said therapeutic agent is a cytotoxic agent.

25. The therapeutic conjugate of claim 24, wherein said cytotoxic agent is a drug or a toxin.

26. The therapeutic conjugate of claim 25, wherein said drug possesses the pharmaceutical property selected from the group consisting of antimitotic, alkylating, antimetabolite, antiangiogenic, apoptotic, alkaloid, and antibiotic agents and combinations thereof.

27. The therapeutic conjugate of claim 25, wherein said drug is selected from the group consisting of nitrogen mustards, gemcitabine, ethylenimine derivatives, alkyl sulfonates, nitrosoureas, triazenes, folic acid analogs, anthracyclines, taxanes, SN-38, COX-2 inhibitors, pyrimidine analogs, purine analogs, antibiotics, enzymes, enzyme inhibitors, epipodophyllotoxins, platinum coordination complexes, Vinco alkaloids, substituted ureas, methyl hydrazine derivatives, adrenocortical suppressants, hormone antagonists, endostatin, taxols, camptothecins, doxorubicins and their analogs, antimetabolites, alkylating agents, antimitotics, antiangiogenic, apoptotic agents, methotrexate, CPT-11, and a combination thereof.

28. The therapeutic conjugate of claim 25, wherein said toxin is derived from a source selected from the group comprising an animal, a plant, and a microbial source.

29. The therapeutic conjugate of claim 25, wherein said toxin is selected from the group consisting of ricin, abrin, alpha toxin, saporin, ribonuclease (RNase), DNase I, *Staphylococcal* enterotoxin-A, pokeweed antiviral protein, gelonin, diphtherin toxin, *Pseudomonas* exotoxin, and *Pseudomonas* endotoxin.

30. The therapeutic conjugate of claim 20, wherein said therapeutic agent is an immunomodulator.

31. The therapeutic conjugate of claim 30, wherein said immunomodulator is selected from the group consisting of a cytokine, a stem cell growth factor, a lymphotoxin, a hematopoietic factor, a colony stimulating factor (CSF), an interferon (IFN), a stem cell growth factor, erythropoietin, thrombopoletin and a combination thereof.

32. The therapeutic conjugate of claim 31, wherein said lymphotoxin is tumor necrosis factor (TNF), said hematopoietic factor is an interleukin (IL), said colony stimulating factor is granulocyte-colony stimulating factor (G-CSF) or granulocyte macrophage-colony stimulating factor (GM-CSF)), said interferon is interferons-alpha, -beta or -gamma, and said stem cell growth factor is designated "S1 factor".

33. The therapeutic conjugate of claim 30, wherein said immunomodulator comprises IL-1, IL-2, IL-3, IL-6, IL-10, IL-12, IL-18, IL-21, interferon-gamma, TNF-alpha or a combination thereof.

34. The therapeutic conjugate of claim 20, wherein said therapeutic agent is a radionuclide.

35. The therapeutic conjugate of claim 34, wherein said radionuclide has an energy between 60 and 700 keV.

36. The therapeutic conjugate of claim 35, wherein said radionuclide is selected from the group consisting of $^{32}$P, $^{33}$P, $^{47}$Sc, $^{64}$Cu, $^{67}$Cu, $^{67}$Ga, $^{86}$Y, $^{90}$Y, $^{111}$Ag, $^{111}$In, $^{125}$I, $^{131}$I, $^{142}$Pr, $^{153}$Sm, $^{161}$Tb, $^{166}$Dy, $^{166}$Ho, $^{177}$Lu, $^{186}$Re, $^{188}$Re, $^{189}$Re, $^{212}$Pb, $^{212}$Bi, $^{213}$Bi, $^{211}$At, $^{223}$Ra and $^{225}$Ac, and combinations thereof.

37. The therapeutic conjugate of claim 20, wherein said therapeutic agent is a photoactive therapeutic agent.

38. The therapeutic conjugate of claim 37, wherein said photoactive therapeutic agent is selected from the group comprising chromogens and dyes.

39. The therapeutic conjugate of claim 20, wherein said therapeutic agent is an enzyme.

40. The therapeutic conjugate of claim 39, wherein said enzyme is selected from the group comprising malate dehydrogenase, *staphylococcal* nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetyicholinesterase.

41. A multivalent, multispecific antibody or fragment thereof comprising at least one humanized PAM4 antibody or fragment thereof according to claim 1 and one or more hapten binding sites having affinity towards hapten molecules.

42. The antibody or fragment thereof of claim 41, further comprising a diagnostic or therapeutic agent.

43. An antibody fusion protein or fragment thereof comprising at least two humanized PAM4 Mabs or fragments thereof according to claim 1.

* * * * *

UNITED STATES PATENT AND TRADEMARK OFFICE
CERTIFICATE OF CORRECTION

PATENT NO.        : 7,282,567 B2                                Page 1 of 1
APPLICATION NO.   : 10/461885
DATED             : October 16, 2007
INVENTOR(S)       : David M. Goldenberg et al.

It is certified that error appears in the above-identified patent and that said Letters Patent is hereby corrected as shown below:

At column 76, line 8, please replace "Vinco" with --vinca--.

At column 76, line 31, please replace "thrombopoletin" with --thrombopoietin--.

At column 77, line 3, please replace "acetyicholinesterase." with --acetylcholinesterase.--

Signed and Sealed this

Eighteenth Day of December, 2007

JON W. DUDAS
*Director of the United States Patent and Trademark Office*

UNITED STATES PATENT AND TRADEMARK OFFICE
CERTIFICATE OF CORRECTION

PATENT NO. : 7,282,567 B2  
APPLICATION NO. : 10/461885  
DATED : October 16, 2007  
INVENTOR(S) : David M. Goldenberg et al.

Page 1 of 1

It is certified that error appears in the above-identified patent and that said Letters Patent is hereby corrected as shown below:

Column 4, line 40, replace "VH" with --Vk--

Column 4, line 41, replace "Vk" with --VH--

Column 74, line 55, replace "VH" with --Vk--

Column 74, line 57, replace "Vk" with --VH--

Signed and Sealed this  
Twentieth Day of March, 2012

David J. Kappos  
*Director of the United States Patent and Trademark Office*